United States Patent
Harada et al.

(10) Patent No.: US 7,396,836 B2
(45) Date of Patent: Jul. 8, 2008

(54) PYRIMIDINE COMPOUND AND MEDICINAL COMPOSITION THEREOF

(75) Inventors: Hitoshi Harada, Ibaraki (JP); Masato Ueda, Ibaraki (JP); Yoshihiko Kotake, Ibaraki (JP); Masahiro Yasuda, Ibaraki (JP); Daisuke Iida, Ibaraki (JP); Junichi Nagakawa, Ibaraki (JP); Makoto Nakagawa, Ibaraki (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 210 days.

(21) Appl. No.: 10/492,905

(22) PCT Filed: Oct. 22, 2002

(86) PCT No.: PCT/JP02/10952

§ 371 (c)(1),
(2), (4) Date: Apr. 16, 2004

(87) PCT Pub. No.: WO03/035639

PCT Pub. Date: May 1, 2003

(65) Prior Publication Data

US 2005/0004149 A1   Jan. 6, 2005

(30) Foreign Application Priority Data

Oct. 22, 2001   (JP) ............... 2001-324018

(51) Int. Cl.
A61K 31/505 (2006.01)
C07D 239/02 (2006.01)

(52) U.S. Cl. ............. 514/275; 544/330; 544/331; 544/332; 544/333

(58) Field of Classification Search ............... 514/275; 544/330, 331, 332, 333
See application file for complete search history.

(56) References Cited

U.S. PATENT DOCUMENTS

| | | | |
|---|---|---|---|
| 4,725,600 A | 2/1988 | Takaya et al. | |
| 5,935,966 A | 8/1999 | Suto et al. | |
| 6,096,753 A | 8/2000 | Spohr et al. | |
| 6,750,232 B2 | 6/2004 | Harada et al. | |
| 7,160,892 B2 | 1/2007 | Harada et al. | |
| 7,189,717 B2 * | 3/2007 | Yasuda et al. ............. | 514/235.8 |
| 2002/0156087 A1 | 10/2002 | Nuss et al. | |
| 2003/0171383 A1 * | 9/2003 | Yasuda et al. ............. | 514/263.3 |
| 2006/0235225 A1 | 10/2006 | Harada et al. | |
| 2007/0078151 A1 | 4/2007 | Harada et al. | |

FOREIGN PATENT DOCUMENTS

| | | |
|---|---|---|
| DE | 294255 A | 9/1991 |
| DE | 294255 A5 | 9/1991 |
| EP | 1 136 482 A1 | 9/2001 |
| EP | 1 136 486 A1 | 9/2001 |
| EP | 1 283 056 A1 | 2/2003 |
| EP | 1 439 175 A1 | 7/2004 |
| JP | 2-52360 A | 2/1990 |
| JP | 6-211856 A | 8/1994 |
| JP | 11-263789 A | 9/1999 |
| WO | WO 96/39400 A1 | 12/1996 |
| WO | WO96/39400 A1 | 12/1996 |
| WO | WO 97/33883 A1 | 9/1997 |
| WO | WO97/33883 A1 | 9/1997 |
| WO | WO 98/24780 A2 | 6/1998 |
| WO | WO98/24780 A2 | 6/1998 |
| WO | WO 98/24782 A2 | 6/1998 |
| WO | WO98/24782 A2 | 6/1998 |
| WO | WO99/65897 A1 | 12/1999 |
| WO | WO 99/65897 A1 | 12/1999 |
| WO | WO-00/18758 A1 | 4/2000 |
| WO | WO01/80893 A1 | 11/2000 |
| WO | WO01/02400 A2 | 1/2001 |
| WO | WO 01/62233 A2 | 8/2001 |
| WO | WO01/62233 A2 | 8/2001 |

(Continued)

OTHER PUBLICATIONS

Takagi et al., Chem. Pharm. Bull, vol. 23, No. 10, pp. 2427-2431, (1975).
Bennett et al., J. of Med. Chem., vol. 21, No. 7, pp. 623-628, (1978).
Chemical Abstracts, vol. 124, Abs. No. 317095s (1996).
Chemical Abstracts, vol. 124, Abs. No. 117229b (1996).

(Continued)

*Primary Examiner*—Rei-tsang Shiao
(74) *Attorney, Agent, or Firm*—Birch, Stewart, Kolasch & Birch, LLP

(57) ABSTRACT

A compound having excellent adenosine receptor ($A_1$, $A_{2A}$, $A_{2B}$ receptor) antagonistic action, of the following formula, a salt thereof or a solvate of them:

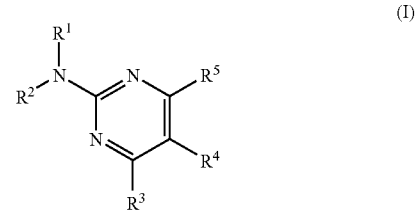

(I)

wherein, $R^1$ and $R^2$, same or different, each represents a hydrogen atom, an alkyl group, an alkenyl group, an alkynyl group, a cycloalkyl group, a cycloalkenyl group, an aromatic hydrocarbon cyclic group, an acyl group or an alkylsulfonyl group, which groups may be substituted (except the hydrogen atom); $R^3$ represents a hydrogen atom, a halogen atom, a cyano group, an alkyl group, an alkenyl group, an alkynyl group, an aromatic hydrocarbon cyclic group, a nitrogen atom, an oxygen atom or a sulfur atom, which groups may be substituted (except the hydrogen atom, the halogen atom and the cyano group); $R^4$ represents an aromatic hydrocarbon cyclic group which may be substituted, and $R^5$ represents an aromatic hydrocarbon cyclic group which may be substituted.

34 Claims, No Drawings

FOREIGN PATENT DOCUMENTS

| | | |
|---|---|---|
| WO | WO-01/70727 A1 | 9/2001 |
| WO | WO 01/80893 A1 | 11/2001 |
| WO | WO 02/20495 A2 | 3/2002 |
| WO | WO02/20495 A2 | 3/2002 |
| WO | WO02/22608 A1 | 3/2002 |
| WO | WO 02/22608 A1 | 3/2002 |
| WO | WO02/24893 A2 | 3/2002 |
| WO | WO 02/24893 A2 | 3/2002 |
| WO | WO 02/64586 A2 | 8/2002 |
| WO | WO02/064586 A2 | 8/2002 |
| WO | WO-03/035639 A1 | 5/2003 |
| WO | WO-2004/016605 A1 | 2/2004 |

OTHER PUBLICATIONS

Chemical Abstracts, vol. 124, Abs. No. 8438y (1996).
Chemical Abstracts, vol. 123, Abs. No. 9410z (1995).
Chemical Abstracts, vol. 122, Abs. No. 290759f (1995).
Chemical Abstracts, vol. 120, Abs. No. 270297j (1994).
Chemical Abstracts, vol. 118, Abs. No. 139216y (1993).
Chemical Abstracts, vol. 115, Abs. No. 182897w (1991).
Chemical Abstracts, vol. 112, Abs. No. 20957b (1990).
Chemical Abstracts, vol. 109, Abs. No. 149486q (1988).
Chemical Abstracts, vol. 105, Abs. No. 208819t (1986).
Chemical Abstracts, vol. 101, Abs. No. 230414w (1984).
Chemical Abstracts, vol. 199, Abs. No. 175707g (1983).
Chemical Abstracts, vol. 98, Abs. No. 71884a (1983).
Chemical Abstracts, vol. 95, Abs. No. 97702c (1981).
Chemical Abstracts, vol. 93, Abs. No. 95175t (1980).
Chemical Abstracts, vol. 92, Abs. No. 106451n (1980).
Chemical Abstracts, vol. 90, Abs. No. 54903y (1979).
Chemical Abstracts, vol. 79, Abs. No. 105183w (1973).
Chemical Abstracts, vol. 77, Abs. No. 164349m (1972).
Chemical Abstracts, vol. 74, Abs. No. 3578h (1971).
Chemical Abstracts, vol. 68, Abs. No. 59520b (1968).
Chemical Abstracts, vol. 67, Abs. No. 43775g (1967).
Mally et al., J. Pharm. Pharmacol., vol. 46, pp. 515-517, (1994).
Jarvis et al., Euro. J. of Pharm., vol. 168, pp. 243-246, (1989).
Martinez-Mir et al., Neroscience, vol. 42, No. 3, pp. 697-706, (1991).
Hubble et al., Neurology, vol. 58, pp. A162-A163, (2002).
Hannah et al., Bio. & Med. Chem., vol. 8, pp. 739-750 (2000).
Van Calker et al., J. of Neuro., vol. 33, pp. 999-1005, (1979).
Bruns et al., Molecular Pharm., vol. 29, pp. 331-346, (1986).
Wan et al., J. of Neuro., vol. 55, No. 5, (1990).
Feoktistov et al., J. Clin. Invest., vol. 96, pp. 1979-1986, (1995).
Dixon et al., Brit. J. of Pharm., vol. 118, pp. 1461-1468, (1996).
Peachy et al., Arch. Pharm., vol. 359, pp. 140-146, (1999).
Kadowaki et al., Brit. J. of Pharm., vol. 129, pp. 871-876, (2000).
Zwart et al., Drug Dev. Res., vol. 48, pp. 95-103, (1999).
Kim et a., J. Med. Chem., vol. 43, pp. 1165-1172, (2000).
Bioorg. Med. Chem. (2000), 8(4), p. 739-50.
Chemical Abstracts, vol. 124, abs. No. 317095.
Chemical Abstracts, vol. 124, abs. No. 117229, RN=173036-78-7 etc.
Chemical Abstracts, vol. 124, abs. No. 8438.
Chemical Abstracts, vol. 123, abs. No. 9410.
Chemical Abstracts, vol. 122, abs. No. 290759, RN=136507-03-4.
Chemical Abstracts, vol. 120, abs. No. 270297.
Chemical Abstracts, vol. 118, abs. No. 139216.
Chemical Abstracts, vol. 115, abs. No. 182897.
Chemical Abstracts, vol. 112, abs. No. 20957.
Chemical Abstracts, vol. 109, abs. No. 149486.
Chemical Abstracts, vol. 105, abs. No. 208819.
Chemical Abstracts, vol. 101, abs. No. 230414, RN=93300-20-0.
Chemical Abstracts, vol. 99, abs. No. 175707.
Chemical Abstracts, vol. 98, abs. No. 71884.
Chemical Abstracts, vol. 95, abs. No. 97702.
Chemical Abstracts, vol. 93, abs. No. 95175.
Chemical Abstracts, vol. 92, abs. No. 106451, RN=72621-33-1.
Chemical Abstracts, vol. 90, abs. No. 54903.
J. Med. Chem., (1978), 21(7), p. 623-8.
Chem. Pharm. Bull., (1975), 23(10), p. 2427-31
Chemical Abstracts, vol. 79, abs. No. 105183.
Chemical Abstracts, vol. 77, abs. No. 164349.
Chemical Abstracts, vol. 74, abs. No. 3578.
Chemical Abstracts, vol. 68, abs. No. 59520.
Chemical Abstracts, vol. 67, abs. No. 43775.
Kabbe, Liebigs Ann. Chem., vol. 704, pp. 144-149 (1967).
Skulnick et al., J. Med. Chem., vol. 28, pp. 1864-1869 (1985).
Chemical Abstracts, vol. 77, Columbus, Ohio, US; abstract No. 34471J, XP002961047.
Witek, Dissert. Pharm. Pharmacol., vol. 24, No. 1, pp. 27-37 (1972).

* cited by examiner

PYRIMIDINE COMPOUND AND MEDICINAL COMPOSITION THEREOF

FIELD OF THE INVENTION

The present invention relates to a novel pyrimidine compound, a production process thereof, and a pharmaceutical preparation containing it and use thereof.

PRIOR ART

Adenosine is an important regulatory factor involved in many intracellular metabolisms in the living body such as regulation of energy levels, cAMP levels, opening and closing potassium channels, and inflow of calcium ions into cells, and its interaction with G protein-coupled adenosine receptors on the surface of a cell is essential for exhibiting these physiological activities. Adenosine receptors were classified under two subtypes, $A_1$ receptor and $A_2$ receptor based on the involvement in adenylate cyclase (J. Neurochem., 33, 999-1003, (1979)), and thereafter, the $A_2$ receptor has been classified under two subtypes, $A_{2A}$ and $A_{2B}$, based on the affinity for $A_2$ receptor agonists, NECA and CGS-21680 (Mol. Pharmacol., 29, 331-346, (1986); J. Neurochem., 55, 1763-1771, (1990)). Four receptor subtypes, $A_1$, $A_2$ ($A_{2A}$ and $A_{2B}$) and $A_3$, have been identified until now. The $A_1$ receptor is a protein coupled with $G_{i/o}$ family proteins. It serves to inhibit the adenylate cyclase as a result of binding with a ligand to thereby decrease the cAMP level and serves to activate phospholipase C (PLC) to thereby promote the production of inositol-1,4,5-triphosphate ($IP_3$) and to release the intracellular calcium ions. The $A_3$ receptor is a receptor serving to decrease the cAMP level and to activate PLC to thereby promote the $IP_3$ production and the release of calcium ions, as the $A_1$ receptor. In contrast, the $A_{2A}$ and $A_{2B}$ receptors are receptors serving to activate the adenylate cyclase and promote the production of cAMP. There is a report that the $A_{2B}$ receptor couples with PLC via a $G_q/G_{11}$ protein or promotes the production of $IP_3$ and the flow of calcium ions into cells (J. din. Invest., 96, 1979-1986 (1995)). These subtypes are different from one another in their distribution in tissues; that is, the $A_1$ receptor occurs relatively abundantly, for example, in the heart, aorta and bladder, the $A_{2A}$ receptor is distributed relatively abundantly, for example, in the eyeballs and skeletal muscles, the $A_3$ receptor, for example, in the spleen, uterus, and prostate, and the $A_{2B}$ receptor, for example, in the proximal colon, and subsequently in the eyeballs, lung, uterus and bladder (Br. J. Pharmacol., 118, 1461-1468 (1996)). It is believed that these adenosine receptor subtypes can exhibit specific functions, respectively, due to the difference in distribution in the tissues as well as the difference in adenosine level among the locations and the difference in affinity for the ligand among the subtypes. Adenosine is involved in a variety of physiological functions such as platelet aggregation, heart rate, smooth muscle tonus, inflammation, release of neurotransmitters, neurotransmission, hormone release, cell-differentiation, cell growth, cell death, and DNA biosynthesis. Accordingly, the relation between adenosine and diseases such as central nervous system diseases, cardiovascular diseases, inflammatory diseases, respiratory diseases, and immune diseases has been suggested, and the efficacy of agonists/antagonists of the adenosine receptors on these diseases has been expected. Antagonists against the adenosine receptors, particularly those against the adenosine $A_2$ receptor have been discussed as effective as an agent for treating or preventing diabetes mellitus, diabetic complications, diabetic retinopathy, obesity or asthma and have been expected useful as, for example, a hypoglycemic agent, an agent for improving glucose intolerance, an insulin sensitizer, a hypotensive agent, a diuretic agent, an antidepressant, an agent for treating osteoporosis, an agent for treating Parkinson's disease, an agent for treating Alzheimer's disease, an agent for treating an inflammatory bowel disease, or an agent for treating Crohn's disease.

Certain important reports have been made on the relation between the adenosine A2 receptor and the intestinal tract. For example, certain reports have been made that the A2 receptor mediates a colon longitudinal muscle relaxation action (Naunyn-Schmiedeberg's Arch. Pharmacol., 359, 140-146 (1999)), and that the $A_1$ receptor, and the $A_{2B}$ receptor occurring in the longitudinal muscle mediate a relaxation action of adenosine against the contraction of distal colon longitudinal muscle of a guinea pig (Br. J. Pharmacol., 129, 871-876 (2000)). Such $A_{2B}$ receptor antagonists do not induce diarrhea, have an excellent defecation-promoting action and are expected as an agent for treating and/or preventing various constipation. They are also expected as being useful for treating and/or preventing irritable bowel syndrome, constipation accompanying irritable bowel syndrome, organic constipation or constipation accompanying enteroparalytic ileus and for evacuating intestinal tracts at the time of examination of digestive tracts or before and after an operation.

Furthermore, in the formation of clinical condition of Parkinson's disease, it has been importantly reported that, adenosine is extremely closely involved through the adenosine $A_{2A}$ receptor in addition to dopamine. For instance, it has been reported that the effects for improving the symptoms of Parkinson's disease will be enhanced by use of L-DOPA together with theophylline which is known as a non-selective adenosine receptor antagonist (J. Pharm. Pharmacol., 46, 515-517, (1994)). Also, it has been reported that selective adenosine $A_{2A}$ receptor antagonists are effective to various kinds of Parkinson's disease animal models (JP 1994-211856 A). Parkinson's disease is caused by the degradation or death of dopaminergic neurons projected from the compact layer of midbrain substantia nigra to the corpus striatum. Although the progress of the disease cannot be prevented, the symptomatic treatment with L-DOPA preparations is nevertheless a fundamental treatment making up for a shortage to dompamine. However, the long-term usage of the L-DOPA preparations will reduce the effectiveness thereof and produce some side effects such as involuntary movements and mental symptoms. Therefore, the biggest problem is that sufficient therapeutic effects cannot be attained by the L-DOPA preparations. The distribution of adenosine $A_{2A}$ receptors in the brain is confined in the corpus striatum, nucleus accumbens, and olfactory tubercle (Eur. J. Pharmacol., 168, 243-246 (1989)), SO that the adenosine $A_{2A}$ receptors have been estimated to play an important role in motor function control in the corpus striatum. In addition, it has been reported that the degradation of dopaminergic neurons in the compact layer of midbrain substantia nigra does not affect the adenosine $A_{2A}$ receptor binding ability of the corpus striatum and there is no difference between Parkinson's disease subjects and normal healthy subjects with respect to the total number of adenosine $A_{2A}$ receptors (Neuroscience, 42, 697-706, 1991). Recently, it has been also reported that selective adenosine $A_{2A}$ receptor antagonists are harmless and improve the motor functions of the subjects suffering from progressive Parkinson's disease without exaggerating dyskinesia with L-DOPA preparations (Neurology, 58 (suppl. 3) S21. 001 (2002.4)). As is evident from these findings, it is expected that the adenosine $A_{2A}$ receptor antagonists are useful as therapeutic agents for Parkinson's disease.

Following compounds have been reported as those having antagonistic action on adenosine $A_{2A}$ and/or adenosine $A_2B$ receptors:
(1) Compounds represented by the following formulae:
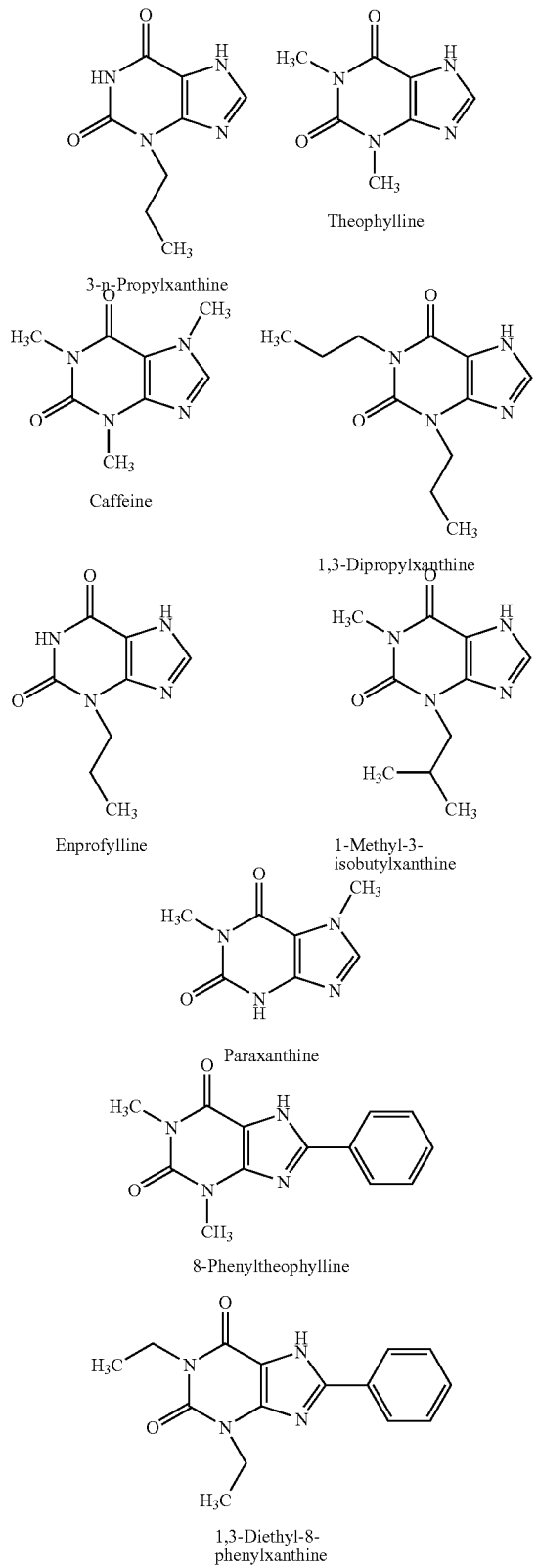
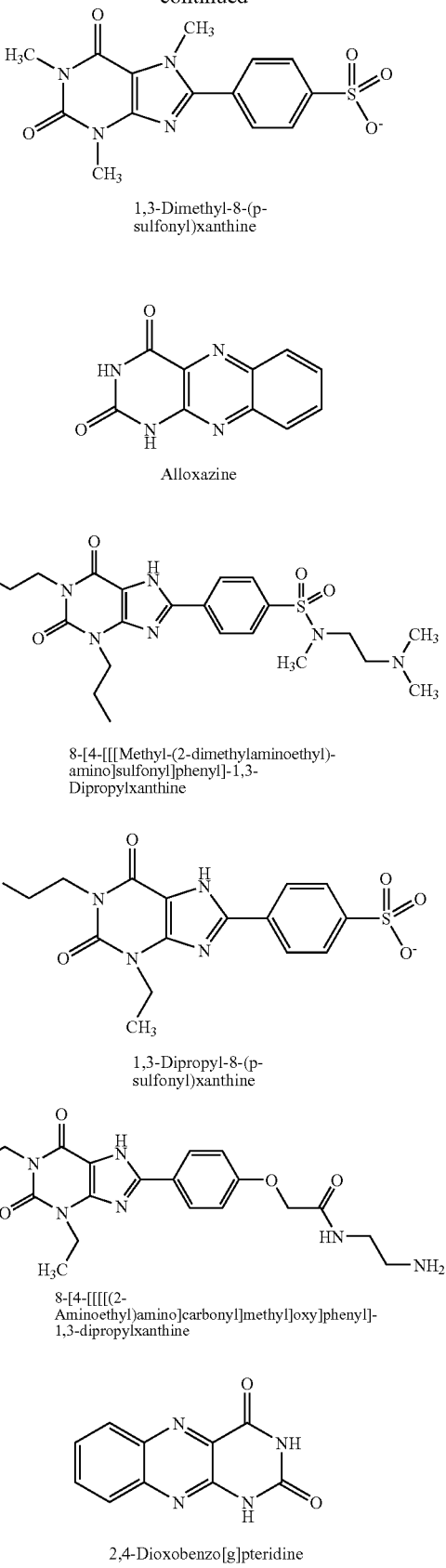

(2) A purine derivative represented by the formula:

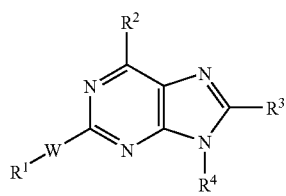

(wherein R¹ represents (1) the formula:

(wherein X represents a hydrogen atom, a hydroxyl group, a lower alkyl group which may be substituted, a lower alkoxy group which may be substituted, etc.; and R⁵ and R⁶ are the same as or different from each other and each represents a hydrogen atom, a lower alkyl group which may be substituted, a saturated or unsaturated cycloalkyl group having three to eight carbon atoms which may be substituted, etc.) or (2) a 5 or 6-membered aromatic ring which may have one or more substituents and a hetero atom; W represents the formula:

—CH₂CH₂—, —CH═CH— or —C≡C—; R² represents an amino group which may be substituted with a lower alkyl group which may be substituted, etc.; R³ represents a cycloalkyl group having three to eight carbon atoms which may be substituted, an aryl group which may be substituted, etc.; and R⁴ represents a lower alkyl group which may be substituted, etc.), a pharmacologically acceptable salt thereof or a hydrate of them (JP-A 11-263789).

(3) A purine compound represented by the formula:

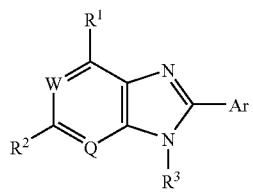

(wherein R¹ represents a hydrogen atom, a hydroxyl group, a halogen atom, an alkyl group having one to eight carbon atoms which may be substituted, etc.; R² represents an amino group which may be substituted with an alkyl group having one to eight carbon atoms, etc.; R³ represents an alkynyl group having three to eight carbon atoms which may be substituted with a halogen atom, a hydroxyl group or an alkyl group having one to four carbon atoms, etc.; Ar represents an aryl group which may be substituted, a heteroaryl group which may be substituted, etc.; and Q and W are the same as or different from each other and each represents N or CH), a pharmacologically acceptable salt thereof or a hydrate of them (JP-A 11-188484).

(4) A₂ᵦ receptor antagonists described in Drug Development Research, 48: 95-103 (1999) and J. Med. Chem., 43: 1165-1172 (2000).

(5) A₂ₐ receptor antagonists represented by the following formula:

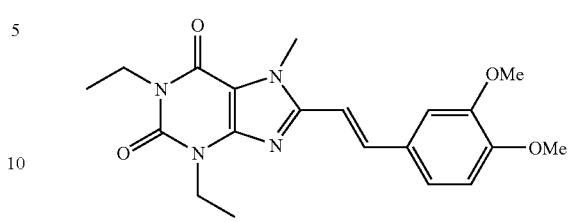

KW6002

(JP-A 6-211856).

As pyrimidine compounds, there are only reports relating to 5,6-aromatic substituted pyrimidine compounds in publications such as WO97/33883, WO98/24782 and WO99/65897. However, the relation between these compounds and the adenosine receptors has been neither reported nor suggested and has not yet been known.

As is described above, compounds having an adenosine receptor antagonism, among them, compounds having an adenosine A₂ receptor antagonism, that is, compounds having an A₂ₐ and/or A₂ᵦ receptor antagonism are expected to exhibit an excellent action as a medicament, and strong demands have been made to provide such compounds. However, compounds which have an excellent antagonism against the adenosine receptors and effectively act as a medicament have not yet been found. Accordingly, an object of the present invention is to search for and find compounds which serve to inhibit the adenosine receptors (A₂ₐ and A₂ᵦ receptors) and are useful as an agent for treating or preventing a disease to which the adenosine receptors relate.

DISCLOSURE OF THE INVENTION

After intensive investigations under these circumstances, the present inventors have succeeded, for the first time, to synthesize a compound represented by the formula:

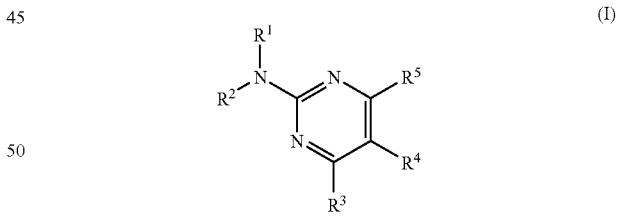

(I)

(in the formula, R¹ and R² are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted, a 5 to 14-membered aromatic heterocyclic group which may be substituted, an acyl group having one to six carbon atoms which may be substituted or an alkylsulfonyl group having one to six carbon atoms which may be substituted; $R^3$ represents a hydrogen atom, a halogen atom, a cyano group, an alkyl group having one to six carbon atoms which may be substituted, an alkenyl group having two to six carbon atoms which may be substituted, an alkynyl group having two to six carbon atoms which may be substituted, an aromatic hydrocarbon cyclic group having six to fourteen carbon atoms which may be substituted, a 5 to 14-membered aromatic heterocyclic group which may be substituted, a nitrogen atom which may be substituted, an oxygen atom which may be substituted or a sulfur atom which may be substituted; $R^4$ represents an aromatic hydrocarbon cyclic group having six to fourteen carbon atoms which may be substituted, a 5 to 14-membered aromatic heterocyclic group which may be substituted or a 5 to 14-membered non-aromatic heterocyclic group having at least one or more unsaturated bonds which may be substituted; and $R^5$ represents an aromatic hydrocarbon cyclic group having six to fourteen carbon atoms which may be substituted or a 5 to 14-membered aromatic heterocyclic group which may be substituted), a salt thereof or a solvate of them. They have unexpectedly found that the compound, a salt thereof or a solvate them have an excellent antagonism against the adenosine $A_2$ receptors, that is against the $A_{2A}$ and/or $A_{2B}$ receptor. After further intensive investigations, they have found that the compound, a salt thereof or a solvate of them has a remarkable efficacy on diseases to which the adenosine receptors, particularly the adenosine $A_2$ receptors, further particularly the adenosine $A_{2A}$ and/or $A_{2B}$ receptor relates, and that it is efficacious for preventing and/or treating various constipation (constipation, irritable bowel syndrome, constipation accompanying irritable bowel syndrome, organic constipation, constipation accompanying enteroparalytic ileus, constipation accompanying congenital digestive tract dysfunction, or constipation accompanying ileus) and is also useful as an agent for treating, preventing or improving, for example, diabetes mellitus, diabetic complications, diabetic retinopathy, obesity or asthma, and as a hypoglycemic agent, an agent for improving glucose intolerance, an insulin sensitizer, a hypotensive agent, a diuretic agent, an antidepressant, an agent for treating osteoporosis, an agent for treating Parkinson's disease, an agent for treating Alzheimer's disease, an agent for treating an inflammatory intestinal disease or an agent for treating Crohn's disease. The present invention has been accomplished based on these findings.

That is, the present invention relates to (1) a compound represented by the formula:

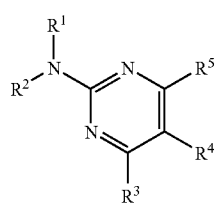

(I)

(in the formula, $R^1$ and $R^2$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted, a 5 to 14-membered aromatic heterocyclic group which may be substituted, an acyl group having one to six carbon atoms which may be substituted or an alkylsulfonyl group having one to six carbon atoms which may be substituted; $R^3$ represents a hydrogen atom, a halogen atom, a cyano group, an alkyl group having one to six carbon atoms which may be substituted, an alkenyl group having two to six carbon atoms which may be substituted, an alkynyl group having two to six carbon atoms which may be substituted, an aromatic hydrocarbon cyclic group having six to fourteen carbon atoms which may be substituted, a 5 to 14-membered aromatic heterocyclic group which may be substituted, a nitrogen atom which may be substituted, an oxygen atom which may be substituted or a sulfur atom which may be substituted; $R^4$ represents an aromatic hydrocarbon cyclic group having six to fourteen carbon atoms which may be substituted, a 5 to 14-membered aromatic heterocyclic group which may be substituted or a 5 to 14-membered non-aromatic heterocyclic group having at least one or more unsaturated bonds which may be substituted; and $R^5$ represents an aromatic hydrocarbon cyclic group having six to fourteen carbon atoms which may be substituted or a 5 to 14-membered aromatic heterocyclic group which may be substituted), a salt thereof or a solvate of them; (2) the compound described in (1), a salt thereof or a solvate of them, wherein $R^1$ and $R^2$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted, a 5 to 14-membered aromatic heterocyclic group which may be substituted, an acyl group having one to six carbon atoms which may be substituted or an alkylsulfonyl group having one to six carbon atoms which may be substituted (provided that a group represented by the formula:

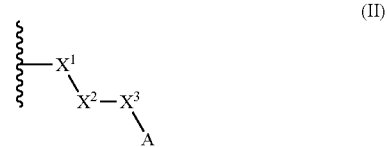

(II)

(wherein A represents an aromatic hydrocarbon cyclic group having six to fourteen carbon atoms which may be substituted or a 5 to 14-membered aromatic heterocyclic group which may be substituted; $X^1$ and $X^2$ are the same as or different from each other and each represents a carbon atom which may be substituted; and $X^3$ represents a nitrogen atom which may be substituted, an oxygen atom, or a carbon atom which may be substituted) is excluded); $R^3$ represents a cyano group; and $R^4$ represents an aromatic hydrocarbon cyclic group having six to fourteen carbon atoms which may be substituted, a 5 to 14-membered aromatic heterocyclic group which may be substituted or a 5 to 14-membered non-aromatic heterocyclic group having one or more unsaturated bonds which may be substituted; (3) the compound described in (1), a salt thereof or a solvate of them, wherein $R^1$ and $R^2$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted, a 5 to 14-membered aromatic heterocyclic group which may be substituted, an acyl group having one to six carbon atoms which may be substituted or an alkylsulfonyl group having one to six carbon atoms which may be substituted (provided that a group represented by the formula:

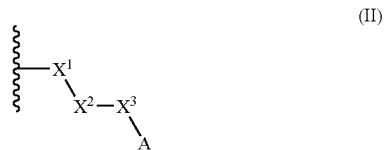

(II)

(wherein A represents an aromatic hydrocarbon cyclic group having six to fourteen carbon atoms which may be substituted or a 5 to 14-membered aromatic heterocyclic group which may be substituted; $X^1$ and $X^2$ are the same as or different from each other and each represents a carbon atom which may be substituted; and $X^3$ represents a nitrogen atom which may be substituted, an oxygen atom or a carbon atom which may be substituted) is excluded); $R^3$ represents a halogen atom, an alkyl group having one to six carbon atoms which may be substituted, an alkenyl group having two to six carbon atoms which may be substituted, an alkynyl group having two to six carbon atoms which may be substituted, an aromatic hydrocarbon cyclic group having six to fourteen carbon atoms which may be substituted, a 5 to 14-membered aromatic heterocyclic group which may be substituted, an oxygen atom which may be substituted or a sulfur atom which may be substituted; and $R^4$ represents a 4-pyridyl group, a 4-pyrimidinyl group, a 4-quinazolinyl group, a 4-quinolyl group or a 6-isoquinolinyl, each of which may have one or two substituents; (4) the compound described in (1), a salt thereof or a solvate of them, wherein $R^1$ and $R^2$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted, a 5 to 14-membered aromatic heterocyclic group which may be substituted, an acyl group having one to six carbon atoms which may be substituted or an alkylsulfonyl group having one to six carbon atoms which may be substituted (provided that a group represented by the formula:

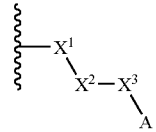

(II)

(wherein A represents an aromatic hydrocarbon cyclic group having six to fourteen carbon atoms which may be substituted or a 5 to 14-membered aromatic heterocyclic group which may be substituted; $X^1$ and $X^2$ are the same as or different from each other and each represents a carbon atom which may be substituted; and $X^3$ represents a nitrogen atom which may be substituted, an oxygen atom or a carbon atom which may be substituted) is excluded); and $R^4$ represents a 5 to 14-membered non-aromatic heterocyclic group having at least one or more unsaturated bonds which may be substituted (provided that the group represented by the above formula (II) is excluded); (5) the compound described in (1), a salt thereof or a solvate of them, wherein $R^1$ and $R^2$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted, a 5 to 14-membered aromatic heterocyclic group which may be substituted, an acyl group having one to six carbon atoms which may be substituted or an alkylsulfonyl group having one to six carbon atoms which may be substituted (provided that a group represented by the formula:

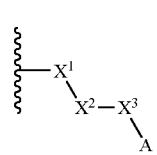

(II)

(wherein A represents an aromatic hydrocarbon cyclic group having six to fourteen carbon atoms which may be substituted or a 5 to 14-membered aromatic heterocyclic group which may be substituted; $X^1$ and $X^2$ are the same as or different from each other and each represents a carbon atom which may be substituted; and $X^3$ represents a nitrogen atom which may be substituted, an oxygen atom or a carbon atom which may be substituted) is excluded); and $R^4$ represents a 4-pyridyl group, a 4-pyrimidinyl group, a 4-quinazolinyl group, a 4-quinolyl group or a 6-isoquinolinyl, each of which may have one or two substituents including at least one of a cyano group and a carbamoyl group represented by the formula:

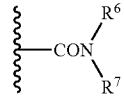

(III)

(wherein $R^6$ and $R^7$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted or a 5 to 14-membered aromatic heterocyclic group which may be substituted); (6) the compound described in (2), a salt thereof or a solvate of them, wherein $R^4$ represents a 5 to 14-membered aromatic heterocyclic group which may be substituted or a 5 to 14membered non-aromatic heterocyclic group having at least one or more unsaturated bonds which may be substituted; and $R^5$ represents a 5 to 14-membered aromatic heterocyclic group which may be substituted; (7) the compound described in (3), a salt thereof or a solvate of them, wherein $R^3$ represents a halogen atom, an alkyl group having one to six carbon atoms which may be substituted, an alkenyl group having two to six carbon atoms which may be substituted, an alkynyl group having two to six carbon atoms which may be substituted, a 5 to 14-membered aromatic heterocyclic group which may be substituted, an oxygen atom which may be substituted or a sulfur atom which may be substituted; and $R^5$ represents a 5 to 14-membered aromatic heterocyclic group which may be substituted; (8) the compound described in (4), a salt thereof or a solvate of them, wherein $R^3$ represents a hydrogen atom, a halogen atom, a cyano group, an alkyl group having one to six carbon atoms which may be substituted, an alkenyl group having two to six carbon atoms which may be substituted, an alkynyl group having two to six carbon atoms which may be substituted, a 5 to 14-membered aromatic heterocyclic group which may be substituted, a nitrogen atom which may be substituted, an oxygen atom which may be substituted or a sulfur atom which may be substituted; and $R^5$ represents a 5 to 14-membered aromatic heterocyclic group which may be substituted; (9) the compound described in (5), a salt thereof or a solvate of them, wherein $R^3$ represents a hydrogen atom, a halogen atom, a cyano group, an alkyl group having one to six carbon atoms which may be substituted, an alkenyl group having two to six carbon atoms which may be substituted, an alkynyl group having two to six carbon atoms which may be substituted, a 5 to 14-membered aromatic heterocyclic group which may be substituted, an oxygen atom which may be substituted or a sulfur atom which may be substituted; and $R^5$ represents a 5 to 14-membered aromatic heterocyclic group which may be substituted; (10) the compound described in any one of (1) to (9), wherein $R^1$ and/or $R^2$ represents a hydrogen atom, an alkyl group having one to six carbon atoms which may be substituted or an acyl group having one to six carbon atoms which may be substituted (provided that a group represented by the formula:

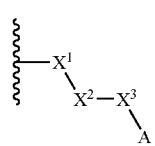

(II)

(wherein A represents an aromatic hydrocarbon cyclic group having six to fourteen carbon atoms which may be substituted or a 5 to 14-membered aromatic heterocyclic group which may be substituted; $X^1$ and $X^2$ are the same as or different from each other and each represents a carbon atom which may be substituted; and $X^3$ represents a nitrogen atom which may be substituted, an oxygen atom, or a carbon atom which may be substituted) is excluded), a salt thereof or a solvate of them; (11) the compound described in any one of (1), (4) and (8), wherein $R^4$ is a group represented by the formula (IV)

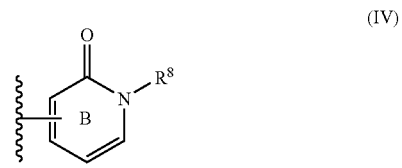

(IV)

(wherein $R^8$ represents a group selected from the following substituent group a; and the ring B may be substituted with one to four groups selected from the following substituent group a.

Substituent Group a

The group consisting of a hydrogen atom, a halogen atom, a hydroxyl group, a nitro group, a cyano group, an alkyl group having one to six carbon atoms which may be substituted, an alkenyl group having two to six carbon atoms which may be substituted, an alkynyl group having two to six carbon atoms which may be substituted, an alkoxy group having one to six carbon atoms which may be substituted, an alkenyloxy group having two to six carbon atoms which may be substituted, an alkynyloxy group having two to six carbon atoms which may be substituted, an alkylthio group having one to six carbon atoms which may be substituted, an alkenylthio group having two to six carbon atoms which may be substituted, an alkynylthio group having two to six carbon atoms which may be substituted, an aliphatic acyl group having two to seven carbon atoms, a carbamoyl group which may be substituted, an arylacyl group, a heteroarylacyl group, an amino group which may be substituted, an alkylsulfonyl group having one to six carbon atoms which may be substituted, an alkenylsulfonyl group having two to six carbon atoms which may be substituted, an alkynylsulfonyl group having two to six carbon atoms which may be substituted, an alkylsulfinyl group having one to six carbon atoms which may be substituted, an alkenylsulfinyl group having two to six carbon atoms which may be substituted, an alkynylsulfinyl group having two to six carbon atoms which may be substituted, a formyl group, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted and a 5 to 14-membered aromatic heterocyclic group which may be substituted), a salt thereof or a solvate of them; (12) the compound described in (11), a salt thereof or a solvate of them, wherein $R^3$ is a hydrogen atom, a halogen atom, a cyano group, an alkyl group having one to six carbon atoms which may be substituted, a 5 to 14-membered aromatic heterocyclic group which may be substituted, an amino group or an oxygen atom which may be substituted; (13) the compound described in (11) or (12), wherein $R^4$ is a group represented by the formula:

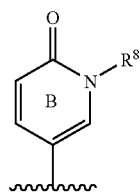

(V)

or the formula:

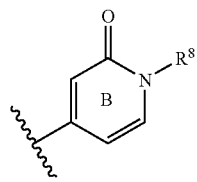

(VI)

(in the formulae (V) and (VI), $R^8$ represents a group selected from the following substituent group a; and the ring B may be substituted with one to four groups selected from the following substituent group a.

Substituent Group a

The group consisting of a hydrogen atom, a halogen atom, a hydroxyl group, a nitro group, a cyano group, an alkyl group having one to six carbon atoms which may be substituted, an alkenyl group having two to six carbon atoms which may be substituted, an alkynyl group having two to six carbon atoms which may be substituted, an alkoxy group having one to six carbon atoms which may be substituted, an alkenyloxy group having two to six carbon atoms which may be substituted, an alkynyloxy group having two to six carbon atoms which may be substituted, an alkylthio group having one to six carbon atoms which may be substituted, an alkenylthio group having two to six carbon atoms which may be substituted, an alkynylthio group having two to six carbon atoms which may be substituted, an aliphatic acyl group having two to seven carbon atoms, a carbamoyl group which may be substituted, an arylacyl group, a heteroarylacyl group, an amino group which may be substituted, an alkylsulfonyl group having one to six carbon atoms which may be substituted, an alkenylsulfonyl group having two to six carbon atoms which may be substituted, an alkynylsulfonyl group having two to six carbon atoms which may be substituted, an alkylsulfinyl group having one to six carbon atoms which may be substituted, an alkenylsulfinyl group having two to six carbon atoms which may be substituted, an alkynylsulfinyl group having two to six carbon atoms which may be substituted, a formyl group, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms and a 5 to 14-membered aromatic heterocyclic group which may be substituted), a salt thereof or a solvate of them; (14) the compound described in any one of (1), (3) and (7), a salt thereof or a solvate of them, wherein $R^4$ is 4-pyridyl group which may have one or two substituents; (15) the compound described in (14), a salt thereof or a solvate of them, wherein $R^3$ is a halogen atom, a cyano group, an alkyl group having one to six carbon atoms which may be substituted, a 5 to 14-membered aromatic heterocyclic group which may be substituted or an oxygen atom which may be substituted; (16) the compound described in (14) or (15), wherein $R^4$ is a 4-pyridyl group which may have one or two substituents comprising at least one of a cyano group and a carbamoyl group represented by the formula (III):

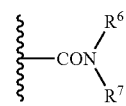

(III)

(wherein $R^6$ and $R^7$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted or a 5 to 14-membered aromatic heterocyclic group which may be substituted), a salt thereof or a solvate of them; (17) the compound described in any one of (1) to (5), a salt thereof or a solvate of them, wherein $R^5$ is a naphthyl group or a phenyl group, each of which may be substituted; (18) the compound described in any one of (1) to (16), a salt thereof or a solvate of them, wherein $R^5$ is pyrrolyl group, pyridyl group, pyridazinyl group, pyrimidinyl group, pyrazinyl group, thienyl group, thiazolyl group, furyl group, quinolinyl group, isoquinolinyl group, phthalazinyl group, naphthyridinyl group, indolyl group or isoindolyl group, each of which may be substituted; (19) a pharmaceutical composition comprising the compound described in any one of (1) to (18), a salt thereof or a solvate of them; (20) the composition described in (19), which is an agent for treating or preventing a disease to which an adenosine receptor relates; (21) the composition described in (19), which is an agent for treating or preventing a disease to which an adenosine $A_2$ receptor relates; (22) the composition described in (19), which is an agent for treating or preventing a disease to which an adenosine $A_{2A}$ receptor relates; (23) the composition described in (19), which is an agent for treating or preventing a disease to which an adenosine $A_{2B}$ receptor relates; (24) the composition described in (19), which is an adenosine receptor antagonist; (25) the composition described in (19), which is an adenosine $A_2$ receptor antagonist; (26) the composition described in (19), which is adenosine $A_{2A}$ receptor antagonist; (27) the composition described in (19), which is adenosine $A_{2B}$ receptor antagonist; (28) the composition described in any one of (19) to (22), (24) to (26), which is an agent for treating Parkinson's disease or an antidepressant; (29) the composition described in any one of (19) to (21), (23) to (25) and (27), which is a defecation-promoting agent; (30) the composition described in any one of (19) to (21), (23) to (25) and (27), which is an agent for treating, preventing or improving constipation; (31) the composition described in (30), wherein the constipation is functional constipation; (32) the composition described in (30), which is an agent for treating, preventing or improving irritable bowel syndrome, constipation accompanying irritable bowel syndrome, organic constipation, constipation accompanying enteroparalytic ileus, constipation accompanying congenital digestive tract dysfunction or constipation accompanying ileus; (33) the composition described in (19), which is used for evacuating intestinal tracts at the time of examination of digestive tracts or be fore and after an operation; (34) use of the compound described in any one of (1) to (18), a salt thereof or a solvate of them for producing a defecation-promoting agent; (35) the composition described in (19), which is an agent for treating or preventing diabetes mellitus, diabetic complications, diabetic retinopathy, obesity or asthma; (36) the composition described in (19), which is a hypoglycemic agent, an agent for improving glucose intolerance or an insulin sensitizer; and (37) the composition described in (19), which is a hypotensive agent, a diuretic agent, an agent for treating osteoporosis, an agent for treating Alzheimer's disease, an agent for treating an inflammatory bowel disease or an agent for treating Crohn's disease.

Hereinafter, the meanings of symbols, terms, etc. used in the present description will be described, and the present invention will be illustrated in detail.

In the present description, the "antagonist" refers to an agent which has affinity for and inactivates an adenosine receptor, preferably an adenosine $A_2$ receptor, that is, an $A_{2A}$ and/or $A_{2B}$ receptor.

The "disease to which an adenosine receptor relates" used in the present description refers to a disease to which an adenosine $A_1$ receptor, $A_{2A}$ receptor, $A_{2B}$ receptor or $A_3$ receptor relates, and includes various constipation (e.g., functional constipation, irritable bowel syndrome, constipation accompanying irritable bowel syndrome, organic constipation, constipation accompanying enteroparalytic ileus, constipation accompanying congenital digestive tract dysfunction and constipation accompanying ileus), diabetes mellitus, diabetic complications, diabetic retinopathy, obesity, asthma, as well as diseases against which a hypoglycemic agent, agent for improving glucose intolerance, insulin sensitizer, antihypertensive drug, diuretic agent, antidepressant, agent for treating osteoporosis, agent for treating Parkinson's disease, agent for treating Alzheimer's disease, agent for treating an inflammatory bowel disease or agent for treating Crohn's disease is efficacious.

The present invention provides a method for treating or preventing a disease to which an adenosine receptor relates, and a method for promoting defecation, which comprises administering a pharmacologically effective dose of the compound represented by the formula (I), a salt thereof or a solvate of them to a patient.

The present invention further provides use of the compound represented by the formula (I), a salt thereof or a solvate of them for producing an agent for treating or preventing a disease to which an adenosine receptor relates, or a defecation-promoting agent.

The compound represented by the formula (I), a salt thereof or a solvate of them is also useful as a defecation-promoting agent and is used for evacuating intestinal tracts at the time of examination of digestive tracts or be fore and after an operation.

The term "and/or" used in the present description means and includes both the cases of "and" and "or".

In the present description, there is the case where the structural formula of a compound represents a definite isomer for the sake of convenience. However, the present invention includes all isomers such as geometrical isomers, optical isomers based on asymmetric carbon, rotational isomer, stereoisomers and tautomers, and mixtures of these isomers and is not limited by the description of the formula illustrated for the sake of convenience. The compound can be any of isomers or a mixture thereof. Accordingly, although it is possible that an asymmetric carbon atom is present in a molecule and that optically active substance and racemic substance may therefore be present, the present invention is not limited thereto but covers any of them. Further, crystal polymorphism may be present but, again, there is no limitation but any of single crystal form or a mixture will do. The compound (I) or its salt according to the present invention may be a non-solvate or a solvate, and either of them are included in the scope of claims for patent in the present invention. A metabolite which is generated by decomposing the compound (I) according to the present invention in vivo, and a prodrug of the compound (I) or its salt according to the present invention are also included in the scope of claims for patent in the present invention.

The "halogen atom" used in the present description represents an atom such as fluorine atom, chlorine atom, bromine atom or iodine atom, and fluorine atom, chlorine atom and bromine atom are preferred.

The "$C_{1-6}$ alkyl group" used in the present description represents an alkyl group having one to six carbon atoms, including linear or branched alkyl groups such as methyl group, ethyl group, n-propyl group, iso-propyl group, n-butyl group, iso-butyl group, sec-butyl group, t-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1-methyl-2-ethylpropyl group, 1-ethyl-2-methylpropyl group, 1,1,2-trimethylpropyl group, 1-propylpropyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group or 3-methylpentyl group.

The "$C_{2-6}$ alkenyl group" used in the present description represents an alkenyl group having two to six carbon atoms, and suitable examples of the group are vinyl group, allyl group, 1-propenyl group, 2-propenyl group, isopropenyl group, 2-methyl-1-propenyl group, 3-methyl-1-propenyl group, 2-methyl-2-propenyl group, 3-methyl-2-propenyl group, 1-butenyl group, 2-butenyl group, 3-butenyl group, 1-pentenyl group, 1-hexenyl group, 1,3-hexadienyl group and 1,6-hexadienyl group.

The "$C_{2-6}$ alkynyl group" used in the present description represents an alkynyl group having two to six carbon atoms, and suitable examples of the group are ethynyl group, 1-propynyl group, 2-propynyl group, 1-butynyl group, 2-butynyl group, 3-butynyl group, 3-methyl-1-propynyl group, 1-ethynyl-2-propynyl group, 2-methyl-3-propynyl group, 1-pentynyl group, 1-hexynyl group, 1,3-hexadiynyl group, and 1,6-hexadiynyl group.

The "$C_{1-6}$ alkoxy group" used in the present description represents an alkoxy group having one to six carbon atoms, such as methoxy group, ethoxy group, n-propoxy group, iso-propoxy group, sec-propoxy group, n-butoxy group, iso-butoxy group, sec-butoxy group, t-butoxy group, n-pentyloxy group, iso-pentyloxy group, sec-pentyloxy group, n-hexoxy group, iso-hexoxy group, 1,1-dimethylpropyloxy group, 1,2-dimethylpropoxy group, 2,2-dimethylpropyloxy group, 2-ethylpropoxy group, 1-methyl-2-ethylpropoxy group, 1-ethyl-2-methylpropoxy group, 1,1,2-trimethylpropoxy group, 1,1-dimethylbutoxy group, 1,2-dimethylbutoxy group, 2,2-dimethylbutoxy group, 2,3-dimethylbutyloxy group, 2-ethylbutoxy group, 1,3-dimethylbutoxy group, 2-methylpentoxy group, 3-methylpentoxy group or hexyloxy group.

The "$C_{2-6}$ alkenyloxy group" used in the present description represents an alkenyloxy group having two to six carbon atoms, and suitable examples of the group are vinyloxy group, allyloxy group, 1-propenyloxy group, 2-propenyloxy group, isopropenyloxy group, 2-methyl-1-propenyloxy group, 3-methyl-1-propenyloxy group, 2-methyl-2-propenyloxy group, 3-methyl-2-propenyloxy group, 1-butenyloxy group, 2-butenyloxy group, 3-butenyloxy group, 1-pentenyloxy group, 1-hexenyloxy group, 1,3-hexadienyloxy group, and 1,6-hexadienyloxy group.

The "$C_{2-6}$ alkynyloxy group" used in the present description represents an alkynyloxy group having two to six carbon atoms, and suitable examples thereof are ethynyloxy group, 1-propynyloxy group, 2-propynyloxy group, 1-butynyloxy group, 2-butynyloxy group, 3-butynyloxy group, 3-methyl-1-propynyloxy group, 1-ethynyl-2-propynyloxy group, 2-methyl-3-propynyloxy group, 1-pentynyloxy group, 1-hexynyloxy group, 1,3-hexadiynyloxy group, and 1,6-hexadiynyloxy group.

The "alkylthio group having one to six carbon atoms" used in the present description refers to an alkylthio group having one to six carbon atoms, such as methylthio group, ethylthio group, n-propylthio group, iso-propylthio group, sec-propylthio group, n-butylthio group, iso-butylthio group, sec-butylthio group, t-butylthio group, n-pentylthio group, iso-pentylthio group, sec-pentylthio group, n-hexylthio group, isohexylthio group, 1,1-dimethylpropylthio group, 1,2-dimethylpropylthio group, 2,2-dimethylpropylthio group, 2-ethylpropylthio group, 1-methyl-2-ethylpropylthio group, 1-ethyl-2-methylpropylthio group, 1,1,2-trimethylpropylthio group, 1,1-dimethylbutylthio group, 1,2-dimethylbutylthio group, 2,2-dimethylbutylthio group, 2,3-dimethylbutylthio group, 1,3-dimethylbutylthio group, 2-ethylbutylthio group, 2-methylpentylthio group or 3-methylpentylthio group.

The "alkenylthio group having two to six carbon atoms" used in the present description refers to an alkenylthio group having two to six carbon atoms, and suitable examples thereof are vinylthio group, allylthio group, 1-propenylthio group, 2-propenylthio group, isopropenylthio group, 2-methyl-1-propenylthio group, 3-methyl-1-propenylthio group, 2-methyl-2-propenylthio group, 3-methyl-2-propenylthio group, 1-butenylthio group, 2-butenylthio group, 3-butenylthio group, 1-pentenylthio group, 1-hexenylthio group, 1,3-hexadienylthio group, and 1,6-hexadienylthio group.

The "alkynylthio group having two to six carbon atoms" used in the present description represents an alkynylthio group having two to six carbon atoms, and suitable examples thereof are ethynylthio group, 1-propynylthio group, 2-propynylthio group, 1-butynylthio group, 2-butynylthio group, 3-butynylthio group, 3-methyl-1-propynylthio group, 1-ethynyl-2-propynylthio group, 2-methyl-3-propynylthio group, 1-pentynylthio group, 1-hexynylthio group, 1,3-hexadiynylthio group, and 1,6-hexadiynylthio group.

The "cycloalkyl group having three to eight carbon atoms" used in the present description represents a cycloalkyl group comprising three to eight carbon atoms, such as cyclopropyl group, cyclobutyl group, cyclopentyl group, cyclohexyl group, cycloheptyl group or cyclooctyl group.

The "cycloalkenyl group having three to eight carbon atoms" used in the present invention represents a cycloalkenyl group comprising three to eight carbon atoms, such as cyclopropen-1-yl, cyclopropen-3-yl, cyclobuten-1-yl, cyclobuten-3-yl, 1,3-cyclobutadien-1-yl, cyclopenten-1-yl, cyclopenten-3-yl, cyclopenten-4-yl, 1,3-cyclopentadien-1-yl, 1,3-cyclopentadien-2-yl, 1,3-cyclopentadien-5-yl, cyclohexen-1-yl, cyclohexen-3-yl, cyclohexen-4-yl, 1,3-cyclohexadien-1-yl, 1,3-cyclohexadien-2-yl, 1,3-cyclohexadien-5-yl, 1,4-cyclohexadien-3-yl, 1,4-cyclohexadien-1-yl, cyclohepten-1-yl, cyclohepten-3-yl, cyclohepten-4-yl, cyclohepten-5-yl, 1,3-cyclohepten-2-yl, 1,3-cyclohepten-1-yl, 1,3-cycloheptadien-5-yl, 1,3-cycloheptadien-6-yl, 1,4-cycloheptadien-3-yl, 1,4-cycloheptadien-2-yl, 1,4-cycloheptadien-1-yl, 1,4-cycloheptadien-6-yl, 1,3,5-cycloheptatrien-3-yl, 1,3,5-cycloheptatrien-2-yl, 1,3,5-cycloheptatrien-1-yl, 1,3,5-cycloheptatrien-7-yl, cycloocten-1-yl, cycloocten-3-yl, cycloocten-4-yl, cycloocten-5-yl, 1,3-cyclooctadien-2-yl, 1,3-cyclooctadien-1-yl, 1,3-cyclooctadien-5-yl, 1,3-cyclooctadien-6-yl, 1,4-cyclooctadien-3-yl, 1,4-cyclooctadien-2-yl, 1,4-cyclooctadien-1-yl, 1,4-cyclooctadien-6-yl, 1,4-cyclooctadien-7-yl, 1,5-cyclooctadien-3-yl, 1,5-cyclooctadien-2-yl, 1,3,5-cyclooctatrien-3-yl, 1,3,5-cyclooctatrien-2-yl, 1,3,5-cyclooctatrien-1-yl, 1,3,5-cyclooctatrien-7-yl, 1,3,6-cyclooctatrien-2-yl, 1,3,6-cyclooctatrien-1-yl, 1,3,6-cyclooctatrien-5-yl or 1,3,6-cyclooctatrien-6-yl group.

The "5 to 14-membered non-aromatic heterocyclic group" used in the present description refers to a monocyclic, bicyclic or tricyclic 5 to 14-membered non-aromatic heterocyclic group and containing one or more hetero atoms selected from the group consisting of nitrogen atom, sulfur atom and oxygen atom. Specific examples of the group are pyrrolidinyl group, piperidinyl group, piperazinyl group, pyrazolinyl group, morpholinyl group, tetrahydrofuryl group, tetrahydropyranyl group, dihydrofuryl group, dihydropyranyl group, imidazolinyl group, and oxazolinyl group. The non-aromatic heterocyclic group also includes a group derived from pyridone ring, and a non-aromatic fused ring (e.g., a group derived from phthalimide ring or succinimide ring).

The "aromatic cyclic hydrocarbon group having six to fourteen carbon atoms" and the "aryl" used in the present description represent an aromatic cyclic hydrocarbon group comprising six to fourteen carbon atoms and include monocyclic groups, as well as fused groups such as bicyclic groups and tricyclic groups. Specific examples of the group include phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, and benzocyclooctenyl group.

The "5 to 14-membered aromatic heterocyclic group" and the "heteroaryl" used in the present description represent a monocyclic, bicyclic or tricyclic 5 to 14-membered aromatic heterocyclic group containing one or more hetero atoms selected from nitrogen atom, sulfur atom and oxygen atom. Specific examples of the group include 1) a nitrogen-containing aromatic heterocyclic group such as pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolizyl group, phthalazyl group, naphthyridinyl group, quinoxalyl group, quinazolinyl group, cinnolinyl group, pteridinyl group, imidazotriazinyl group, pyrazinopyridazinyl group, acridinyl group, phenanthridinyl group, carbazolyl group, carbazolinyl group, perimidinyl group, phenanthrolinyl group, phenacinyl group, imidazopyridinyl group, imidazopyrimidinyl group, pyrazolopyridinyl group or pyrazolopyridinyl group; 2) a sulfur-containing aromatic heterocyclic group such as thienyl group or benzothienyl group; 3) an oxygen-containing aromatic heterocyclic group such as furyl group, pyranyl group, cyclopentapyranyl group, benzofuryl group or isobenzofuryl group; and 4) an aromatic heterocyclic group containing two or more different hetero atoms, such as thiazolyl group, isothiazolyl group, benzothiazolyl group, benzthiadiazolyl group, phenothiazinyl group, isoxazolyl group, furazanyl group, phenoxazinyl group, oxazolyl group, isoxazoyl group, benzoxazolyl group, oxadiazolyl group, pyrazolooxazolyl group, imidazothiazolyl group, thienofuranyl group, furopyrrolyl group or pyridooxazinyl group.

The "aliphatic acyl group having two to seven carbon atoms" used in the present description represents an atomic group derived from an aliphatic carboxyl group having two to seven carbon atoms by removing OH group from its carboxyl group, and suitable examples thereof are acetyl group, propionyl group and butyroyl group.

The "arylacyl group" used in the present description represents a carbonyl group substituted with an aromatic cyclic hydrocarbon group having six to fourteen carbon atoms, and the "heteroarylacyl group" represents a carbonyl group substituted with a 5 to 14-membered aromatic heterocyclic group. The "aromatic cyclic hydrocarbon group having six to fourteen carbon atoms" and the "5 to 14-membered aromatic heterocyclic group" as used herein have the same meanings as defined above.

Suitable examples of the "alkylsulfonyl group having one to six carbon atoms", "alkenylsulfonyl group having two to six carbon atoms" and "alkynylsulfonyl group having two to six carbon atoms" used in the present description include methylsulfonyl group, ethylsulfonyl group, n-propylsulfonyl group, iso-propylsulfonyl group, n-butylsulfonyl group, t-butylsulfonyl group, vinylsulfonyl group, allylsulfonyl group, iso-propenylsulfonyl group, iso-pentenylsulfonyl group, and ethynylsulfonyl group. Suitable examples of the "alkylsulfinyl group having one to six carbon atoms", "alkenylsulfinyl group having two to six carbon atoms" and "alkynylsulfinyl group having two to six carbon atoms" used in the present description include methylsulfinyl group, ethylsulfinyl group, n-propylsulfinyl group, iso-propylsulfinyl group, n-butylsulfinyl group, t-butylsulfinyl group, vinylsulfinyl group, allylsulfinyl group, iso-propenylsulfinyl group, iso-pentenylsulfinyl group, and ethynylsulfinyl group.

Examples of the "substituents" in the "amino group which may be substituted" used in the present description represents one or two groups selected from an alkyl group having one to six carbon atoms, an alkenyl group having two to six carbon atoms, an alkynyl group having two to six carbon atoms, an alkylsulfonyl group having one to six carbon atoms, an alkenylsulfonyl group having two to six carbon atoms, alkynylsulfonyl group having two to six carbon atoms, an alkylcarbonyl group having one to six carbon atoms, an alkenylcarbonyl group having two to six carbon atoms, an alkynylcarbonyl group having two to six carbon atoms, each of which may be substituted. In this connection, the substituents may be combined to form a 3 to 8-membered nitrogen-containing ring. Suitable examples of the "substituents" in the alkyl group having one to six carbon atoms, alkenyl group having two to six carbon atoms, alkynyl group having two to six carbon atoms, alkylsulfonyl group having one to six carbon atoms, alkenylsulfonyl group having two to six carbon atoms, alkynylsulfonyl group having two to six carbon atoms, $C_{1-6}$ alkylcarbonyl group, $C_{2-6}$ alkenylcarbonyl group and $C_{2-6}$ alkynylcarbonyl group include a hydroxyl group, a halogen atom, a nitrile group, an alkoxy group and $C_{1-6}$ alkylthio group. Particularly preferable examples of the above-mentioned "amino group which may be substituted" include methylamino group, ethylamino group, n-propylamino group, iso-propylamino group, n-butylamino group, iso-butylamino group, tert-butylamino group, n-pentylamino group, iso-pentylamino group, neopentylamino group, n-hexylamino group, 1-methylpropylamino group, 1,2-dimethylpropylamino group, 2-ethylpropylamino group, 1-methyl-2-ethylpropylamino group, 1-ethyl-2-methylpropylamino group, 1,1,2-trimethylpropylamino group, 1-methylbutylamino group, 2-methylbutylamino group, 1,1-dimethylbutylamino group, 2,2-dimethylbutylamino group, 2-ethylbutylamino group, 1,3-dimethylbutylamino group, 2-methylpentylamino group, 3-methylpentylamino group, N,N-dimethylamino group, N,N-diethylamino group, N,N-di(n-propyl)amino group, N,N-di(iso-propyl)amino group, N,N-di(n-butyl)amino group, N,N-di(iso-butyl)amino group, N,N-di(t-butyl)amino group, N,N-di(n-pentyl)amino group, N,N-di (iso-pentyl)amino group, N,N-di(neopentyl)amino group, N,N-di (n-hexyl)amino group, N,N-di(1-methylpropyl)amino group, N,N-di(1,2-dimethylpropyl)amino group, N-methyl-N-ethylamino group, N-ethyl-N-(n-propyl)amino group, N-methyl-N-(i-propyl)amino group, vinylamino group, allylamino group, (1-propenyl)amino group, isopropenylamino group, (1-buten-1-yl)amino group, (1-buten-2-yl)amino group, (1-buten-3-yl)amino group, (2-buten-1-yl) amino group, (2-buten-2-yl)amino group, N,N-divinylamino group, N,N-diallylamino group, N,N-di(1-propenyl)amino group, N,N-isopropenylamino group, N-vinyl-N-allylamino group, ethynylamino group, 1-propynylamino group, 2-propynylamino group, butynylamino group, pentynylamino group, hexynylamino group, N,N-diethynylamino group, N,N-(1-propynyl)amino group, N,N-(2-propynyl)amino group, N,N-dibutynylamino group, N,N-dipentynylamino group, N,N-dihexynylamino group, hydroxymethylamino group, 1-hydroxyethylamino group, 2-hydroxyethylamino group, 3-hydroxy-n-propyl group, methylsulfonylamino group, ethylsulfonylamino group, n-propylsulfonylamino group, iso-propylsulfonylamino group, n-butylsulfonylamino group, t-butylsulfonylamino group, vinylsulfonylamino group, allylsulfonylamino group, iso-propenylsulfonylamino group, iso-pentenylsulfonylamino group, ethynylsulfonylamino group, methylcarbonylamino group, ethylcarbonylamino group, n-propylcarbonylamino group, iso-propylcarbonylamino group, n-butylcarbonylamino group, butylcarbonylamino group, vinylcarbonylamino group, allylcarbonylamino group, iso-propenylcarbonylamino group, iso-pentenylcarbonylamino group, and ethynylcarbonylamino group.

Examples of the "substituents" in the phrase "which may be substituted" used in the present description include a halogen atom such as fluorine atom, chlorine atom, bromine atom or iodine atom; a hydroxyl group; a nitro group; a cyano group; an alkyl group having one to six carbon atoms such as methyl group, ethyl group, n-propyl group, iso-propyl group, n-butyl group, iso-butyl group, sec-butyl group, t-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group or 1-methyl-2-ethylpropyl group; an alkenyl group having two to six carbon atoms such as vinyl group, allyl group, 1-propenyl group, 2-propenyl group, isopropenyl group, 2-methyl-1-propenyl group, 3-methyl-1-propenyl group, 2-methyl-2-propenyl group, 3-methyl-2-propenyl group, 1-butenyl group, 2-butenyl group, 3-butenyl group, 1-pentenyl group, 1-hexenyl group, 1,3-hexadienyl group or 1,6-hexadienyl group; an alkynyl group having two to six carbon atoms such as ethynyl group, 1-propynyl group, 2-propynyl group, 1-butynyl group, 2-butynyl group, 3-butynyl group, 3-methyl-1-propynyl group, 1-ethynyl-2-propynyl group, 2-methyl-3-propynyl group, 1-pentynyl group, 1-hexynyl group, 1,3-hexadiynyl group or 1,6-hexadiynyl group; an alkoxy group having one to six carbon atoms such as methoxy group, ethoxy group, n-propoxy group, iso-propoxy group, sec-propoxy group, n-butoxy group, iso-butoxy group, sec-butoxy group, t-butoxy group, n-pentyloxy group, iso-pentyloxy group, sec-pentyloxy group or n-hexyloxy group; an alkenyloxy group having two to six carbon atoms such as vinyloxy group, allyloxy group, 1-propenyloxy group, 2-propenyloxy group or isopropenyloxy group; an alkynyloxy group having two to six carbon atoms such as ethynyloxy group, 1-propynyloxy group or 2-propynyloxy group; an alkylthio group having one to six carbon atoms such as methylthio group, ethylthio group, n-propylthio group, iso-propylthio group, sec-propyithic group, n-butylthio group, iso-butylthio group, sec-butylthio group or t-butylthio group; an alkenylthio group having two to six carbon atoms such as vinylthio group, allylthio group, 1-propenylthio group or 2-propenylthio group; an alkynylthio group having two to six carbon atoms such as ethynylthio group, 1-propynylthio group or 2-propynylthio group; an aliphatic acyl group having two to seven carbon atoms such as acetyl group, propionyl group or butyroyl group; carbamoyl group; an arylacyl group; a heteroarylacyl group; an amino group; an alkylsulfonyl group having one to six carbon atoms, an alkenylsulfonyl group having two to six carbon atoms, an alkynylsulfonyl group having two to six carbon atoms, an alkylsulfinyl group having one to six carbon atoms, an alkenylsulfinyl group having two to six carbon atoms or an alkynylsulfinyl group having two to six carbon atoms, such as methylsulfonyl group, ethylsulfonyl group, n-propylsulfonyl group, iso-propylsulfonyl group, n-butylsulfonyl group, t-butylsulfonyl group, vinylsulfonyl group, allylsulfonyl group, iso-propenylsulfonyl group, iso-pentenylsulfonyl group, ethynylsulfonyl group, methylsulfinyl group, ethylsulfinyl group, n-propylsulfinyl group, iso-propylsulfinyl group, n-butylsulfinyl group, t-butylsulfinyl group, vinylsulfinyl group, allylsulfinyl group, iso-propenylsulfinyl group, iso-pentenylsulfinyl group or ethynylsulfinyl group; a formyl group, a cycloalkyl group having three to eight carbon atoms such as cyclopropyl group, cyclobutyl group, cyclopentyl group, cyclohexyl group, cycloheptyl group or cyclooctyl group; a cycloalkenyl group having three to eight carbon atoms such as cyclopropenyl, cyclobutenyl, cyclopentenyl or cyclohexenyl group; a 5 to 14-membered non-aromatic heterocyclic group, such as pyrrolidinyl group, pyrrolyl group, piperidinyl group, piperazinyl group, imidazolyl group, pyrazolidyl group, imidazolidyl group, morpholinyl group, tetrahydrofuryl group, tetrahydropyranyl group, pyrrolinyl group, dihydrofuryl group, dihydropyranyl group, imidazolinyl group, oxazolinyl group, a group derived from pyridone ring, and a group derived from phthalimide ring or succinimide ring; an aromatic cyclic hydrocarbon group having six to fourteen carbon atoms such as phenyl group, indenyl group, 1-naphthyl group, 2-naphthyl group, biphenyl group or indacenyl group; a 5 to 14-membered aromatic heterocyclic group, such as pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolizinyl group, phthalazinyl group, naphthyridinyl group, quinoxalyl group, quinazolinyl group, cinnolinyl group, pteridinyl group, imidazotriazinyl group, pyrazinopyridazinyl group, acridinyl group, phenanthridinyl group, carbazolyl group, carbazolinyl group, perimidinyl group, phenanthrolinyl group, phenacynyl group, imidazopyridyl group, imidazopyrimidinyl group, pyrazolopyridyl group, pyrazolopyridyl group, thienyl group, benzothienyl group, furyl group, pyranyl group, cyclopentapyranyl group, benzofuryl group, isobenzofuryl group, thiazolyl group, isothiazolyl group, benzothiazolyl group, benzothiadiazolyl group, phenothiazinyl group, isoxazolyl group, furazanyl group, phenoxazinyl group, oxazolyl group, isoxazolyl group, benzoxazolyl group, oxadiazolyl group, pyrazolooxazolyl group, imidazothiazolyl group, thienofuranyl group, furopyrrolyl group or pyridooxazinyl group. Each of these substituents may be further substituted.

In the formula (I), suitable examples of the "substituents" in the "carbamoyl group which may be substituted" are groups selected from an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, an aromatic cyclic hydrocarbon group having six to fourteen carbon atoms which may be substituted, and a 5 to 14-membered aromatic heterocyclic group which may be substituted. The nitrogen atom of the carbamoyl group may be substituted with one or two groups selected from the above group of substituents. The substituents may be combined to form a 3 to 14-membered nitrogen-containing ring, such as pyrrolidyl group, pyrrolinyl group, piperidyl group, piperazinyl group, imidazolyl group, pyrazolidyl group, imidazolidyl group, morpholinyl group, tetrahydropyranyl group, aziridinyl group, oxiranyl group, oxathiolanyl group, phthalimidyl group, succinimidyl group, pyrrolyl group, pyridyl group, pyridazinyl group, pyrimidinyl group, pyrazinyl group or pyrazolyl group. In addition, the nitrogen-containing ring may be substituted.

In the formula (I), a preferred group in $R^1$ and/or $R^2$ is not specifically limited, of which a hydrogen atom, an alkyl group having one to six carbon atoms and an aliphatic acyl group having two to seven carbon atoms, each of which may be substituted, are more preferred, and a hydrogen atom is typically preferred.

In the formula (I), a preferred group in $R^3$ is not specifically limited, of which a hydrogen atom, an amino group, a cyano group, and an alkyl group having one to six carbon atoms, an alkoxy group having one to six carbon atoms, a phenyl group, a naphthyl group, a pyridyl group, a pyridazyl group, a pyrimidyl group, a pyrazyl group, a thienyl group, a furyl group, an imidazolyl group etc., each of which may be substituted are more preferred, and a hydrogen atom is further preferred.

In the formula (I), $R^4$ represents an aromatic cyclic hydrocarbon group having six to fourteen carbon atoms which may be substituted, a 5 to 14-membered non-aromatic heterocyclic group having one or more unsaturated bonds or a 5 to 14-membered aromatic heterocyclic group which may be substituted, and suitable examples thereof are an aromatic cyclic hydrocarbon group having six to fourteen carbon atoms such as phenyl group or naphthyl group; a 5 to 14-membered non-aromatic heterocyclic group, such as pyrrolidinyl group, pyrrolinyl group, piperidinyl group, piperazinyl group, imidazolinyl group, pyrazolidinyl group, imidazolidinyl group, morpholinyl group, tetrahydropyranyl group, aziridinyl group, oxiranyl group, oxathiolanyl group, 6-oxo-1,6-dihydropyridinyl group in which the nitrogen atom may be substituted or 2-oxo-1,2-dihydropyridinyl group in which the nitrogen atom may be substituted; or a 5 to 14-membered aromatic heterocyclic group, such as pyrrolyl group, pyridyl group, pyridazinyl group, pyrimidinyl group, pyrazinyl group, pyrazolyl group, imidazolyl group, indolyl group, isoindolyl group, indolizinyl group, quinolyl group, isoquinolyl group, quinolizinyl group, phthalazinyl group, naphthyridyl group, quinoxalyl group, quinazolyl group, imidazotriazinyl group, pyrazinopyridazinyl group, thienyl group, benzothienyl group, furyl group, pyranyl group, cyclopentapyranyl group, benzofuryl group, isobenzofuryl group, thiazolyl group, isothiazolyl group, benzothiazolyl group, benzothiadiazolyl group, phenothiazyl group, isoxazolyl group, pyrazolooxazolyl group, imidazothiazolyl group, thienofuryl group, furopyrrolyl group or pyridooxazinyl group. Each of these groups may be further substituted. More preferred examples of $R^4$ include groups represented by the formulae:

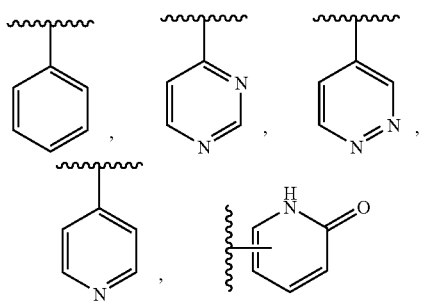

each of which may be substituted. When the 6-oxo-1,6-dihydropyridyl group or 2-oxo-1,2-dihydropyridyl group has a substituent, the substituent may also be combined with the nitrogen atom.

In the formula (I), $R^5$ refers to an aromatic cyclic hydrocarbon group having six to fourteen carbon atoms or a 5 to 14-membered aromatic heterocyclic group, each of which may be substituted, and suitable examples thereof include an aromatic cyclic hydrocarbon group having six to fourteen carbon atoms such as phenyl group or naphthyl group, or a 5 to 14-membered aromatic heterocyclic group, such as pyrrolyl group, pyridyl group, pyridazinyl group, pyrimidinyl group, pyrazinyl group, pyrazolyl group, imidazolyl group, indolyl group, isoindolyl group, indolizinyl group, quinolyl group, isoquinolyl group, quinolizinyl group, phthalazinyl group, naphthyridyl group, quinoxalyl group, quinazolyl group, imidazotriazinyl group, pyrazinopyridazinyl group, thienyl group, benzothienyl group, furyl group, pyranyl group, cyclopentapyranyl group, benzofuryl group, isobenzofuryl group, thiazolyl group, isothiazolyl group, benzothiazolyl group, benzothiadiazolyl group, phenothiazyl group, isoxazolyl group, pyrazolooxazolyl group, imidazothiazolyl group, thienofuryl group, furopyrrolyl group or pyridooxazinyl group. Each of these groups may be substituted. More preferred examples of $R^5$ include groups represented by the formulae:

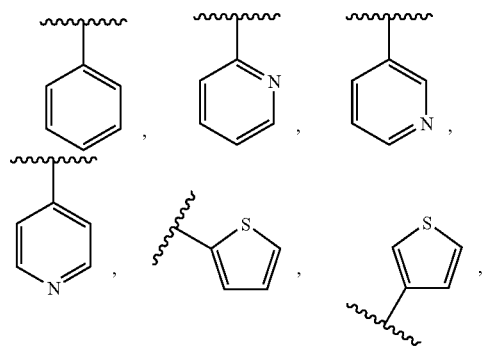

-continued

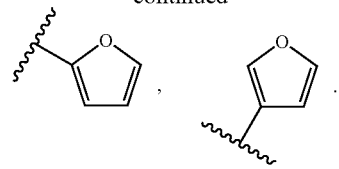

each of which may be substituted.

In the "substituents" in the "aromatic cyclic hydrocarbon group having six to fourteen carbon atoms which may be substituted" and the "5 to 14-membered aromatic heterocyclic group which may be substituted" in $R^3$, $R^4$ and $R^5$, (1) preferred examples are one or more groups selected from a hydroxyl group, a halogen atom, a cyano group, a nitro group, an alkyl group having one to six carbon atoms which may be substituted, an alkenyl group having two to six carbon atoms which may be substituted, an alkynyl group having two to six carbon atoms which may be substituted, an alkoxy group having one to six carbon atoms which may be substituted, an alkenyloxy group having two to six carbon atoms which may be substituted, an alkylthio group having one to six carbon atoms which may be substituted, an alkenylthio group having two to six carbon atoms which may be substituted, an alkynylthio group having two to six carbon atoms which may be substituted, a substituted carbonyl group, an amino group which may be substituted, an alkylsulfonyl group having one to six carbon atoms which may be substituted, an alkenylsulfonyl group having two to six carbon atoms which may be substituted, an alkynylsulfonyl group having two to six carbon atoms which may be substituted, an alkylsulfinyl group having one to six carbon atoms which may be substituted, an alkenylsulfinyl group having two to six carbon atoms which may be substituted, an alkynylsulfinyl group having two to six carbon atoms which may be substituted, a formyl group, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic cyclic hydrocarbon group having six to fourteen carbon atoms which may be substituted and a 5 to 14-membered aromatic heterocyclic group which may be substituted; (2) more preferably, one or more groups selected from (1) a hydroxyl group, (2) a halogen atom, (3) a cyano group, (4) a nitro group, (5) an alkyl group having one to six carbon atoms, an alkenyl group having two to six carbon atoms or an alkynyl group having two to six carbon atoms, each of which may be substituted with one or more groups selected from (i) a hydroxyl group, (ii) a cyano group, (iii) a halogen atom, (iv) an alkylamino group having one to six carbon atoms, (v) a di($C_{1-6}$ alkyl)amino group, (vi) a $C_{2-6}$ alkenylamino group, (vii) a di($C_{2-6}$ alkenyl)amino group, (viii) an alkynylamino group having two to six carbon atoms, (ix) a di($C_{2-6}$ alkynyl) amino group, (x) an N—$C_{1-6}$ alkyl-N—$C_{2-6}$ alkenylamino group, (xi) an N—$C_{1-6}$ alkyl-N—$C_{2-6}$ alkynylamino group, (xii) an N—$C_{2-6}$ alkenyl-N—$C_{2-6}$ alkynylamino group, (xiii) an aralkyloxy group, (xiv) a t-butyldimethylsilyloxy (TB-DMS-oxy) group, (xv) a $C_{1-6}$ alkylsulfonylamino group, (xvi) a $C_{1-6}$ alkylcarbonyloxy group, (xvii) a $C_{2-6}$ alkenylcarbonyloxy group, (xviii) a $C_{2-6}$ alkynylcarbonyloxy group, (xix) an N—$C_{1-6}$ alkylcarbamoyl group, (xx) an N—$C_{2-6}$ alkenylcarbamoyl group and (xxi) an N—$C_{1-6}$ alkynylcarbamoyl group, (6) an alkoxy group having one to six carbon atoms, an alkenyloxy group having two to six carbon atoms or an alkynyloxy group having two to six carbon atoms, each of which may be substituted with one or more groups selected from (i) an alkylamino group having one to six carbon atoms, (ii) an aralkyloxy group and (iii) a hydroxyl group, (7) an alkylthio group having one to six carbon atoms, an alkenylthio group having two to six carbon atoms or an alkynylthio group having two to six carbon atoms, each of which may be substituted with one or more groups selected from (i) a hydroxyl group, (ii) a nitrile group, (iii) a halogen atom, (iv) an alkylamino group having one to six carbon atoms, (v) an aralkyloxy group, (vi) a TBDMS-oxy group, (vii) a $C_{1-6}$ alkylsulfonylamino group, (viii) a $C_{1-6}$ alkylcarbonyloxy group and (ix) a $C_{1-6}$ alkylcarbamoyl group, (8) carbonyl group substituted with a group selected from (i) an alkoxy group having one to six carbon atoms, (ii) an amino group, (iii) an alkylamino group having one to six carbon atoms, (iv) a di ($C_{1-6}$ alkyl)amino group, (v) an alkenylamino group having two to six carbon atoms, (vi) a di($C_{2-6}$ alkenyl)amino group, (vii) an alkynylamino group having two to six carbon atoms, (viii) a di($C_{2-6}$ alkynyl)amino group, (ix) an N—$C_{1-6}$ alkyl-N—$C_{1-6}$ alkenylamino group, (x) an N—$C_{1-6}$ alkyl-N—$C_{2-6}$ alkynylamino group and (xi) an N—$C_{2-6}$ alkenyl-N—$C_{2-6}$ alkynylamino group, (9) an amino group which may be substituted with one or two groups selected from (i) an alkyl group having one to six carbon atoms, (ii) an alkenyl group having two to six carbon atoms, (iii) an alkynyl group having two to six carbon atoms, (iv) an alkylsulfonyl group having one to six carbon atoms, (v) an alkenylsulfonyl group having two to six carbon atoms, (vi) an alkynylsulfonyl group having two to six carbon atoms, (vii) a $C_{1-6}$ alkylcarbonyl group, (viii) a $C_{2-6}$ alkenylcarbonyl group and (ix) a $C_{2-6}$ alkynylcarbonyl group, (10) an alkylsulfonyl group having one to six carbon atoms, (11) an alkenylsulfonyl group having two to six carbon atoms, (12) an alkynylsulfonyl group having two to six carbon atoms, (13) an alkylsulfinyl group having one to six carbon atoms, (14) an alkenylsulfinyl group having two to six carbon atoms, (15) an alkynylsulfinyl group having two to six carbon atoms, (16) a formyl group, (17) a cycloalkyl group having three to eight carbon atoms or cycloalkenyl group having three to eight carbon atoms, each of which may be substituted with one or more groups selected from (i) a hydroxyl group, (ii) a halogen atom, (iii) a nitrile group, (iv) an alkyl group having one to six carbon atoms, (v) an alkoxy group having one to six carbon atoms, (vi) a $C_{1-6}$ alkoxy-$C_{1-6}$ alkyl group and (vii) an aralkyl group, (18) a 5 to 14-membered non-aromatic heterocyclic group which may be substituted with one or more groups selected from (i) a hydroxyl group, (ii) a halogen atom, (iii) a nitrile group, (iv) an alkyl group having one to six carbon atoms, (v) an alkoxy group having one to six carbon atoms, (vi) a $C_{1-6}$ alkoxy-$C_{1-6}$ alkyl group and (vii) an aralkyl group, (19) an aromatic cyclic hydrocarbon group having six to fourteen carbon atoms which may be substituted with one or more groups selected from (i) a hydroxyl group, (ii) a halogen atom, (iii) a nitrile group, (iv) an alkyl group having one to six carbon atoms, (v) an alkoxy group having one to six carbon atoms, (vi) a $C_{1-6}$ alkoxy-$C_{1-6}$ alkyl group and (vii) an aralkyl group, and (20) a 5 to 14-membered aromatic heterocyclic group which may be substituted with one or more groups selected from (i) a hydroxyl group, (ii) a halogen atom, (iii) a nitrile group, (iv) an alkyl group having one to six carbon atoms, (v) an alkoxy group having one to six carbon atoms, (vi) a $C_{1-6}$ alkoxy-$C_{1-6}$ alkyl group and (vii) an aralkyl group; and (3) most preferably, one or more groups selected from a hydroxyl group, a halogen atom (e.g., fluorine atom, chlorine atom, bromine atom or iodine atom), a cyano group, a nitro group, an alkyl group having one to six carbon atoms (e.g., methyl group, ethyl group, n-propyl group, iso-propyl group, n-butyl group, iso-butyl group, t-butyl group, n-pentyl group, i-pentyl group, neopentyl group or n-hexyl group), an alkenyl group having two to six carbon atoms (e.g., vinyl group, allyl group, 1-propenyl group or isopropenyl group), an alkynyl group having two to six carbon atoms (e.g., ethynyl group, 1-propynyl group, 2-propynyl group, butynyl group, pentynyl group or hexynyl group), an alkoxy group having one to six carbon atoms (e.g., methoxy group, ethoxy group, n-propoxy group, iso-propoxy group or n-butoxy group) and an alkenyloxy group having two to six carbon atoms (e.g., vinyloxy group, allyloxy group, 1-propenyloxy group or isopropenyloxy group)

Preferred embodiments of the compound represented by the formula (I) according to the present invention, a salt thereof or a solvate of them are not specifically limited, of which more preferred embodiments are compounds wherein $R^4$ is a 6-oxo-1,6-dihydropyridinyl group or a 2-oxo-1,2-dihydropyridinyl group represented by the formula:

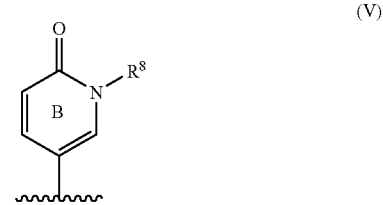

(V)

or the formula:

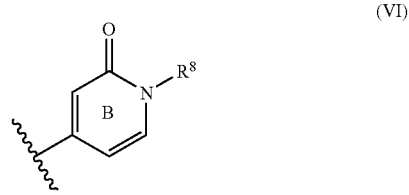

(VI)

(wherein, $R^8$ represents a group selected from the above-mentioned substituent group a, and the ring B represents a nitrogen-containing 6-membered ring which may be substituted with one to four groups selected from the above-mentioned substituent group a) or a 4-pyridyl group which may have one or two substituents; or salts thereof or solvates of that. The preferred embodiments of $R^8$ are those mentioned above.

The "salt" used in the present description is a salt formed from the compound according to the present invention, of which a pharmacologically acceptable salt is preferred. Preferred examples thereof are a hydrohalogenic acid salt such as hydrofluoride, hydrochloride, hydrobromide or hydroiodide; an inorganic acid salt such as sulfate, nitrate, perchlorate, phosphate, carbonates or hydrogencarbonate; an organic carboxylic acid salt such as acetate, trifluoroacetate, oxalate, maleate, tartrate, fumarate or citrate; an organic sulfonic acid salt such as methanesulfonate, trifluoromethanesulfonate, ethanesulfonate, benzenesulfonate, toluenesulfonate or camphorsulfonate; an amino acid salt such as aspartate or glutamate; a quaternary amine salt; an alkali metal salt such as sodium salt or potassium salt; an alkaline earth metal salt such as magnesium salt or calcium salt. More preferred examples of the "pharmacologically acceptable salt" are hydrochloride and oxalate.

The "solvate" used in the present description is a solvate of the compound according to the present invention or a salt thereof and is not specifically limited. Preferably, the solvate is a hydrate, a solvate with an alcohol such as methanol, ethanol, propanol, or isopropanol, a solvate with an ester such as ethyl acetate, a solvate with an ether such as methyl ether, ethyl ether or THF (tetrahydrofuran) or a solvate with DMF (dimethylformamide), of which a hydrate or a solvate with an alcohol such as methanol or ethanol is more preferred. A solvent for constituting the solvate is preferably a pharmacologically acceptable solvent.

Production Process

Typical production processes for the compounds represented by the formula (I) according to the present invention will be illustrated be low. The "room temperature" as used hereinafter represents a temperature from about 0° C. to about 40° C.

(Production Process A)

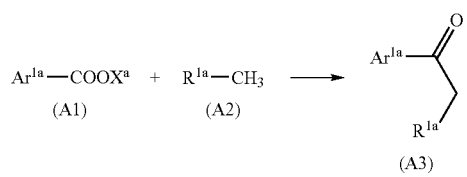

In the above formulae, $Ar^{1a}$ represents an aromatic hydrocarbon cyclic group having six to fourteen carbon atoms which may be substituted or a 5 to 14-membered aromatic heterocyclic group which may be substituted; $X^a$ represents an alkyl group having one to six carbon atoms; and $R^{1a}$ represents a 5 to 14-membered aromatic heterocyclic group having a nitrogen atom at 4-position thereof and which may be substituted (such as a 4-pyridyl group, a 4-pyrimidinyl group or a 4-pyridazinyl group). The compound (A3), which is provided as a raw material for the production of the compound represented by the above formula (I) of the present invention, can be produced through dealcoholization-condensation by reacting an aromatic carboxylate (A1) with a 4-methyl aromatic heterocyclic compound (A2) represented by the formula of $R^{1a}$-$CH_3$ in a solvent in the presence of a base. The base used varies depending on the starting materials, solvent used, and so on in the production. Preferable bases include secondary amine metal salts such as lithium bis(trimethylsilyl)amide and lithium diisopropylamide although not specifically limited to as far as the reaction is not inhibited. The solvent used varies depending on, for example, the starting materials and reagents used. Preferable solvents include ethers such as tetrahydrofuran, dioxane, 1,2-dimethoxyethane and diethylene glycol, although not particularly limited insofar as the reaction is not inhibited and the starting materials are dissolved to a certain degree. The reaction temperature is generally –78° C. to room temperature, preferably around 0° C.

(Production Process B)

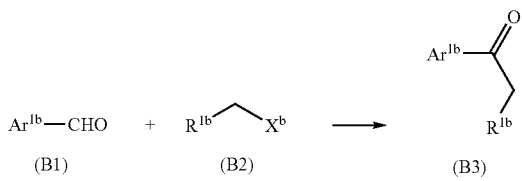

In the above formulae, $Ar^{1b}$ and $R^{1b}$ are the same as or different from each other and each represents an aromatic hydrocarbon cyclic group having six to fourteen carbon atoms which may be substituted or a 5 to 14-membered aromatic heterocyclic group which may be substituted; and $X^b$ represents a halogen atom, an alkylsulfonyloxy group or an arylsulfonyloxy group. The compound (B3), which is provided as a raw material for the production of the compound represented by the above formula (I) of the present invention, can be produced by this Production Process B instead of Production Process A. That is, the compound (B3) is produced by the condensation between an aromatic trialkylsilyl cyanohydrin compound prepared from an aromatic aldehyde (B1) and the compound (B2) represented by the formula of $R^{1b}$—$CH_2X^b$ in the presence of a base, followed by reacting with a fluorine compound to cause de(trialkylsilyl)cyanidation. As an agent for preparing an aromatic trialkylsilyl cyanohydrin from the compound (B1), a trialkylsilyl cyanide compound such as trimethylsilyl cyanide, is preferably used. At this time, it is also preferable to use a metal salt such as zinc (II) iodide as a catalyst, allowing the reaction to proceed quickly. The base used varies depending on the starting materials, solvent used, and so on. Preferable bases include secondary amine metal salts such as lithium bis(trimethylsilyl)amide or lithium diisopropylamide although not specifically limited to as far as the reaction is not inhibited. The fluorine compound used varies depending on the starting materials, solvents used, and so on. Preferable fluorine compounds include hydrofluoric acid and hydrofluoride of amine, more preferably tetrabutylammonium fluoride although not specifically limited to as far as the reaction is not inhibited. The solvent used varies depending on the starting materials, reagents, and so on. Preferable examples of the solvent used, although not specifically limited to as far as the starting materials are dissolved to a certain degree, include ethers such as tetrahydrofuran, dioxane, 1,2-dimethoxyethane or diethylene glycol. The reaction temperature is preferably –78° C. to room temperature.

(Production Process C)

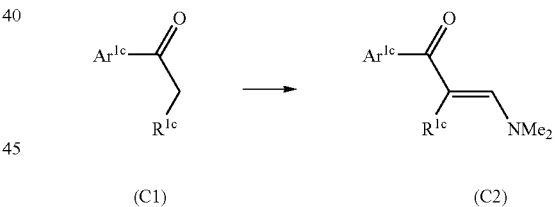

In the above formulae, $Ar^{1c}$ and $R^{1c}$ are the same as or different from each other and each represents an aromatic hydrocarbon cyclic group having six to fourteen carbon atoms which may be substituted or a 5 to 14-membered aromatic heterocyclic group which may be substituted. 3-(Dimethylamino)-2-propen-1-one derivative (C2) is a raw material for the production of the compound (I) of the present invention. The compound (C2) can be produced by allowing N,N-dimethylformamide dimethylacetal to act on active methylene of the compound (C1) produced in Production Process A or B. Most preferable is to perform this reaction without any solvent. However, a preferable result can be obtained even though the compound (C1) is diluted with a solvent (such as N,N-dimethylformamide, tetrahydrofuran, dioxane, N-methylpyrrolidone, benzene or toluene) that dissolves the starting materials to a certain degree without inhibiting the reaction. The reaction temperature is generally room temperature to 120° C., preferably around 100° C.

(Production Process D)

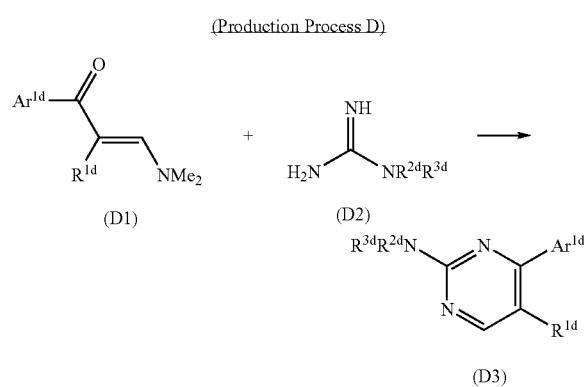

In the above formulae, $Ar^{1d}$ and $R^{1d}$ are the same as or different from each other and each represents an aromatic hydrocarbon cyclic group having six to fourteen carbon atoms which may be substituted or a 5 to 14-membered aromatic heterocyclic group which may be substituted; and $R^{2d}$ and $R^{3d}$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted or a 5 to 14-membered aromatic heterocyclic group which may be substituted. The compound (D3) of the present invention can be produced by allowing a guanidine derivative (D2) to react with 3-(dimethylamino)-2-propen-1-one derivative (D1) produced by Production Process C in the presence of a base. The guanidine derivative (D2) used may form a salt with an acid such as hydrochloric acid, hydrobromic acid, sulfuric acid or acetic acid. The base used varies depending on the starting materials, solvent used, and so on. Preferable examples of the base include an alkali metal carbonate such as potassium carbonate or sodium carbonate, or an alkali metal alkoxide such as sodium methoxide, sodium ethoxide or potassium t-butoxide although not specifically limited to as far as the reaction is not inhibited. The solvent used varies depending on the starting materials, reagents, and so on. Preferable examples of the solvent include N,N-dimethylformamide, N-methylpyrrolidone, dimethylsulfoxide and ethanol, although not specifically limited to as far as the reaction is not inhibited and the starting materials and bases are dissolved to a certain degree. The reaction temperature is preferably room temperature to 120° C., more preferably around 70° C.

-continued

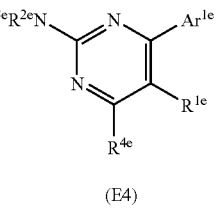

In the above formulae, $Ar^{1e}$, $R^{1e}$ and $R^{4e}$ are the same as or different from each other and each represents an aromatic hydrocarbon cyclic group having six to fourteen carbon atoms which may be substituted or a 5 to 14-membered aromatic heterocyclic group which may be substituted; and $R^{2e}$ and $R^{3e}$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted or a 5 to 14-membered aromatic heterocyclic group which may be substituted. The compound (E4) of the present invention can be produced by allowing an aldehyde (E2) and a guanidine derivative (E3) to react with the compound (E1) produced by the above Production Process A or B in the presence of the base, followed by aromatizing with an oxidant. The guanidine derivative (E3) used may form a salt with an acid such as hydrochloric acid, hydrobromic acid, sulfuric acid or acetic acid. The base used varies depending on the starting materials, solvent used, and so on. Preferably, although not specifically limited to as far as the reaction is not inhibited, the base used may be an alkali metal alkoxide such as sodium methoxide, sodium ethoxide or potassium t-butoxide, or alternatively an alkali metal carbonate such as potassium carbonate or sodium carbonate. Examples of oxidant used include manganese compounds such as active manganese dioxide, quinones such as 2,3-dichloro-5,6-dicyano-1,4-benzoquinone, and sulfur. The solvent used is not specifically limited to as far as the reaction is not inhibited and the starting materials and intermediates are dissolved to a certain degree. Examples of the solvents may include ethanol, methanol, tetrahydrofuran, dichloromethane, dichloroethane, chloroform, N,N-dimethylformamide, N-methylpyrrolidone, dimethylsulfoxide, and mixed solvents thereof. The reaction temperature is preferably 0° C. to 120° C.

(Production Process E)

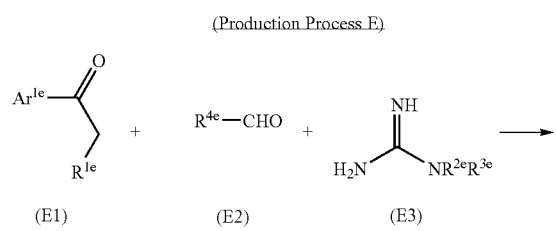

(Production Process F)

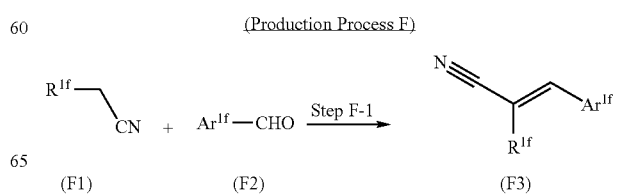

-continued

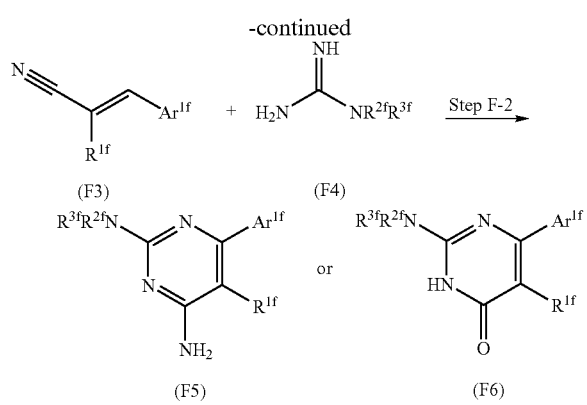

(F3)  (F4)  (F5)  (F6)

In the above formulae, $Ar^{1f}$ and $R^{1f}$ are the same as or different from each other and each represents an aromatic hydrocarbon cyclic group having six to fourteen carbon atoms which may be substituted or a 5 to 14-membered aromatic heterocyclic group which may be substituted; and $R^{2f}$ and $R^{3f}$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted or a 5 to 14-membered aromatic heterocyclic group which may be substituted. The compound (F5) of the present invention and the compound (F6), which is provided as a raw material for the production of the compound (I) of the present invention, can be produced by Steps F-1 and F-2 in Production Process F.

Step F-1: This step is to produce the compound (F3) by dehydration-condensation between the compound (F1) and the aldehyde compound (F2) in the presence of a base. Preferable examples of the base used in the reaction include alkali metal alkoxides such as sodium methoxide, sodium ethoxide or potassium t-butoxide. Alternatively, alkali metal carbonates such as potassium carbonate or sodium carbonate may be used. The reaction is carried out in a solvent which is not specifically limited to as far as the reaction is not inhibited and the starting materials and intermediates are dissolved to a certain degree. The solvents may include ethanol, methanol, tetrahydrofuran, dichloromethane, chloroform, N,N-dimethylformamide, N-methylpyrrolidone, dimethylsulfoxide, and mixed solvents thereof. The reaction is carried out at a temperature of 0° C. to 120° C.

Step F-2: This step is to produce the pyrimidine derivative (F5) by reacting the compound (F3) obtained in Step F-1 with the guanidine derivative (F4) in the presence of the base, followed by aromatizing with an oxidant. The guanidine derivative (F4) used may form a salt with an acid such as hydrochloric acid, hydrobromic acid, sulfuric acid or acetic acid. Preferable examples of the base used in the reaction include alkali metal alkoxides such as sodium methoxide, sodium ethoxide or potassium t-butoxide. Alternatively, alkali metal carbonates such as potassium carbonate or sodium carbonate may be used. Examples of the oxidant used in the reaction include manganese compounds such as active manganese dioxide, quinones such as 2,3-dichloro-5,6-dicyanao-1,4-benzoquinone, and sulfur. The reaction is carried out in a solvent which is not specifically limited to as far as the reaction is not inhibited and the starting materials and intermediates are dissolved to a certain degree. The solvents may include ethanol, methanol, tetrahydrofuran, dichloromethane, chloroform, N,N-dimethylformamide, N-methylpyrrolidone, dimethylsulfoxide, and mixed solvents thereof. The reaction temperature is 0° C. to 120° C. Alternatively, in Step F-1, even if the guanidine derivative (F4) is provided in the reaction mixture from the be ginning of the reaction, followed by the aromatization with the oxidant, the pyrimidine derivative (5) can be produced without isolating the compound (F3). Furthermore, in step F-2, the reaction between the compound (F3) and the guanidine derivative (F4) in the presence of a base, the reaction (under heating) was carried out for a long period of two to seven days under moisture conditions, followed by an oxidative reaction, to give the pyrimidinone derivative (F6).

(Production Process G)

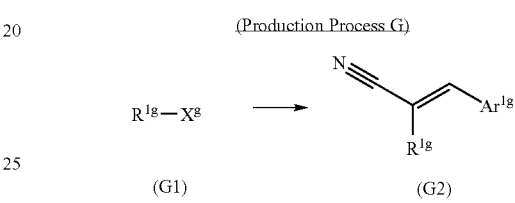

(G1)  (G2)

In the above formulae, $Ar^{1g}$ and $R^{1g}$ are the same as or different from each other, and each represents an aromatic hydrocarbon cyclic group having six to fourteen carbon atoms which may be substituted or a 5 to 14-membered aromatic heterocyclic group which may be substituted; and $X^g$ represents a halogen atom, an alkylsulfonyloxy group or an arylsulfonyloxy group. The present production method is an alternative method for the synthesis of the compound (F3) in Production Process F described above. That is, the method includes the step of allowing cyanomethylphosphonic acid diester to react with the compound (G1) in the presence of a base and a palladium catalyst, followed by dephosphorylation-condensation with an aldehyde compound represented by the formula of $Ar^{1g}$—CHO to produce a compound (G2). The base used in the reaction is preferably sodium hydride, and the palladium catalyst used is preferably tetrakis(triphenylphosphine)palladium (O), respectively. Preferably, the reaction solvents include ethers such as dimethoxyethane, diethyl ether or tetrahydrofuran. The reaction is carried out at a temperature of 0° C. to 120° C.

(Production Process H)

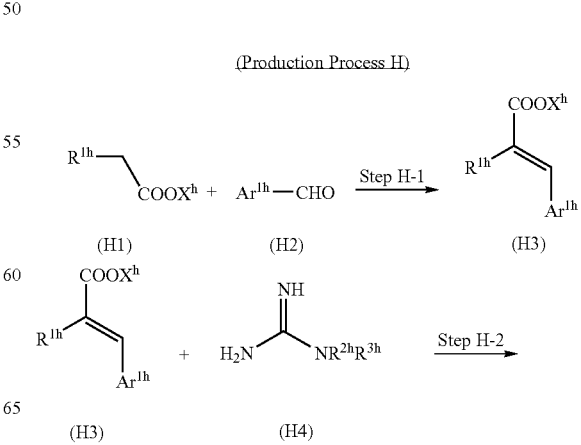

(H1)  (H2)  (H3)

(H3)  (H4)

-continued

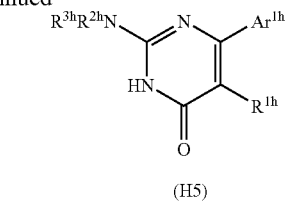

(H5)

In the above formulae, $Ar^{1h}$ and $R^{1h}$ are the same as or different from each other and each represents an aromatic hydrocarbon cyclic group having six to fourteen carbon atoms which may be substituted or a 5 to 14-membered aromatic heterocyclic group which may be substituted; $R^2h$ and $R^3h$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted or a 5 to 14-membered aromatic heterocyclic group which may be substituted; and $X^h$ represents an alkyl group having one to six carbon atoms. The present production method is another synthetic method for the compound (F6) in Production Process F.

Step H-1: This step is to produce the compound (H3) by dehydration-condensation between the compound (H1) and the compound (H2) using carboxylic anhydride in the presence of a base. Examples of the base used in the reaction include amines such as triethylamine, pyrrolidine, piperidine or diisopropylethylamine. The carboxylic anhydride is preferably acetic anhydride. The reaction is carried out at room temperature to 120° C.

Step H-2: This step is to produce the pyrimidinone derivative (H5) as a raw material for the production of the compound represented by the above formula (I) of the present invention, by reacting the compound (H3) obtained in Step H-1 with the guanidine derivative (H4) in the presence of a base, followed by aromatization with an oxidant. The guanidine derivative (H4) to be used may form a salt with an acid such as hydrochloric acid, hydrobromic acid, sulfuric acid or acetic acid. Preferable examples of the base to be used in the reaction include alkali metal alkoxides such as sodium methoxide, sodium ethoxide or potassium t-butoxide. Alternatively, an alkali metal carbonate such as potassium carbonate or sodium carbonate may be used. Examples of the oxidant to be used in the reaction include manganese compounds such as active manganese dioxide; quinones such as 2,3-dichloro-5,6-dicyanao-1,4-benzoquinone; and sulfur. The reaction is carried out in a solvent which does not inhibit the reaction and which dissolves the starting materials and intermediates to a certain degree. Examples of the solvents include ethanol, methanol, tetrahydrofuran, dichloromethane, chloroform, N,N-dimethylformamide, N-methylpyrrolidone, dimethylsulfoxide, and mixed solvents thereof. The reaction is performed in temperatures of 0° C. to 120° C.

(Production Process I)

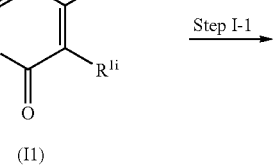

(I1)

Step I-1

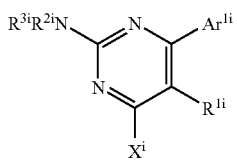

(I2)

Step I-2

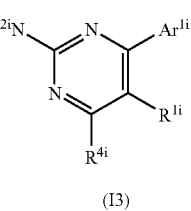

(I3)

In the above formulae, $Ar^{1i}$ and $R^{1i}$ are the same as or different from each other and each represents an aromatic hydrocarbon cyclic group having six to fourteen carbon atoms which may be substituted or a 5 to 14-membered aromatic heterocyclic group which may be substituted; $R^{2i}$ and $R^{3i}$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted or a 5 to 14-membered aromatic heterocyclic group which may be substituted; $R^{4i}$ represents an oxygen atom which may be substituted; and $X^i$ represents a halogen atom. The compounds (I2) and (I3) of the present invention can be produced by Production Process I.

Step I-1: This step is to produce a 4-halogenopyrimidine derivative (I2) of the present invention from the pyrimidinone derivative (I1) obtained in Production Process F or H by converting the oxo group of the pyrimidinone derivative (I1) into a halogen atom. The reaction is carried out in the absence of a solvent or in a suspension with a solvent such as acetonitrile, dioxane or tetrahydrofuran by allowing a halogenating agent such as phosphorous oxychloride or, phosphorous oxybromide at a temperature of 70° C. to 120° C. The reaction can be accelerated by the addition of a tertiary amine such as dimethylaniline, diisopropylethylamine or tripropylamine; a quaternary ammonium salt such as tetraethylammonium chloride; or N,N-dimethylformamide.

Step I-2: This step is to produce a 4-alkoxypyrimidine derivative (I3) of the present invention from the 4-halogenopyrimidine derivative (I2) obtained in Step I-1 described above by allowing an alkali metal alkoxide to act on the 4-chloropyrimidine derivative to convert the halogen atom at position 4 thereof into an alkoxy group. The alkali metal alkoxide can be prepared by allowing a base or an alkali metal to act on an alcohol in a solvent or in the absence of the solvent. The alkali metal used is preferably sodium or potassium. The base used in the reaction varies depending on the starting materials, solvents used, and so on. Preferable bases include alkali metal hydride such as sodium hydride and so on, although not specifically limited to as far as the reaction is not inhibited. Alternatively alkali metal alkoxides such as sodium methoxide, sodium ethoxide or potassium t-butoxide may be used. The solvent used varies depending on the starting materials, reagents, and so on. Preferably, although not specifically limited to as far as the reaction is not inhibited and the starting materials and bases are dissolved to a certain degree, examples of the solvents include N,N-dimethylformamide, N-methylpyrrolidone, dimethylsulfoxide, alcohols such as methanol or ethanol; ethers such as tetrahydrofuran or 1,4-dioxane; and mixed solvents thereof. The reaction temperature is preferably room temperature to 120° C.

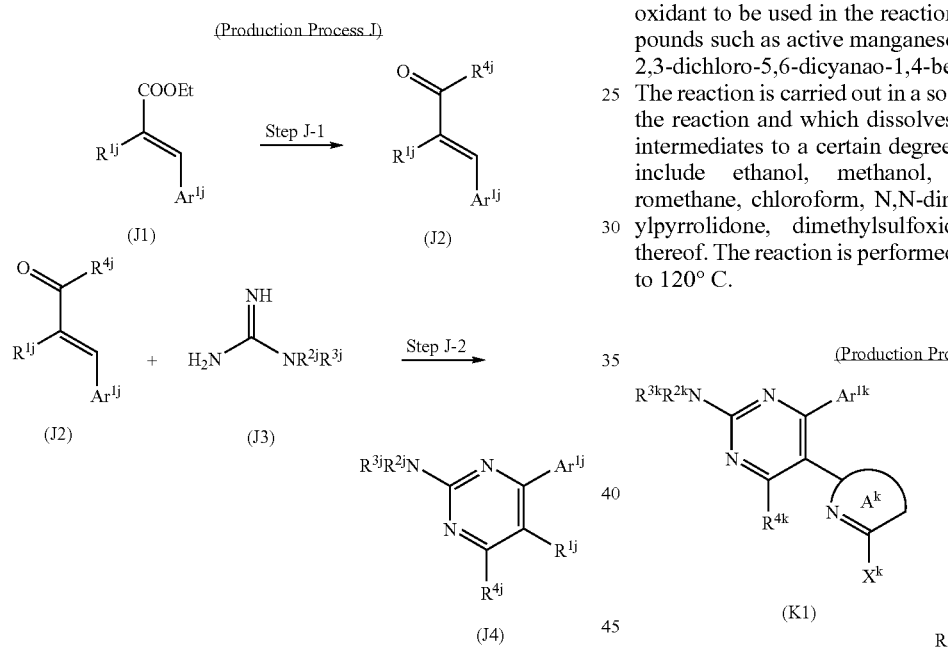

In the above formulae, $Ar^{1j}$ and $R^{1j}$ are the same as or different from each other and each represents an aromatic hydrocarbon cyclic group having six to fourteen carbon atoms which may be substituted or a 5 to 14-membered aromatic heterocyclic group which may be substituted; $R^{2j}$ and $R^{3j}$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted or a 5 to 14-membered aromatic heterocyclic group which may be substituted; and $R^{4j}$ represents an alkyl group which may be substituted. The compounds (J4) of the present invention can be produced by Production Process J.

Step J-1: This step is to produce the compound (J2) by allowing a Grignard reagent to react with the compound (J1) obtained in Step H-1 of the Production Process H described above. The reaction is carried out in a solvent which does not inhibit the reaction and dissolves the starting materials and intermediates to a certain degree. The solvents may include ethers such as tetrahydrofuran, diethyl ether or dimethoxyethane. The reaction temperature is −78° C. to room temperature.

Step J-2: This step is to produce the pyrimidine derivative (J4) of the present invention by reacting the compound (J2) obtained in Step J-1 with the guanidine derivative (J3) in the presence of a base, followed by aromatization with an oxidant. The guanidine derivative (J3) to be used may form a salt with an acid such as hydrochloric acid, hydrobromic acid, sulfuric acid or acetic acid. Preferable examples of the base to be used in the reaction include alkali metal alkoxides such as sodium methoxide, sodium ethoxide or potassium t-butoxide. Alternatively, an alkali metal carbonate such as potassium carbonate or sodium carbonate may be used. Examples of the oxidant to be used in the reaction include: manganese compounds such as active manganese dioxide; quinones such as 2,3-dichloro-5,6-dicyanao-1,4-benzoquinone; and sulfur. The reaction is carried out in a solvent which does not inhibit the reaction and which dissolves the starting materials and intermediates to a certain degree. Examples of the solvents include ethanol, methanol, tetrahydrofuran, dichloromethane, chloroform, N,N-dimethylformamide, N-methylpyrrolidone, dimethylsulfoxide, and mixed solvents thereof. The reaction is performed in the temperature of 0° C. to 120° C.

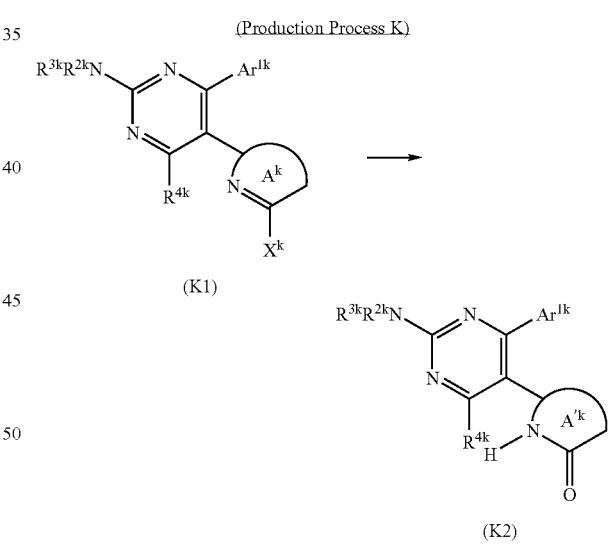

In the above formulae, $Ar^{1k}$ represents an aromatic hydrocarbon cyclic group having six to fourteen carbon atoms which may be substituted or a 5 to 14-membered aromatic heterocyclic group which may be substituted; $R^{2k}$ and $R^{3k}$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted or a 5 to 14-membered aromatic heterocyclic group which may be substituted; $R^{4k}$ represents a hydrogen atom, a cyano group, an alkyl group having one to six carbonatoms which may be substituted, an alkenyl group having two to six carbon atoms which may be substituted, an alkynyl group having two to six carbon atoms which may be substituted, an aromatic hydrocarbon cyclic group having six to fourteen carbon atoms which may be substituted, a 5 to 14-membered aromatic heterocyclic group which may be substituted, a nitrogen atom which may be substituted, an oxygen atom which may be substituted or a sulfur atom which may be substituted; the ring $A^k$ represents a pyridyl group, a pyrimidinyl group, a pyrazinyl group or a pyridazinyl group; the ring $A'^k$ represents a dihydrooxopyridinyl group, a dihydrooxopyrimidinyl group, a dihydrooxopyrazinyl group or a dihydrooxopyridazinyl group; and $X^k$ represents a halogen atom. This step is to produce the 5-(α-oxo nitrogen-containing heterocyclyl)pyrimidine (K2) of the present invention by converting halogen atom ($X^k$) in 5-(α-halogeno nitrogen-containing heteroaryl)pyrimidine (K1) into 4-methoxybenzyloxy group while substituting the halogen atom ($X^k$) of 5-(α-halogeno nitrogen-containing heteroaryl)pyrimidine (K1) with 4-methoxybenzylalkoxide, followed by treatment with an acid. The 4-methoxybenzylalkoxide is prepared using an alkali metal such as sodium or potassium or a base such as sodium hydride in the absence of a solvent or by dilution with a solvent such as N,N-dimethylformamide or dimethylsulfoxide at a temperature of room temperature to 120° C. The acid used in the reaction may be trifluoroacetic acid, hydrochloric acid, bromic acid, or the like. The reaction is carried out in the absence of a solvent or by dilution with a solvent such as dichloromethane, dichloroethane or tetrahydrofuran at a temperature of room temperature to 150° C.

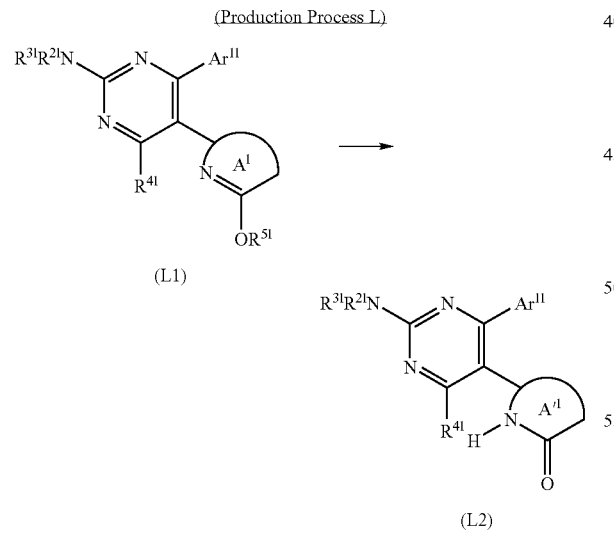

(Production Process L)

(L1)

(L2)

In the above formulae, $Ar^{1l}$ represents an aromatic hydrocarbon cyclic group having six to fourteen carbon atoms which may be substituted or a 5 to 14-membered aromatic heterocyclic group which may be substituted; $R^{2l}$ and $R^{3l}$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted or a 5 to 14-membered aromatic heterocyclic group which may be substituted; $R^{4l}$ represents a hydrogen atom, a cyano group, an alkyl group having one six carbon atoms which may be substituted, an alkenyl group having two to six carbon atoms which may be substituted, an alkynyl group having two to six carbon atoms which may be substituted, an aromatic hydrocarbon cyclic group having six to fourteen carbon atoms which may be substituted, a 5 to 14-membered aromatic heterocyclic group which may be substituted, a nitrogen atom which may be substituted, an oxygen atom which may be substituted or a sulfur atom which may be substituted; $R^{51}$ represents an alkyl group having one to six carbon atoms which may be substituted; the ring $A^l$ represents a pyridyl group, a pyrimidinyl group, a pyrazinyl group or a pyridazinyl group; and the ring $A'^l$ represents a dihydrooxopyridinyl group, a dihydrooxopyrimidinyl group, a dihydrooxopyrazinyl group or a dihydrooxopyridazinyl group. This step is to produce the 5-(α-oxo nitrogen-containing heterocyclyl)pyrimidine (L2) of the present invention by hydrolyzing the alkyl group of 5-(α-alkoxy nitrogen-containing heteroaryl)pyrimidine (L1). The reaction is carried out in an aqueous solution of a mineral acid such as hydrochloric acid, hydrobromic acid or sulfuric acid, or in a mixed solvent of water with acetic acid or the like at a temperature of room temperature to 120° C.

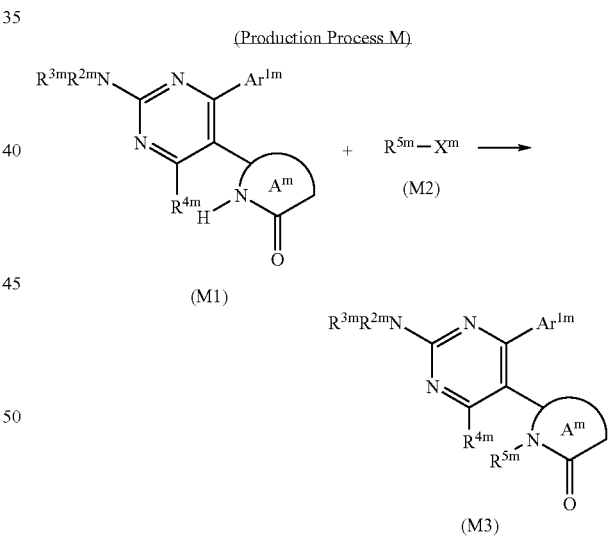

(Production Process M)

(M1)

(M3)

In the above formulae, $Ar^{1m}$ represents an aromatic hydrocarbon cyclic group having six to fourteen carbon atoms which may be substituted or a 5 to 14-membered aromatic heterocyclic group which may be substituted; $R^{2m}$ and $R^{3m}$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted or a 5 to 14-membered aromatic heterocyclic group which may be substituted; $R^{4m}$ represents a hydrogen atom, a cyano group, an alkyl group having one to six carbon atoms which may be substituted, an alkenyl group having two to six carbon atoms which may be substituted, an alkynyl group having two to six carbon atoms which may be substituted, an aromatic hydrocarbon cyclic group having six to fourteen carbon atoms which may be substituted, a 5 to 14-membered aromatic heterocyclic group which may be substituted, a nitrogen atom which may be substituted, an oxygen atom which may be substituted or a sulfur atom which may be substituted; $R^{5m}$ represents an alkyl group which may be substituted, an alkenyl group which may be substituted or an alkynyl group which may be substituted; and the ring $A^m$ represents a dihydrooxopyridinyl group, a dihydrooxopyrimidinyl group, a dihydrooxopyrazinyl group or a dihydrooxopyridazinyl group. This step is to produce the compound (M3) of the present invention by introducing a substituent to the nitrogen atom on the ring $A^m$ of 5-(α-oxo nitrogen-containing heterocyclyl)pyrimidine (M1) The reaction is carried out through the reaction with a halogenated-alkyl compound or the like in a solvent in the presence of a base. The bases include sodiummethoxide, sodium ethoxide, potassium t-butoxide, sodium hydride, sodium hydroxide, potassium hydroxide, sodium bicarbonate, sodium carbonate and potassium carbonate. The solvents include alcohols such as methanol or ethanol, ethers such as tetrahydrofuran, dioxane, dimethoxyethane or diethylene glycol dimethyl ether, N,N-dimethylformamide, dimethylsulfoxide, N-methylpyrrolidone, and mixed solvents thereof. The reaction is carried out at a temperature of 0° C. to 100° C.

(Production Process N)

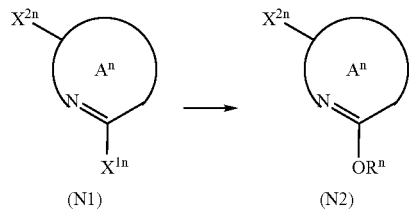

(N1)    (N2)

In the above formulae, $R^n$ represents an alkyl group having one to six carbon atoms which may be substituted; the ring $A^n$ represents a pyridyl group, a pyrimidinyl group, a pyrazinyl group or a pyridazinyl group; and $X^{1n}$ and $X^{2n}$ are the same as or different from each other and each represents a halogen atom. This step is to produce an α-alkoxy nitrogen-containing heteroaryl compound (N2) as a raw material for the production of the compound represented by the formula (I) of the present invention by allowing alkali metal alkoxide to react with an α-halogeno nitrogen-containing heteroaryl compound (N1) in a solvent. The alkali metal alkoxide is prepared by allowing an alkali metal or base to react with an alcohol in a solvent or in the absence of the solvent. Preferably, for example, the alkali metal used is sodium or potassium. The base used in the reaction varies depending on the starting materials, solvents used, and so on. Preferable bases include an alkali metal hydride such as sodium hydride, although not specifically limited to as far as the reaction is not inhibited. Alternatively, alkali metal alkoxides such as sodium methoxide, sodium ethoxide or potassium t-butoxide may be used.

The solvent used varies depending on the starting materials, reagents, and so on. Preferably, although not specifically limited to as far as the reaction is not inhibited and the starting materials and bases are dissolved to a certain degree, the solvents include alcohols such as N,N-dimethylformamide, N-methylpyrrolidone, dimethylsulfoxide, alcohols such as methanol or ethanol, ethers such as tetrahydrofuran or 1,4-dioxane, and mixed solvents thereof. The reaction temperature is preferably room temperature to 120° C.

(Production Process O)

(O1)    (O2)

In the above formulae, $R^{5o}$ represents an aromatic hydrocarbon cyclic group having six to fourteen carbon atoms which may be substituted or a 5 to 14-membered aromatic heterocyclic group which may be substituted; $X^o$ represents a halogen atom; and $Y^o$ represents an alkyl group having one to six carbon atoms. A tin reagent (O2) as a raw material for the production of the compound represented by the above formula (I) of the present invention can be produced by lithiating the compound (O1) and then allowing a halogenotrialkyltin to react with the lithiated compound. In the lithiation reaction, it is preferable to use alkyllithium such as n-butyllithium, s-butyllithium or t-butyllithium. The halogeno trialkyltin used varies depending on the starting materials, solvents used, and so on. Preferably, tributyltin chloride, trimethyltin chloride, triethyltin bromide, or the like may be proposed, although not specifically limited to as far as the reaction is not inhibited. The solvent used in the reaction varies depending on the starting materials, reagents, and so on. Preferably, the solvents include ethers such as tetrahydrofuran and diethyl ether, or hydrocarbons such as hexane and heptane, and mixed solvents thereof, although not specifically limited to as far as the reaction is not inhibited and the starting material is dissolved to a certain degree. The reaction temperature is preferably –100° C. to room temperature.

(Production Process P)

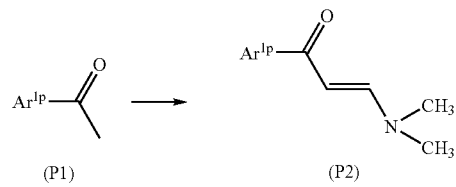

(P1)    (P2)

In the above formulae, $Ar^{1p}$ represents an aromatic hydrocarbon cyclic group having six to fourteen carbon atoms which may be substituted or a 5 to 14-membered aromatic heterocyclic group which may be substituted. A 3-(dimethylamino)-2-propen-1-one derivative (P2) as a raw material for the production of the compound represented by the above formula (I) of the present invention can be produced by allowing N,N-dimethylformamide dimethylacetal to react with the compound (P1). Most preferably, the reaction is carried out in the absence of a solvent. Alternatively, a preferable result can be also obtained by dilution with a solvent which dissolves starting materials to some degree without inhibiting the reaction (e.g., N,N-dimethylformamide, tetrahydrofuran, dioxane, N-methylpyrrolidone, benzene, or toluene). The reaction temperature is generally room temperature to 120° C., preferably around 100° C.

(Production Process Q)

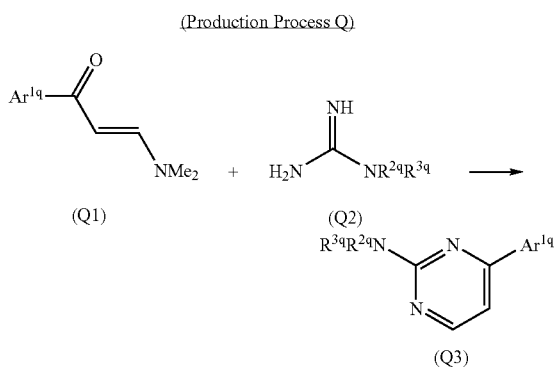

In the above formulae, $Ar^{1q}$ represents an aromatic hydrocarbon cyclic group having six to fourteen carbon atoms which may be substituted or a 5 to 14-membered aromatic heterocyclic group which may be substituted; and $R^{2q}$ and $R^{3q}$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted or a 5 to 14-membered aromatic heterocyclic group which may be substituted. This step is to produce a pyrimidine derivative (Q3) as a raw material for the production of the compound represented by the above formula (I) of the present invention by allowing a guanidine derivative (Q2) to react with the 3-(dimethylamino)-2-propen-1-one derivative (Q1) obtained from Production Process P described above. The guanidine derivative (Q2) used may form a salt with an acid such as hydrochloric acid, hydrobromic acid, sulfuric acid or acetic acid. The base used varies depending on the starting materials, solvents used, and so on. Preferably, although not specifically limited to as far as the reaction is not inhibited, the base is alkali metal carbonate such as potassium carbonate or sodium carbonate, or alternatively alkali metal alkoxide such as sodium methoxide, sodium ethoxide or potassium t-butoxide. The solvent used varies depending on the starting materials, reagents, and so on. Preferable examples of the solvent include N,N-dimethylformamide, N-methylpyrrolidone, dimethylsulfoxide and ethanol although not specifically limited to as far as the reaction is not inhibited and the starting materials and bases are dissolved to a certain degree. The reaction temperature is preferably room temperature to 120° C., more preferably around 100° C.

(Production Process R)

Ar$^{1r}$—C(=O)— + R$^{4r}$—CHO + H$_2$N—C(=NH)—NR$^{2r}$R$^{3r}$ ⟶

(R1)  (R2)  (R3)

-continued

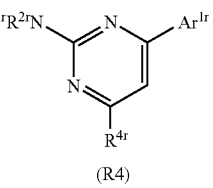

(R4)

In the above formulae, $A^{1r}$ and $R^{4r}$ are the same as or different from each other and each represents an aromatic hydrocarbon cyclic group having six to fourteen carbon atoms which may be substituted or a 5 to 14-membered aromatic heterocyclic group which may be substituted; and $R^{2r}$ and $R^{3r}$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted or a 5 to 14-membered aromatic heterocyclic group which may be substituted. The compound (R4) as a raw material for the production of the compound represented by the above formula (I) of the present invention can be produced by allowing the aldehyde (R2) and the guanidine derivative (R3) to react with the compound (R1) in the presence of a base, followed by aromatizing with an oxidant. The guanidine derivative (R3) to be used may form a salt with an acid such as hydrochloric acid, hydrobromic acid, sulfuric acid or acetic acid. The base used varies depending on the starting materials, the solvent to be used, and so on. Preferably, although not specifically limited to as far as the reaction is not inhibited, the base to be used may be an alkali metal alkoxide such as sodium methoxide, sodium ethoxide or potassium t-butoxide, or alternatively an alkali metal carbonate such as potassium carbonate or sodium carbonate. Examples of the oxidant to be used include: manganese compounds such as active manganese dioxide; quinones such as 2,3-dichloro-5,6-dicyanao-1,4-benzoquinone; and sulfur. The solvent to be used is not specifically limited to as far as the reaction is not inhibited and the starting materials and intermediates are dissolved to a certain degree. Examples of the solvents include ethanol, methanol, tetrahydrofuran, dichloromethane, dichloroethane, chloroform, N,N-dimethylformamide, N-methylpyrrolidone, dimethylsulfoxide, and mixed solvents thereof. The reaction temperature is preferably 0° C. to 120° C.

(Production Process S)

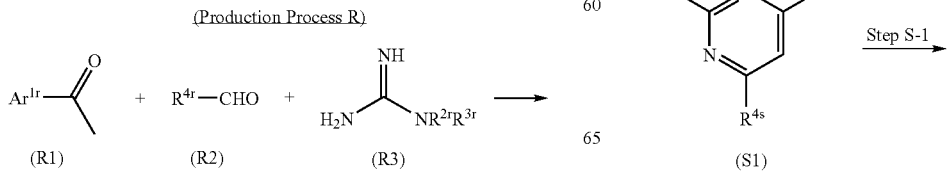

Step S-1

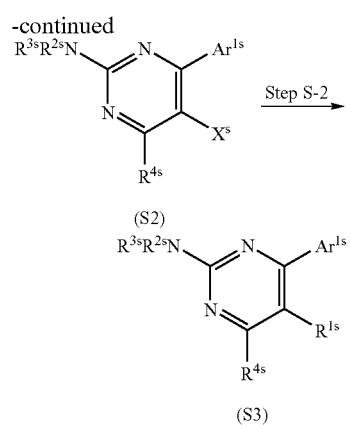

(S2)

(S3)

In the above formulae, $Ar^{1s}$ and $R^{1s}$ are the same as or different from each other and each represents an aromatic hydrocarbon cyclic group having six to fourteen carbon atoms which may be substituted or a 5 to 14-membered aromatic heterocyclic group which may be substituted; $R^{2s}$ and $R^{3s}$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted or a 5 to 14-membered aromatic heterocyclic group which may be substituted; $R^{4s}$ represents a hydrogen atom, an aromatic hydrocarbon cyclic group having six to fourteen carbon atoms which may be substituted or a 5 to 14-membered aromatic heterocyclic group which may be substituted; and $X^S$ represents a halogen atom. The compound (S3) of the present invention can be produced by Production Process S.

Step S-1: This step is to produce a 5-halogenopyrimidine derivative (S2) by halogenation at 5-position of the pyrimidine ring of the pyrimidine derivative (S1) obtained by Production Process Q or R described above using a halogenating agent in a solvent. The halogenating agent used is preferably N-bromosuccinimide, bromine, or the like. The solvent used varies depending on the starting materials, reagents, and so on. Preferably, although not specifically limited to as far as the reaction is not inhibited and the starting materials are dissolved to a certain degree, the solvents include alcohols such as methanol or ethanol; ethers such as tetrahydrofuran, dioxane, dimethoxyethane or diethyleneglycol dimethylether; N,N-dimethylformamide; and N-methylpyrrolidinone. The reaction temperature is generally −20° C. to room temperature.

Step S-2: This step is to produce the pyrimidine derivative (S3) of the present invention by allowing a tin reagent or the like, such as the compound (O2) obtained in Production Process O, to react with the 5-halogenopyrimidine derivative (S2) obtained in the production step S-1 in a solvent in the presence of a palladium catalyst. The palladium catalyst used varies depending on the starting materials, solvents used, and so on. Preferably, although not specifically limited to as far as the reaction is not inhibited, the palladium catalysts include dichlorobis(triphenylphosphine)palladium (II), palladium (II) acetate, tetrakis(triphenylphosphine)palladium (0), and tris(dibenzylideneacetone)dipalladium (0). The solvent used varies depending on the starting materials, reagents, and so on. Preferably, although not specifically limited to as far as the reaction is not inhibited and the starting materials are dissolved to a certain degree, the solvents include alcohols such as methanol or ethanol; ethers such as tetrahydrofuran, dioxane, dimethoxyethane or diethyleneglycol dimethylether; toluene; xylene; N,N-dimethylformamide; and N-methylpyrrolidinone. The reaction temperature is generally room temperature to 150° C., preferably around 100° C.

(Production Process T)

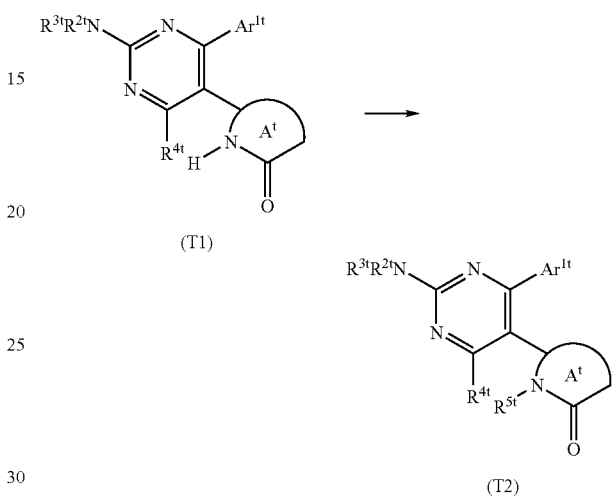

(T1)

(T2)

In the above formulae, $Ar^{1t}$ represents an aromatic hydrocarbon cyclic group having six to fourteen carbon atoms which may be substituted or a 5 to 14-membered aromatic heterocyclic group which may be substituted; $R^{2t}$ and $R^{3t}$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted, a 5 to 14-membered aromatic heterocyclic group which may be substituted, an acyl group having one to six carbon atoms which may be substituted or an alkylsulfonyl group having one to six carbon atoms which may be substituted; $R^{4t}$ represents a hydrogen atom, a halogen atom, a cyano group, an alkyl group having one to six carbon atoms which may be substituted, an alkenyl group having two to six carbon atoms which may be substituted, an alkynyl group having two to six carbon atoms which may be substituted, an aromatic hydrocarbon cyclic group having six to fourteen carbon atoms which may be substituted, a 5 to 14-membered aromatic heterocyclic group which may be substituted, a nitrogen atom which may be substituted, an oxygen atom which may be substituted or a sulfur atom which may be substituted; $R^{5t}$ represents an alkenyl group having two to six carbon atoms which may be substituted, an aromatic hydrocarbon cyclic group having six to fourteen carbon atoms or a 5 to 14-membered aromatic heterocyclic group which may be substituted; and the ring $A^t$ represents a dihydrooxopyridinyl group, a dihydrooxopyrimidinyl group, a dihydrooxopyrazinyl group or a dihydrooxopyridazinyl group. The compound (T2) of the present invention can be produced by the reaction between the compound (T1) and a boron reagent in a solvent in the presence of a base and a copper catalyst. The base used in the reaction varies depending on the starting materials, solvent used, and so on in the production. Preferably, although not specifically limited to as far as the reaction is not inhibited, the bases include tertiary amines such as pyridine, diisopropylethylamine or triethylamine. The copper catalyst used varies depending on the starting materials, solvent used, and so on in the production. Preferably, although not specifically limited to as far as the reaction is not inhibited, the copper catalysts include divalent copper compounds such as copper acetate, copper bromide or copper sulfate, and copper acetate is more preferred. The solvent used varies depending on the starting materials, reagents, and so on in the production. Preferably, although not specifically limited to as far as the reaction is not inhibited and the starting materials are dissolved to a certain degree, the solvents include N,N-dimethylformamide, tetrahydrofuran, ethylacetate, and dichloromethane dioxane. The reaction temperature is preferably room temperature to 120° C.

(Production Process U)

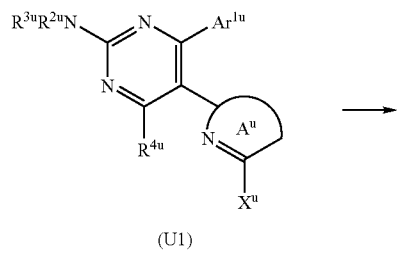

(U1)

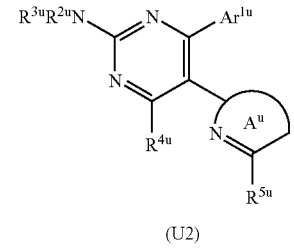

(U2)

In the above formulae, $Ar^{1u}$ represents an aromatic hydrocarbon cyclic group having six to fourteen carbon atoms which may be substituted or a 5 to 14-membered aromatic heterocyclic group which may be substituted; $R^{2u}$ and $R^{3u}$ are the same as or different from each other and each represents a hydrogen atom, an alkyl group having one to six carbon atoms which may be substituted, an alkenyl having two to six carbon atoms group which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted, a 5 to 14-membered aromatic heterocyclic group which may be substituted, an acyl group having one to six carbon atoms which may be substituted or an alkylsulfonyl group having one to six carbon atoms which may be substituted; $R^{4u}$ represents a hydrogen atom, a cyano group, an alkyl group having one to six carbon atoms which may be substituted, an alkenyl group having two to six carbon atoms which may be substituted, an alkynyl group having two to six carbon atoms which may be substituted, an aromatic hydrocarbon cyclic group having six to fourteen carbon atoms which may be substituted, a 5 to 14-membered aromatic heterocyclic group which may be substituted, a nitrogen atom which may be substituted or an oxygen atom which may be substituted; $R^{5u}$ represents a nitrogen atom which may be substituted, an oxygen atom which may be substituted or a sulfur atom which may be substituted; the ring $A^u$ represents a pyridyl group, a pyrimidinyl group, a pyrazinyl group or a pyridazinyl group; and $X^u$ represents a halogen atom, an alkylsulfonyloxy group or an arylsulfonyloxy group. The compound (U2) of the present invention can be produced by the reaction between the compound (U1) and a nucleophilic reagent in a solvent or in the absence of the solvent. The nucleophilic reagent used in the reaction is primary or secondary amine or alkali metal alkoxide. The alkali metal alkoxide is prepared by allowing an alkali metal or base to react with alcohol in a solvent or in the absence of the solvent. Preferably, an alkali metal used in the preparation of the alkali metal alkoxide is sodium or potassium. The base used in the preparation of the alkali metal alkoxide varies depending on the starting materials, solvents used, and so on in the production. Preferably, although not specifically limited to as far as the reaction is not inhibited, the base is an alkali metal hydride such as sodium hydride, or alternatively alkali metal alkoxide such as sodium methoxide, sodium ethoxide or potassium t-butoxide. The solvent used varies depending on the starting materials, reagents, and so on. Preferably, although not specifically limited to as far as the reaction is not inhibited and the starting materials and reagents are dissolved to a certain degree, the solvents include N,N-dimethylformamide, N-methylpyrrolidone, dimethylsulfoxide, alcohols such as methanol or ethanol, ethers such as tetrahydrofuran, 1,2-dimethoxyethane or 1,4-dioxane, water, and a mixed solvent thereof. The reaction temperature is preferably room temperature to 200° C.

(Production Process V)

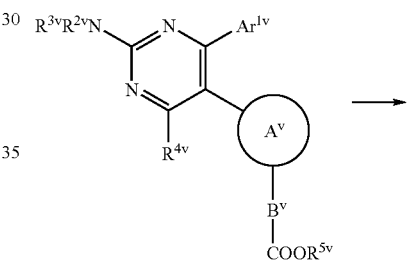

(V1)

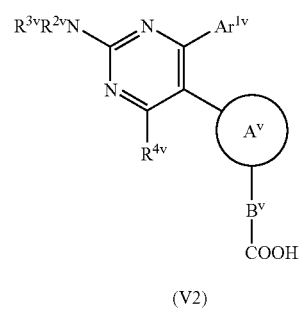

(V2)

In the above formulae, $Ar^{1v}$ represents an aromatic hydrocarbon cyclic group having six to fourteen carbon atoms which may be substituted or a 5 to 14-membered aromatic heterocyclic group which may be substituted; $R^{2v}$ and $R^{3v}$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted, a 5 to 14-membered aromatic heterocyclic group which may be substituted, an acyl group having one to six carbon atoms which may be substituted or an alkylsulfonyl group having one to six carbon atoms which may be substituted; $R^{4v}$ represents a hydrogen atom, a halogen atom, a cyano group, an alkyl group having one to six carbon atoms which may be substituted, an alkenyl group having two to six carbon atoms which may be substituted, an alkynyl group having two to six carbon atoms which may be substituted, an aromatic hydrocarbon cyclic group having six to fourteen carbon atoms which may be substituted, a 5 to 14-membered aromatic heterocyclic group which may be substituted, a nitrogen atom which may be substituted, an oxygen atom which may be substituted or a sulfur atom which may be substituted; $R^{5v}$ represents an alkyl group having one to six carbon atoms; the ring $A^v$ represents a pyridyl group, a pyrimidynyl group, a pyrazinyl group, a pyridazinyl group, a dihydrooxopyridinyl group, a dihydrooxopyrimidinyl group, a dihydrooxopyrazinyl group or a dihydrooxopyridazinyl group; and $B^v$ represents an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted or a 5 to 14-membered aromatic heterocyclic group which may be substituted. The compound (V2) of the present invention can be produced by allowing a base to react with the compound (V1) in a solvent. The base used in the reaction varies depending on the starting materials, solvent used, and so on. Preferably, although not specifically limited to as far as the reaction is not inhibited, the base is alkali metal hydroxide such as sodium hydroxide or potassium hydroxide. The solvent used varies depending on the starting materials, reagents, and so on. Preferably, although not specifically limited to as far as the reaction is not inhibited and the starting materials are dissolved to a certain degree, the solvents include methanol, tetrahydrofuran, dichloromethane, 1,2-dimethoxyethane, 1,4-dioxane, water, and mixed solvents thereof. The reaction temperature is preferably 0° C. to 120° C.

same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted or a 5 to 14-membered aromatic heterocyclic group which may be substituted; $R^{4w}$ represents a hydrogen atom, a halogen atom, a cyano group, an alkyl group having one to six carbon atoms which may be substituted, an alkenyl group having two to six carbon atoms which may be substituted, an alkynyl group having two to six carbon atoms which may be substituted, an aromatic hydrocarbon cyclic group having six to fourteen carbon atoms which may be substituted, a 5 to 14-membered aromatic heterocyclic group which may be substituted, a nitrogen atom which may be substituted, an oxygen atom which may be substituted or a sulfur atom which may be substituted; the ring $A^w$ represents a pyridyl group, a pyrimidinyl group, a pyrazinyl group or a pyridazinyl group; the ring $A'^w$ represents a dihydrooxopyridinyl group, a dihydrooxopyrimidinyl group, a dihydrooxopyrazinyl group or a dihydrooxopyridazinyl group; and $X^w$ represents a halogen atom. The compound (W2) of the present invention can be produced, for example, by this Production Process W. That is, the compound (W2) can be produced by hydrolyzing the compound (W1) as a starting material under acidic conditions. The acid used varies depending on the starting materials, reagents, solvent, and so on used. Preferably, although not specifically limited to as far as the reaction is not inhibited, the acid is hydrochloric acid, hydrobromic acid, sulfuric acid, or the like. This reaction is preferably carried out in water, or alternatively carried out in a mixed solvent of water with acetic acid or alcohols such as ethanol, for instance. Furthermore, the reaction temperature is generally room temperature to about 120° C., preferably 80° C. to 100° C.

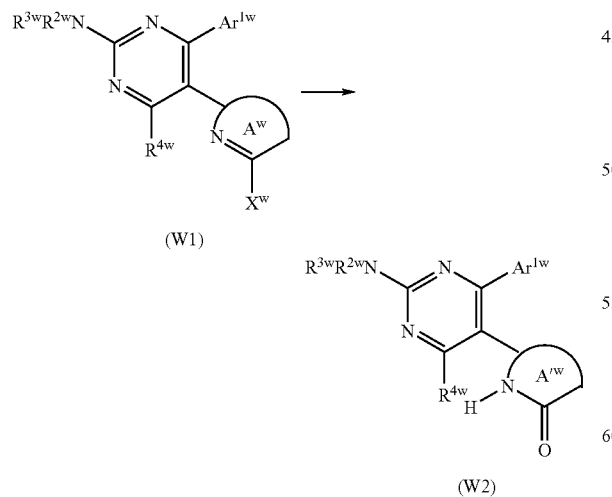

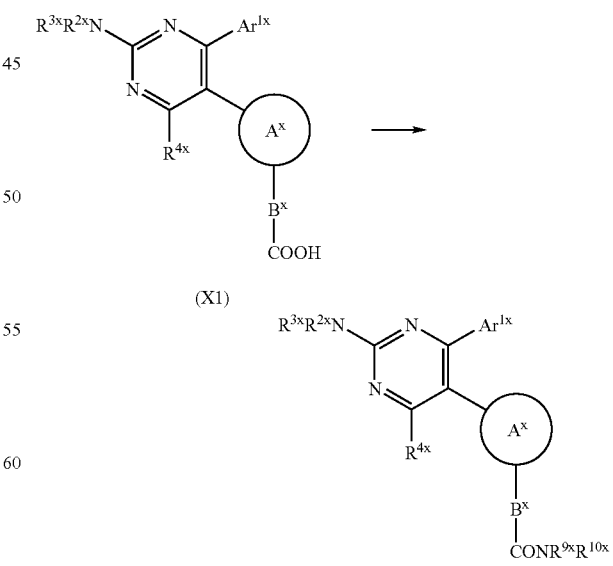

In the above formulae, $Ar^{1w}$ represents an aromatic hydrocarbon cyclic group having six to fourteen carbon atoms which may be substituted or a 5 to 14-membered aromatic heterocyclic group which may be substituted; $R^{2w}$ and $R^{3w}$ are the In the above formulae, $Ar^{1x}$ represents an aromatic hydrocarbon cyclic group having six to fourteen carbon atoms which may be substituted or a 5 to 14-membered aromatic heterocyclic group which may be substituted; $R^{2x}$ and $R^{3x}$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted, a 5 to 14-membered aromatic heterocyclic group which may be substituted, an acyl group having one to six carbon atoms which may be substituted or an alkylsulfonyl group having one to six carbon atoms which may be substituted; $R^{4x}$ represents a hydrogen atom, a halogen atom, a cyano group, an alkyl group having one to six carbon atoms which may be substituted, an alkenyl group having two to six carbon atoms which may be substituted, an alkynyl group having two to six carbon atoms which may be substituted, an aromatic hydrocarbon cyclic group having six to fourteen carbon atoms which may be substituted, a 5 to 14-membered aromatic heterocyclic group which may be substituted, a nitrogen atom which may be substituted, an oxygen atom which may be substituted or a sulfur atom which may be substituted; $R^{9x}$ and $R^{10x}$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted or a 5 to 14-membered aromatic heterocyclic group which may be substituted; the ring $A^x$ represents a pyridyl group, a pyrimidinyl group, a pyrazinyl group, a pyridazinyl group, a dihydrooxopyridinyl group, a dihydrooxopyrimidinyl group, a dihydrooxopyrazinyl group or a dihydrooxopyridazinyl group; and $B^x$ represents an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted or a 5 to 14-membered aromatic heterocyclic group which may be substituted. The compound (X2) of the present invention can be produced by dehydration-condensation of a carboxylic acid derivative (X1) with amine in the presence of a condensing agent in a solvent. The condensing agent used is preferably 3-(3'-dimethylaminopropyl)-1-ethylcarbodiimide. The reaction can be accelerated by the addition of 1-hydroxybenzotriazole or the like. Furthermore, when the amine to be condensed with the carboxylic acid forms a salt with hydrogenchloride or the like, an appropriate amount of tertiary amine such as triethylamine is added. Preferable examples of the solvent used include ethers such as tetrahydrofuran, dioxane, 1,2-dimethoxyethane or diethylene glycol, N,N-dimethylformamide and 1-methylpyrrolidinone. The reaction temperature is generally 0° C. to 50° C., preferably around room temperature.

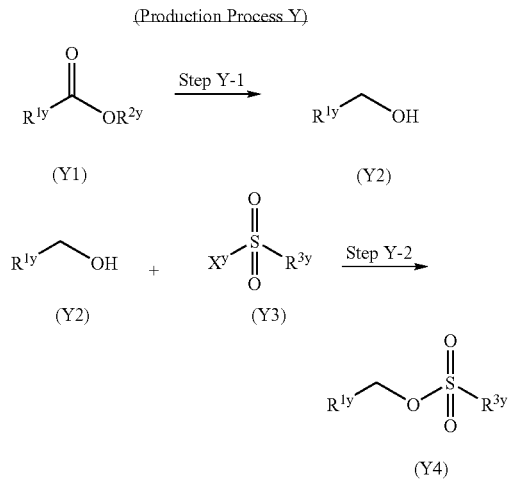

(Production Process Y)

In the above formulae, $R^{1y}$ represents an aromatic hydrocarbon cyclic group having six to fourteen carbon atoms which may be substituted or a 5 to 14-membered aromatic heterocyclic group which may be substituted; $R^{2y}$ represents a hydrogen atom or an alkyl group having one to six carbon atoms; $R^{3y}$ represents an alkyl group having one to six carbon atoms which may be substituted, an aromatic hydrocarbon cyclic group having six to fourteen carbon atoms which may be substituted or a 5 to 14-membered aromatic heterocyclic group which may be substituted; and $X^y$ represents a halogen atom. The compound (Y4) as a raw material for the production of the compound represented by the formula (I) of the present invention can be produced by this Production Process Y.

Step Y-1: This step is to produce the compound (Y2) by allowing a reducing agent to react with the compound (Y1) in a solvent to convert the ester or carboxyl group of the compound (Y1) into a hydroxymethyl group. The reducing agent used is preferably sodium tetrahydroborate, lithium aluminum hydride, a borane-tetrahydrofuran complex, or the like. The solvent used varies depending on the starting materials, reagents, and so on. Preferably, although not specifically limited to insofar as the reaction is not inhibited and the starting materials are dissolved to a certain degree, the solvents include alcohols such as ethanol and ethers such as diethyl ether, tetrahydrofuran, and 1,4-dioxane. The reaction temperature is preferably −20° C. to room temperature.

Step Y-2: This step is to produce the sulfonic acid ester derivative (Y4) by allowing the compound (Y2) to react with the sulfonyl halide derivative (Y3) in a solvent in the presence of a base. The base used in the reaction is preferably tertiary amine such as triethylamine. The solvent used varies depending on the starting materials, reagents, and so on. Preferably, although not specifically limited to insofar as the reaction is not inhibited and the starting materials are dissolved to a certain degree, the solvents include dichloromethane, dichloroethane, diethyl ether, tetrahydrofuran, and 1,4-dioxane. The reaction temperature is preferably −20° C. to room temperature.

(Production Process Z)

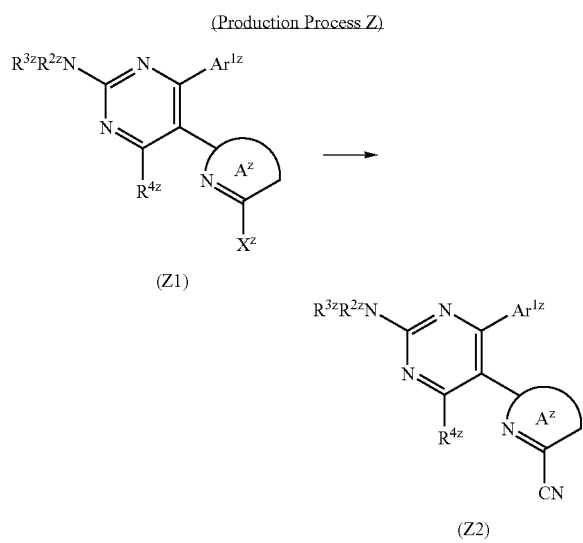

(Z1)

(Z2)

In the above formulae, $Ar^{1z}$ represents an aromatic hydrocarbon cyclic group having six to fourteen carbon atoms which may be substituted or a 5 to 14-membered aromatic heterocyclic group which may be substituted; $R^{2z}$ and $R^{3z}$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic hydrocarbon cyclic group having six to fourteen carbon atoms which may be substituted, a 5 to 14-membered aromatic heterocyclic group which may be substituted, an acyl group having one to six carbon atoms which may be substituted or an alkylsulfonyl group having one to six carbon atoms which may be substituted; $R^{4z}$ represents a hydrogen atom, a cyano group, an alkyl group having one to six carbon atoms which may be substituted, an alkenyl group having two to six carbon atoms which may be substituted, an alkynyl group having two to six carbon atoms which may be substituted, an aromatic hydrocarbon cyclic group having six to fourteen carbon atoms which may be substituted, a 5 to 14-membered aromatic heterocyclic group which may be substituted, a nitrogen atom which may be substituted, an oxygen atom which may be substituted or a sulfur atom which may be substituted; the ring $A^z$ represents a pyridyl group, a pyrimidinyl group, a pyrazinyl group or a pyridazinyl group; and $X^z$ represents a halogen atom. The compound (Z2) of the present invention can be produced by the reaction of the compound (Z1) and alkali metal cyanide in a solvent. The alkali metal cyanide used in the reaction is preferably sodium cyanide or potassium cyanide. The solvent used varies depending on the starting materials, regents, and so on. Preferably, although not specifically limited to insofar as the reaction is not inhibited and the starting materials are dissolved to a certain degree, the solvents include dimethylsulfoxide, N,N-dimethylformamide and N-methylpyrrolidone. The reaction temperature is preferably 100° C. to 200° C.

Typical examples of the production processes for the compounds (I) according to the present invention have been illustrated above. The material compounds used in the production of the compounds of the present invention may form salts and/or solvates and are not specifically limited, as long as they do not adversely affect the reaction. When the compounds (I) according to the present invention are obtained as free form, they can be converted into possible salts of the above-mentioned compounds (I) according to a conventional procedure. Various isomers such as geometrical isomers, optical isomers based on an asymmetric carbon, rotational isomers, stereoisomers, and tautomers obtained as the compounds (I) according to the present invention can be purified and isolated according to a conventional separation means. Such separation means include, for example, recrystallization, diastereomeric salt method, enzymatic resolution, and a variety of chromatography such as thin layer chromatography, column chromatography or gas chromatography.

The compounds represented by the formula (I) according to the present invention, salts thereof or solvates of them can be formulated into pharmaceutical preparations as intact or as a mixture with, for example, a known pharmacologically acceptable carrier according to a conventional procedure. Preferred dosage forms are tablets, powders, subtle granules, granules, coated tablets, capsules, syrups, troches, inhalants, suppositories, injections, ointments, ophthalmic ointments, eye drops, nasal drops, ear drops, cataplasms, and lotions. In the formulation, generally used fillers, binders, disintegrators, lubricants, coloring agents, and flavoring agents, as well as stabilizers, emulsifiers, absorbefacients, surfactants, pH adjusting agents, antiseptics, and antioxidants according to necessity can be used. They can be formulated according to a conventional procedure using components generally used as raw materials for pharmaceutical preparations. Examples of such components include (1) animal and vegetable oils such as soybean oil, beef tallow and synthetic glycerides; (2) hydrocarbons such as liquid paraffins, squalane and solid paraffins; (3) ester oils such as octyldodecyl myristate and isopropyl myristate; (4) higher alcohols such as cetostearyl alcohol and behenyl alcohol; (5) silicone resins; (6) silicone oils; (7) surfactants such as polyoxyethylene fatty acid esters, sorbitan fatty acid esters, glycerin fatty acid esters, polyoxyethylene sorbitan fatty acid esters, polyoxyethylene hydrogenated castor oils and polyoxyethylene-polyoxypropylene block copolymers; (8) water-soluble polymers such as hydroxyethyl cellulose, poly(acrylic acid)s, carboxyvinyl polymers, polyethylene glycol, polyvinylpyrrolidone and methylcellulose; (9) lower alcohols such as ethanol and isopropanol; (10) polyhydric alcohols such as glycerol, propylene glycol, dipropylene glycol and sorbitol; (11) sugars such as glucose and sucrose; (12) inorganic powders such as silicic anhydride, magnesium aluminium silicate and aluminium silicate; and (13) purified water. 1) The fillers include, for example, lactose, corn starch, sucrose, glucose, mannitol, sorbitol, crystalline cellulose and silicon dioxide; 2) the binders include, for example, polyvinyl alcohol, polyvinyl ether, methylcellulose, ethylcellulose, gum arabic, gum tragacanth, gelatin, shellac, hydroxypropyl cellulose, hydroxypropylmethyl cellulose, polyvinylpyrrolidone, polypropylene glycol-polyoxyethylene block polymers, meglumine, calcium citrate, dextrin and pectin; 3) the disintegrators include, for example, starch, agar, gelatin powder, crystalline cellulose, calcium carbonate, sodium hydrogencarbonate, calcium citrate, dextrin, pectin and carboxymethylcellulose calcium; 4) the lubricants include, for example, magnesium stearate, talc, polyethylene glycol, silica, and hardened vegetable oils; 5) the coloring agents can be any coloring agents which are approved to add to pharmaceutical preparations; 6) the flavoring agents include, for example, cocoa powder, menthol, aromatic powder (empasm), peppermint oil, camphol (borneol) and cinnamon powder; and 7) the antioxidants can be any antioxidants which are approved to add to pharmaceutical preparations, such as ascorbic acid and α-tocopherol.

1) The oral preparation is produced by mixing the compound according to the present invention or a salt thereof with a filler, and if necessary, a binder, disintegrator, lubricant, coloring agent, flavoring agent, and other components, and formulating the mixture according to a conventional procedure into, for example, a powder, subtle granules, granules, tablet, coated tablet or capsules. 2) The tablets and granules can be appropriately coated with, for example, sugar or gelatin according to necessity. 3) The liquid formulations such as syrups, injection preparations or eye drops can be prepared according to a conventional procedure by adding a pH adjusting agent, solubilizer, and isotonizing agent, and if necessary, a solubilizing agent, stabilizer, buffer, suspending agent, antioxidant, and other components. The liquid formulations can also be formed into freeze-dried products. The injections can be administered intravenously, subcutaneously and/or intramuscularly. Preferred examples of the suspending agents are methylcellulose, polysorbate 80, hydroxyethyl cellulose, gum arabic, powdered tragacanth, carboxymethylcellulose sodium and polyoxyethylene sorbitan monolaurate; preferred examples of the solubilizers are polyoxyethylene hydrogenated caster oil, polysorbate 80, nicotinamide and polyoxyethylene sorbitan monolaurate; preferred examples of the stabilizers are sodium sulfite, sodium metasulfite and ether; preferred examples of the preservatives are methyl p-hydroxybenzoate, ethyl p-hydroxybenzoate, sorbic acid, phenol, cresol and chlorocresol. 4) The external preparations can be produced according to a conventional procedure not specifically limited. Base materials for use herein can be any raw materials generally used in, for example, pharmaceutical preparations, quasi drugs and cosmetics. Such raw materials include, for example, animal and vegetable oils, mineral oils, ester oils, waxes, higher alcohols, fatty acids, silicone oils, surfactants, phospholipids, alcohols, polyhydric alcohols, water-soluble polymers, clay minerals, and purified water. Where necessary, any of pH adjusting agents, antioxidants, chelating agents, antiseptics and antimolds, coloring agents, flavors, and others can be added. In addition, components having differentiation-inducing action, blood-flow accelerators, bactericides, anti-inflammatory agents, cell activators, vitamins, amino acids, humectants, keratolytic agents, and other components can be added according to necessity.

The dose of the pharmaceutical preparation according to the present invention varies depending on the degree of symptom, age, sex, body weight, administration mode, type of the salt, difference in sensibility to the drug, concrete type of the disease and other factors. Generally, the pharmaceutical preparation may be administered to an adult in one to several divided doses at a daily dose of about 30 µg to about 10 g, preferably 100 µg to 5 g, and more preferably 100 µg to 100 mg for oral administration, or about 30 µg to about 1 g, preferably 100 µg to 500 mg, and more preferably 100 µg to 30 mg for injection administration.

The present invention can provide a novel pyrimidine compound. The compounds according to the present invention, salts thereof or solvates of them have an excellent antagonism against an adenosine receptor (adenosine $A_1$, $A_{2A}$, $A_{2B}$ or $A_3$ receptor) and are specifically excellent as an antagonist against the adenosine $A_2$ receptors, specifically against the adenosine $A_{2A}$ and/or $A_{2B}$ receptor. They are useful as an agent for treating or preventing a disease to which the adenosine receptor (adenosine $A_1$, $A_{2A}$, $A_{2B}$ or $A_3$ receptor) relates and a disease against which an antagonist of the receptor is efficacious. They are useful as an agent for treating, preventing or improving various constipations (functional constipation, irritable bowel syndrome, constipation accompanying irritable bowel syndrome, organic constipation, constipation accompanying enteroparalytic ileus, constipation accompanying congenital digestive tract dysfunction, constipation accompanying ileus), as an agent for treating, preventing or improving diabetes mellitus, diabetic complications, diabetic retinopathy, obesity or asthma, and are also useful as, for example, a hypoglycemic agent, agent for ameliorating glucose intolerance, insulin sensitizer, antihypertensive drug, diuretic agent, antidepressant, agent for treating osteoporosis, agent for treating Parkinson's disease, agent for treating Alzheimer's disease, agent for treating an inflammatory bowel disease or agent for treating Crohn's disease.

EXAMPLES

The following Reference Examples, Examples and Test Examples are illustrative, and the compounds of the present invention are under no circumstances restricted by the following examples. Those skilled in the art can modify not only the following Examples but also the claims according to the present description in various ways to exploit to the full of the present invention, and such modifications and variations are also included within the scope of the appended claims relating to the present description.

Reference Example 1

Ethyl (E)-3-(3-fluorophenyl)-2-(4-pyridyl)-2-propenoate

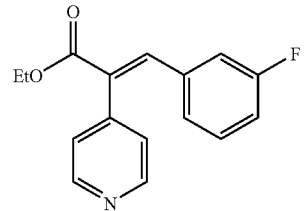

A solution of ethyl 4-pyridylacetate (25.0 g, 0.151 mol) and 3-fluorobenzaldehyde (20.7 g, 0.167 mol) in a mixture of acetic anhydride (100 mL) and triethylamine (20 mL) was heated under reflux for 5.5 hours. After standing to cool, the reaction mixture was concentrated. The residue was diluted with ethyl acetate and a saturated aqueous sodium hydrogencarbonate solution, and the aqueous layer was extracted with ethyl acetate. The combined organic layers were washed with a saturated aqueous sodium hydrogencarbonate solution twice and brine, dried over anhydrous sodium sulfate and then concentrated. The residue was subjected to silica gel column chromatography (eluent; hexane, hexane:ethyl acetate=9:1), to give the title compound (25.5 g, 62%) as a red-orange oil.

$^1$H NMR (400 MHz, CDCl$_3$) δ ppm; 1.28 (3H, t, J=7.2 Hz), 4.27 (2H, q, J=7.2 Hz), 6.70-6.75 (1H, m), 6.80-6.84 (1H, m), 6.91-6.97 (1H, m), 7.12-7.18 (1H, m), 7.16 (2H, dd, J=1.6, 4.4 Hz), 7.85 (1H, s), 8.62 (2H, dd, J=1.6, 4.4 Hz).

Reference Example 2

Ethyl (E)-3-(2-furyl)-2-(4-pyridyl)-2-propenoate

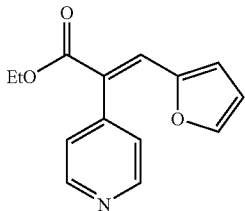

The title compound was synthesized in a similar manner to Reference Example 1 using 2-furaldehyde.

$^1$H NMR (400 MHz, CDCl$_3$) δ ppm; 1.20 (3H, t, J=7.2 Hz), 4.18 (2H, q, J=7.2 Hz), 6.51 (1H, d, J=3.6 Hz), 6.54 (1H, dd, J=1.6, 3.6 Hz), 7.29 (2H, dd, J=1.6, 4.4 Hz), 7.66 (1H, s), 7.69 (1H, d, J=1.6 Hz), 8.62 (2H, dd, J=1.6, 4.4 Hz).

Reference Example 3

(E)-4-(2-Furyl)-3-(4-pyridyl)-3-buten-2-one

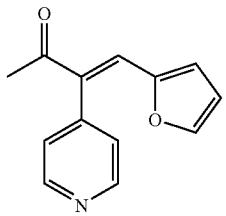

Under a nitrogen atmosphere, a 3.0M solution of methylmagnesium bromide in diethyl ether (3.7 ml, 11.1 mmol) was added dropwise over 5 minutes to a 1M solution of lithium bis(trimethylsilyl)amide in tetrahydrofuran (22 ml, 22 mmol) at −50° C. (dry ice-acetone bath), followed by stirring as it was for 1 hour. Then, a solution of ethyl (E)-3-(2-furyl)-2-(4-pyridyl)-2-propenoate (2.4 g, 9.87 mmol) in tetrahydrofuran (20 ml) was added dropwise thereinto over 5 minutes. The reaction mixture was stirred for 30 minutes while elevating to room temperature, and then the reaction was terminated by adding hydrochloric acid. After diluting with a saturated aqueous ammonium chloride solution, the mixture was extracted with ethyl acetate. The organic layer was washed with brine, dried over anhydrous magnesium sulfate and concentrated. The residue was subjected to silica gel column chromatography (elution solvent; hexane:ethyl acetate=1:1 to 4:1), to give the title compound (0.52 g, 23%).

$^1$H NMR (400 MHz, CDCl$_3$) δ ppm; 2.36 (3H, s), 6.07 (1H, d, J=3.2 Hz), 6.34 (1H, dd, J=1.6, 3.2 Hz), 7.16 (2H, dd, J=1.8, 4.4 Hz), 7.38 (1H, d, J=1.6 Hz), 7.55 (1H, s), 8.70 (2H, dd, J=1.8, 4.4 Hz).

Reference Example 4

(E)-3-(3-Fluorophenyl)-2-(4-pyridyl)-2-propenenitrile

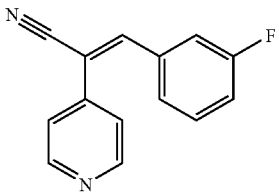

Sodium (3.0 g, 130 mmol) was dissolved in ethanol (150 mL), 4-pyridylacetonitrile hydrochloride (10 g, 65 mmol) was added thereto, and then the mixture was stirred at room temperature. After 10 minutes, 3-fluorobenzaldehyde (8 g, 65 mmol) was added thereto, followed by stirring as it was for 30 minutes. The resulting precipitates were collected by filtration and washed with a small portion of water, to give the title compound (8.2 g, 56%) as a colorless solid.

$^1$H NMR (400 MHz, DMSO-d$_6$) δ ppm; 7.40-7.46 (1H, m), 7.61-7.68 (1H, m), 7.75 (2H, dd, J=1.6, 4.4 Hz), 7.77-7.86 (2H, m), 8.37 (1H, s), 8.73 (2H, dd, J=1.6, 4.4 Hz).

Reference Example 5

1-(2-Furyl)-2-(4-pyridyl)-1-ethanone

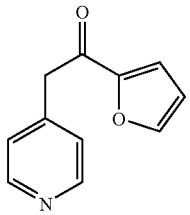

To a solution of 4-picoline (4.6 g, 49.4 mmol) and ethyl 2-furancarboxylate (7.7 g, 54.9 mmol) in tetrahydrofuran (40 ml) was dropwise added lithium bis(trimethylsilyl)amide (100 ml, 100 mmol) over 1 hour at 0° C. under an atmosphere of nitrogen gas, followed by stirring as it was for 2 hours. Hexane (140 ml) was added to the reaction mixture, and the resulting crystals were collected by filtration. The resulting crystals were dissolved in ethyl acetate and a saturated aqueous ammonium chloride solution. The organic layer was washed with a saturated aqueous ammonium chloride solution twice and brine, dried over anhydrous sodium sulfate and concentrated. Hexane was added to the residue, and the resulting precipitates were collected by filtration and washed with hexane, to give the title compound (6.5 g, 70%) as a pale yellow solid.

$^1$H NMR (400 MHz, DMSO-d$_6$) δ ppm; 4.26 (2H, s), 6.77 (1H, dd, J=2.0, 3.6 Hz), 7.31 (2H, dd, J=1.6, 4.4 Hz), 7.65 (1H, dd, J=0.8, 3.6 Hz), 8.05 (1H, dd, J=0.8, 2.0 Hz), 8.51 (2H, dd, J=1.6, 4.4 Hz).

Reference Example 6

3-(Dimethylamino)-1-(2-furyl)-2-(4-pyridyl)-2-propen-1-one

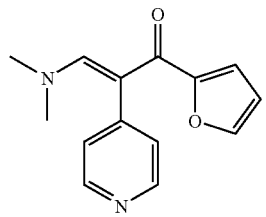

N,N-Dimethylformamide dimethyl acetal (5 ml) was added to 1-(2-furyl)-2-(4-pyridyl)-1-ethanone (2.0 g, 10.7 mmol) and the mixture was stirred at 100° C. for 2 hours. After cooling as it was, the reaction mixture was diluted with ethyl acetate and a saturated aqueous ammonium chloride solution. The aqueous layer was extracted with ethyl acetate (×6). The combined organic layers were dried over anhydrous sodium sulfate and then concentrated, to give the title compound (2.5 g, 97%) as a reddish brown oil.

¹H NMR (400 MHz, DMSO-d₆) δ ppm; 2.80 (6H, br s), 6.53 (1H, br), 6.60 (1H, br), 7.10 (2H, d, J=4.0 Hz), 7.65 (1H, br), 7.75 (1H, s), 8.44 (2H, d, J=4.0 Hz).

Reference Example 7

(6-Chloro-3-pyridyl)methanol

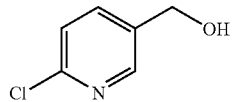

To a solution of ethyl 6-chloronicotinate (25.8 g, 0.139 mol) in ethanol was added sodiumborohydride (10.5 g, 0.278 mol), followed by stirring under an atmosphere of nitrogen gas at room temperature. After 41 hours, the reaction mixture was concentrated and then the residue was diluted with a saturated aqueous ammonium chloride solution and ethyl acetate. The organic layer was washed with a saturated aqueous ammonium chloride solution, dried over anhydrous sodium sulfate and concentrated. The residue was subjected to silica gel column chromatography (elution solvent; hexane, hexane:ethyl acetate=4:1, 2:1, and 3:2), to give the title compound (11.7 g, 58%) as a pale yellow solid.

¹H NMR (400 MHz, DMSO-d₆) δ ppm; 4.54 (2H, d, J=5.6 Hz), 5.43 (1H, t, J=5.6 Hz), 7.48 (1H, d, J=8.4 Hz), 7.80 (1H, dd, J=2.4, 8.4 Hz), 8.35 (1H, d, J=2.4 Hz).

Reference Example 8

(6-Chloro-3-pyridyl)methyl methanesulfonate

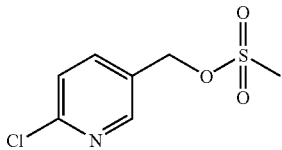

To a solution of (6-chloro-3-pyridyl)methanol (4.5 g, 31.3 mmol) and triethylamine (13.2 ml, 94.7 mmol) in dichloromethane (90 ml) was dropwise added methanesulfonyl chloride (3.6 ml, 46.5 mmol) over 45 minutes at −9° C. to 4° C. under an atmosphere of nitrogen gas, followed by stirring as it was. After 1 hour, the reaction mixture was elevated to room temperature. The reaction mixture was washed with an aqueous saturated sodium bicarbonate solution and a saturated aqueous ammonium chloride solution, dried over anhydrous sodium sulfate and concentrated, to give the title compound (6.14 g, 88%) as a pale brown solid.

¹H NMR (400 MHz, DMSO-d₆) δ ppm; 3.30 (3H, s), 5.34 (2H, s), 7.61 (1H, dd, J=0.6, 8.0 Hz), 7.97 (1H, dd, J=2.4, 8.0 Hz), 8.53 (1H, dd, J=0.6, 2.4 Hz).

Reference Example 9

2-(6-Chloro-3-pyridyl)-1-(2-furyl)-1-ethanone

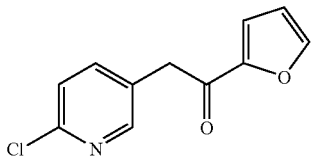

To a mixture of 2-furaldehyde (7.9 g, 82.2 mmol) and zinc (II) iodide (110 mg, 0.345 mmol) was dropwise added trimethylsilyl cyanide (11.0 ml, 82.5 mmol) over 10 minutes at 0° C. under an atmosphere of nitrogen gas, followed by stirring as it was. After 30 minutes, the reaction mixture was diluted with tetrahydrofuran (200 ml) and then cooled to −78° C. A 1.0M solution of lithium bis(trimethylsilyl)amide in tetrahydrofuran (86 ml, 86 mmol) was added dropwise thereto over 1 hour and then a solution of (6-chloro-3-pyridyl)methyl methanesulfonate (18.1 g, 81.7 mmol) in tetrahydrofuran (50 ml) was added dropwise over 1.5 hours thereto, followed by stirring while gradually elevated to room temperature. After 12.5 hours, a 1.0M solution of tetrabutylammonium fluoride in tetrahydrofuran (86 ml, 86 mmol) was added thereto, followed by stirring as it was. After further 30 minutes, the reaction mixture was diluted with a saturated aqueous ammonium chloride solution and ethyl acetate. The resulting organic layer was washed with a saturated aqueous ammonium chloride solution twice, dried over anhydrous sodium sulfate and concentrated. The residue was subjected to silica gel column chromatography (elution solvent; hexane, hexane:ethyl acetate=10:1, 4:1, 3:1, and 2:1) and then suspended in hexane. Subsequently, the resulting precipitates were collected by filtration, to give the title compound (11.9 g, 54%) as a pale brown solid.

¹H NMR (400 MHz, DMSO-d₆) δ ppm; 4.31 (2H, s), 6.78 (1H, dd, J=1.8, 3.4 Hz), 7.50 (1H, d, J=8.4 Hz), 7.64 (1H, d, J=3.4 Hz), 7.77 (1H, dd, J=2.4, 8.4 Hz), 8.06 (1H, d, J=1.8 Hz), 8.33 (1H, d, J=2.4 Hz).

Reference Example 10

2-(6-Chloro-3-pyridyl)-3-(dimethylamino)-1-(2-furyl)-2-propen-1-one

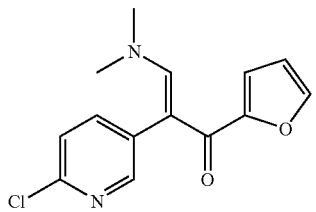

The title compound was synthesized in a similar manner to Reference Example 6 using 2-(6-chloro-3-pyridyl)-1-(2-furyl)-1-ethanone.

¹H NMR (400 MHz, DMSO-d₆) δ ppm; 2.79 (6H, br s), 6.55 (1H, dd, J=2.0, 3.4 Hz), 6.62 (1H, d, J=3.4 Hz), 7.45 (1H, d, J=8.0 Hz), 7.59 (1H, dd, J=2.4, 8.0 Hz), 7.77 (2H, d, J=2.0 Hz), 8.14 (1H, d, J=2.4 Hz).

Reference Example 11

(E)-3-(3-Fluorophenyl)-2-(6-methoxy-3-pyridyl)-2-propenenitrile

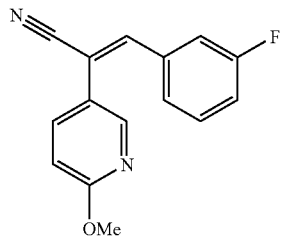

To a suspension of sodium hydride (8.8 g, 0.220 mol) in 1,2-dimethoxyethane (300 ml) was added diethyl cyanomethylphosphonate (19.7 g, 0.122 mol) little by little at room temperature under an atmosphere of nitrogen gas. After stirring for 15 minutes, 5-bromo-2-methoxypyridine (20.0 g, 0.106 mol) and tetrakis(triphenylphosphine)palladium (0) (2.0 g, 1.73 mmol) were successively added thereto, followed by heating to 90° C. and stirring for 6 hours. The reaction mixture was cooled as it was and further ice-cooled. 3-Fluorobenzaldehyde (13.7 g, 0.110 mol) was added dropwise thereto over 1.5 hours at 1 to 4° C. under an atmosphere of nitrogen gas, followed by stirring further for 2.5 hours while gradually elevating to room temperature. The reaction mixture was diluted with a saturated aqueous ammonium chloride solution and ethyl acetate, and then the aqueous layer was extracted with ethyl acetate. The combined organic layers were washed with a saturated aqueous ammonium chloride solution twice, dried over anhydrous sodium sulfate and then concentrated. The residue was suspended in methanol, and then the resulting solid was collected by filtration and washed with diethyl ether and hexane, to give the title compound (7.80 g, 29%) as a colorless solid.

$^1$H NMR (400 MHz, DMSO-$d_6$) δ ppm; 3.92 (3H, s), 7.00 (1H, d, J=8.8 Hz), 7.34-7.40 (1H, m), 7.57-7.64 (1H, m), 7.69-7.78 (2H, m), 8.03 (1H, s), 8.11 (1H, dd, J=2.6, 8.8 Hz), 8.53 (1H, d, J=2.6 Hz).

Reference Example 12

2-Amino-6-(3-fluorophenyl)-5-(4-pyridyl)-3,4-dihydro-4-pyrimidinone

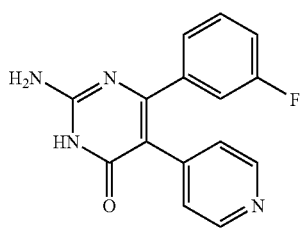

(Method 1)

Sodium (3.2 g, 139 mmol) was dissolved in ethanol (200 ml), and then 4-pyridylacetonitrile (10.0 g, 64.7 mmol), 3-fluorobenzaldehyde (7.3 ml, 68.8 mmol) and guanidine hydrochloride (7.0 g, 73.3 mmol) were successively added thereto, followed by heating under reflux for 2 days. The insoluble matters were filtered off and the filtrate was concentrated. The residue was subjected to silica gel column chromatography (elution solvent; dichloromethane, dichloromethane:methanol=20:1, 10:1, 5:1), to give a 5,6-dihydro product (13.6 g) of the title compound as a crude product. Sulfur (26.4 g, 82.3 mmol as S) was added to the product, followed by heating at 185° C. for 2.5 hours. After cooling as it was, the reaction mixture was suspended in methanol, and the insoluble matters were filtered off and washed with 2N hydrochloride. Methanol in the filtrate was concentrated and the residue was washed with ethyl acetate twice. The aqueous layer was adjusted to pH 11 with a 5N aqueous sodium hydroxide solution, washed with ethyl acetate twice and then neutralized with 2N hydrochloride. The resulting crystals were collected by filtration, and washed with water and ethyl acetate, to give the title compound (6.2 g, 34%) as a colorless solid. Furthermore, in this method, the title compound was also obtained by isolating (E)-3-(3-fluorophenyl)-2-(4-pyridyl)-2-propenenitrile and then subjecting it to a cyclization reaction with guanidine in a similar manner to Reference Example 4.

(Method 2)

Sodium (3.4 g, 147 mmol) was dissolved in ethanol (500 ml), and then ethyl (E)-3-(3-fluorophenyl)-2-(4-pyridyl)-2-propenoate (33 g, 121 mmol) and guanidine hydrochloride (13.9 g, 146 mmol) were added thereto, followed by heating under reflux for 13 hours. After cooling as it was, the solvent was removed. Tetrahydrofuran (500 ml) was added to the residue, the insoluble matters were filtered off, and the filtrate was concentrated. To a solution of the residue in tetrahydrofuran (1500 ml)-methanol (100 ml) was added active manganese dioxide (250 g), followed by heating under reflux. After 2 hours, additional active manganese dioxide (100 g) was added thereto, followed by heating under reflux further for 1 hour and 15 minutes. After cooling as it was, the manganese dioxide was filtered off through Celite and washed with tetrahydrofuran and methanol. The collected filtrate was concentrated and acetonitrile was added to the residue. The resulting precipitates were collected by filtration, to give the title compound (15 g, 44%) as a yellow powder.

$^1$H NMR (400 MHz, DMSO-$d_6$) δ ppm; 6.86 (2H, br s), 6.96 (1H, d, J=7.6 Hz), 7.00-7.07 (3H, m), 7.00-7.15 (1H, m), 7.20-7.28 (1H, m), 8.34 (2H, d, J=3.2 Hz); MS m/e (ESI) 283 (MH$^+$).

Reference Example 13

2-Amino-6-(2-furyl)-5-(4-pirydyl)-3,4-dihydro-4-pyrimidinone

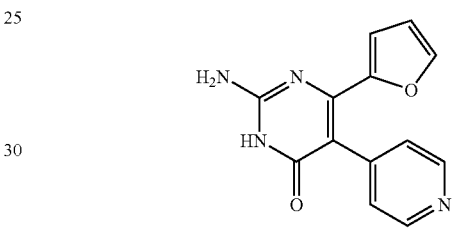

The title compound was synthesized in a similar manner to Method 1 of Reference Example 12 using 2-furaldehyde.

$^1$H NMR (400 MHz, DMSO-$d_6$) δ ppm; 6.48 (1H, dd, J=1.6, 3.6 Hz), 6.54 (1H, dd, J=0.8, 3.6 Hz), 6.91 (2H, br s), 7.21 (2H, dd, J=1.6, 4.6 Hz), 7.54 (1H, dd, J=0.8, 1.6 Hz), 8.52 (2H, dd, J=1.6, 4.6 Hz); MS m/e (ESI) 255 (MH$^+$).

Reference Example 14

3-(Dimethylamino)-1-(2-furyl)-2-propen-1-one

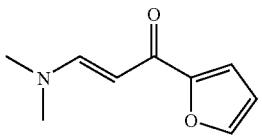

A mixture of 2-acetylfuran (25.0 g, 0.227 mol) and N,N-dimethylformamide dimethylacetal (40 ml) was stirred at 100° C. for 9 hours. After cooling as it was, the reaction mixture was concentrated. To the residue were added diethyl ether and hexane. The resulting solid was collected by filtration and washed with hexane, to give the title compound (36.5 g, 97%) as a brown solid.

$^1$H NMR (400 MHz, DMSO-$d_6$) δ ppm; 2.88 (3H, br s), 3.14 (3H, br s), 5.65 (1H, d, J=12.6 Hz), 6.60 (1H, dd, J=2.0, 3.4 Hz), 7.10 (1H, dd, J=0.8, 3.4 Hz), 7.68 (1H, d, J=12.6 Hz), 7.79 (1H, dd, J=0.8, 2.0 Hz).

Reference Example 15

4-(2-Furyl)-2-pyrimidinylamine

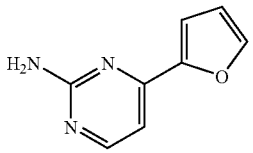

A suspension of 3-(dimethylamino)-1-(2-furyl)-2-propen-1-one (5.0 g, 30.3 mmol), guanidine hydrochloride (5.8 g, 60.7 mmol) and potassium carbonate (8.4 g, 60.9 mmol) in N,N-dimethylformamide (50 ml) was stirred at 100° C. for 21 hours. After cooling as it was, the reaction mixture was diluted with ice water (250 ml). The resulting solid was collected by filtration and washed with water, to give the title compound (4.19 g, 86%) as a pale brown solid.

$^1$H NMR (400 MHz, DMSO-d6) δ ppm; 6.66 (2H, br s), 6.68 (1H, dd, J=2.0, 3.2 Hz), 6.88 (1H, d, J=5.2 Hz), 7.17 (1H, dd, J=0.8, 3.2 Hz), 7.88 (1H, dd, J=0.8, 2.0 Hz), 8.28 (1H, d, J=5.2 Hz); MS m/e (ESI) 162 (MH$^+$).

Reference Example 16

5-bromo-4-(2-furyl)-2-pyrimidinylamine

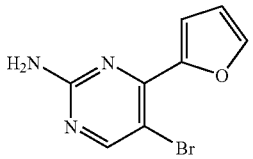

To a solution of 4-(2-furyl)-2-pyrimidinylamine (4.10 g, 25.4 mmol) in N,N-dimethylformamide (40 ml) was added N-bromosuccinimide (4.53 g, 25.5 mmol) at 2° C., followed by stirring as it was. After 6 hours, the reaction mixture was diluted with an aqueous saturated sodium bicarbonate solution (240 ml). The mixture was ice-cooled, and then the crystals were collected by filtration and washed with water, to give the title compound (5.10 g, 84%) as a pale brown solid.

$^1$H NMR (400 MHz, DMSO-d$_6$) δ ppm; 6.73 (1H, dd, J=1.6, 3.6 Hz), 6.96 (2H, br s), 7.50 (1H, dd, J=0.8, 3.6 Hz), 7.97 (1H, dd, J=0.8, 1.6 Hz), 8.41 (1H, s).

Reference Example 17

2-(Benzyloxy)-5-bromopyridine

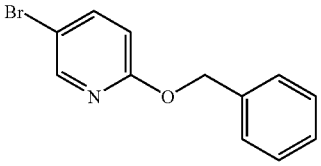

To a solution of benzyl alcohol (11.4 g, 0.105 mol) in N,N-dimethylformamide (250 ml) was added 70% oily sodium hydride (4.2 g, 0.123 mol) at 0° C., followed by stirring as it was for 1.5 hours. Then, 2,5-dibromopyridine (25 g, 0.106 mol) was added thereto, followed by stirring at 70° C. for 2 hours. After cooling as it was, the reaction mixture was diluted with a saturated aqueous ammonium chloride solution and extracted with ethyl acetate. The resulting organic layer was washed with a saturated aqueous ammonium chloride solution twice, dried over anhydrous magnesium sulfate and concentrated, to give a crude product of the title compound (29.5 g) as a pale yellow liquid.

$^1$H NMR (400 MHz, DMSO-d$_6$) δ ppm; 5.33 (2H, s), 6.90 (1H, d, J=9.0 Hz), 7.30-7.41 (3H, m), 7.41-7.46 (2H, m), 7.92 (1H, dd, J=2.8, 9.0 Hz), 8.30 (1H, d, J=2.8 Hz).

Reference Example 18

2-(Benzyloxy)-5-(1,1,1-tributylstanyl)pyridine

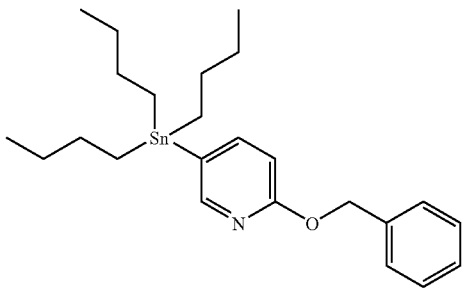

To a suspension of the above crude product (29.5 g) of 2-(benzyloxy)-5-bromopyridine in diethyl ether (300 ml) was dropwise added a 2.66 M solution of n-butyl lithium in hexane (40 ml, 0.106 mol) over 30 minutes at −76° C. to −72° C. under an atmosphere of nitrogen gas. Subsequently, tetrahydrofuran (170 ml) was added dropwise thereto, followed by stirring as it was. After 1.5 hours, a solution of tributyltin chloride (35 g, 0.114 mol) in tetrahydrofuran (50 ml) was added dropwise thereto over 1.5 hours. Then, the reaction mixture was stirred as it was while gradually elevating to room temperature. After 6 hours, the reaction mixture was diluted with a saturated aqueous ammonium chloride solution and ethyl acetate. The resulting organic layer was washed with a saturated aqueous ammonium chloride solution twice, dried over anhydrous sodium sulfate and concentrated. The residue was subjected to silica gel column chromatography (elution solvent; hexane, hexane:ethyl acetate=20:1), to give the title compound (47.0 g, 94%) as a colorless oil.

$^1$H NMR (400 MHz, DMSO-d$_6$) δ ppm; 0.85 (9H, t, J=7.6 Hz), 0.97-1.15 (6H, m), 1.29 (6H, sex, J=7.6 Hz), 1.46-1.55 (6H, m), 5.33 (2H, s), 6.85-6.90 (1H, m), 7.29-7.41 (3H, m), 7.41-7.47 (2H, m), 7.66-7.78 (1H, m), 8.08-8.15 (1H, m).

Reference Example 19

2-(2-Fluoro-4-pyridyl)-1-(2-furyl)-1-ethanone

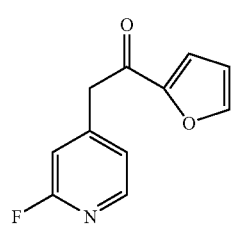

The title compound was synthesized in a similar manner to Reference Example 5 using 2-fluoro-4-methylpyridine.

$^1$H NMR (400 MHz, DMSO-d$_6$) δ ppm; 4.36 (2H, s), 6.76 (1H, dd, J=1.6, 3.6 Hz), 7.11 (1H, br), 7.24-7.29 (1H, m), 7.63 (1H, dd, J=0.4, 3.6 Hz), 8.05 (1H, dd, J=0.8, 1.6 Hz), 8.17 (1H, d, J=4.8 Hz).

Reference Example 20

2-(2-Bromo-4-pyridyl)-1-(2-furyl)-1-ethanone

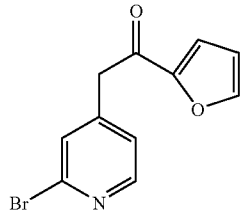

The title compound was synthesized in a similar manner to Reference Example 5 using 2-bromo-4-methylpyridine.

$^1$H NMR (400 MHz, DMSO-$d_6$) δ ppm; 4.31 (2H, s), 6.77 (1H, dd, J=1.6, 3.6 Hz), 7.36 (1H, dd, J=1.6, 5.2 Hz), 7.60 (1H, dd, J=0.4, 1.6 Hz), 7.62 (1H, dd, J=0.8, 3.6 Hz), 8.05 (1H, dd, J=0.8, 1.6 Hz), 8.32 (1H, dd, J=0.4, 5.2 Hz).

Reference Example 21

4,6-Di(2-furyl)-2-pyrimidinamine

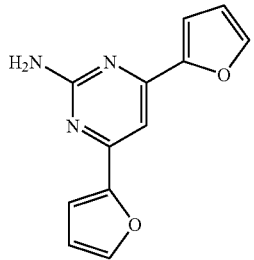

The title compound was synthesized in a similar manner to Reference Example 12 using 2-acetylfuran instead of 1-(2-furyl)-2-(4-pyridyl)-1-lethanone.

$^1$H NMR (400 MHz, DMSO-$d_6$) δ ppm; 6.69 (2H, dd, J=1.6, 3.6 Hz), 6.76 (2H, br s), 7.21 (1H, s), 7.21 (2H, dd, J=0.8, 3.6 Hz), 7.90 (2H, dd, J=0.8, 1.6 Hz).

Reference Example 22

5-Bromo-4,6-di(2-furyl)-2-pyrimidinamine

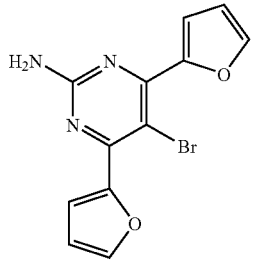

The title compound was synthesized in a similar manner to Reference Example 16 using 4,6-di(2-furyl)-2-pyrimidinamine.

$^1$H NMR (400 MHz, DMSO-$d_6$) δ ppm; 6.72 (2H, dd, J=1.6, 3.6 Hz), 7.01 (2H, br s), 7.47 (2H, dd, J=0.8, 3.6 Hz), 7.95 (2H, dd, J=0.8, 1.6 Hz).

Reference Example 23

Alternative Synthetic Method of Reference Example 9

2-(6-Chloro-3-pyridyl)-1-(2-furyl)-1-ethanone

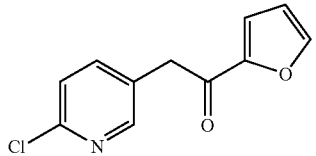

The title compound was obtained in a similar manner to Reference Example 9 using 2-chloro-5-(chloromethyl)pyridine instead of (6-chloro-3-pyridyl)methyl methanesulfonate.

Reference Example 24

2-(6-Chloro-3-pyridyl)-1-(2-thienyl)-1-ethanone

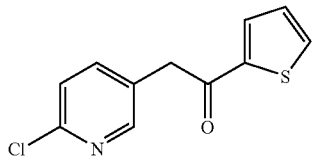

The title compound was obtained in a similar manner to Reference Example 9 using 2-thiophenealdehyde.

$^1$H NMR (400 MHz, DMSO-$d_6$) δ ppm; 4.46 (2H, s), 7.31 (1H, dd, J=4.0, 4.8 Hz), 7.50 (1H, d, J=8.2 Hz), 7.78 (1H, dd, J=2.4, 8.2 Hz), 8.07 (1H, dd, J=1.2, 4.8 Hz), 8.16 (1H, dd, J=1.2, 4.0 Hz), 8.35 (1H, d, J=2.4 Hz).

Reference Example 25

2-(6-Chloro-3-pyridyl)-3-(dimethylamino)-1-(2-thienyl)-2-propen-1-one

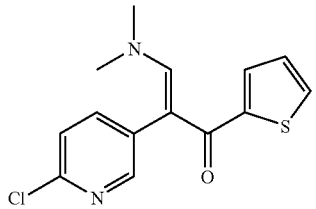

The title compound was obtained in a similar manner to Reference Example 6 using 2-(6-chloro-3-pyridyl)-1-(2-thienyl)-1-ethanone.

$^1$H NMR (400 MHz, DMSO-$d_6$) δ ppm; 2.79 (6H, br s), 7.06 (1H, dd, J=3.8, 5.0 Hz), 7.13 (1H, dd, J=1.0, 3.8 Hz), 7.47 (1H, d, J=8.0 Hz), 7.62 (1H, dd, J=2.4, 8.0 Hz), 7.69 (1H, s), 7.73 (1H, dd, J=1.0, 5.0 Hz), 8.16 (1H, d, J=2.4 Hz).

Reference Example 26

2-(6-Chloro-3-pyridyl)-1-phenyl-1-ethanone

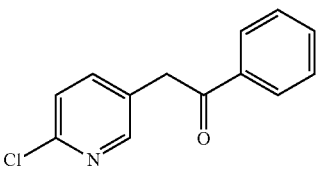

The title compound was obtained in a similar manner to Reference Example 9 using benzaldehyde.

¹H NMR (400 MHz, DMSO-d₆) δ ppm; 4.54 (2H, s), 7.50 (1H, d, J=8.0 Hz), 7.55-7.61 (2H, m), 7.66-7.72 (1H, m), 7.76 (1H, dd, J=2.4, 8.0 Hz), 8.04-8.09 (2H, m), 8.32 (1H, d, J=2.4 Hz).

Reference Example 27

2-(6-chloro-3-pyridyl)-3-(dimethylamino)-1-phenyl-2-propen-1-one

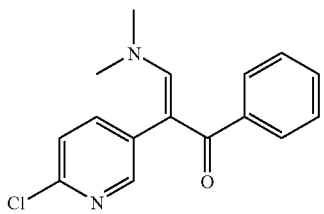

The title compound was obtained in a similar manner to Reference Example 6 using 2-(6-chloro-3-pyridyl)-1-phenyl-1-ethanone.

¹H NMR (400 MHz, DMSO-d₆) δ ppm; 2.73 (6H, br s), 7.29 (1H, s), 7.36-7.45 (6H, m), 7.60 (1H, dd, J=2.2, 8.0 Hz), 8.14 (1H, d, J=2.2 Hz).

Reference Example 28

2-(6-Chloro-3-pyridyl)-1-(3-fluorophenyl)-1-ethanone

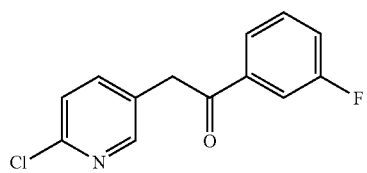

The title compound was obtained in a similar manner to Reference Example 9 using benzaldehyde.

¹H NMR (400 MHz, DMSO-d₆) δ ppm; 4.55 (2H, s), 7.51 (1H, d, J=8.2 Hz), 7.52-7.59 (1H, m), 7.61-7.68 (1H, m), 7.60 (1H, dd, J=2.4, 8.2 Hz), 7.82-7.87 (1H, m), 7.90-7.95 (1H, m), 8.31 (1H, d, J=2.4 Hz).

Reference Example 29

2-(6-Chloro-3-pyridyl)-3-(dimethylamino)-1-(3-fluorophenyl)-2-propen-1-one

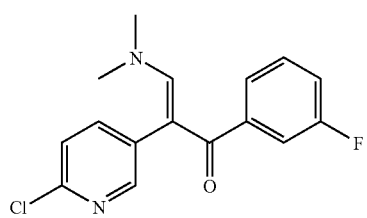

The title compound was obtained in a similar manner to Reference Example 6 using 2-(6-chloro-3-pyridyl)-1-(3-fluorophenyl)-1-ethanone.

¹H NMR (400 MHz, DMSO-d₆) δ ppm; 2.74 (6H, br s), 7.17-7.29 (3H, m), 7.31 (1H, s), 7.39-7.47 (2H, m), 7.61 (1H, dd, J=2.2, 8.0 Hz), 8.15 (1H, d, J=2.2 Hz).

Example 1

4-Chloro-6-(3-fluorophenyl)-5-(4-pyridyl)-2-pyrimidinylamine

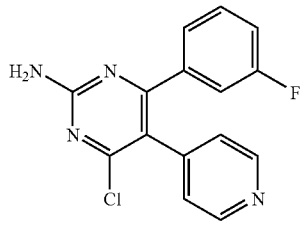

A suspension of 2-amino-6-(3-fluorophenyl)-5-(4-pyridyl)-3,4-dihydro-4-pyrimidinone (1.0 g, 3.54 mmol) in phosphorus oxychloride (15 ml) was stirred at 100° C. for 30 minutes under an atmosphere of nitrogen gas. After cooling as it was, the reaction mixture was concentrated and the residue was dissolved in ethyl acetate and 2N sodium hydroxide. The organic layer was washed with an aqueous saturated sodium bicarbonate solution twice and brine, dried over anhydrous sodium sulfate and concentrated. To the residue was added diethyl ether, and the resulting precipitates were collected by filtration and washed with diethyl ether, to give the title compound (513 mg, 48%) as a colorless solid.

¹NMR (400 MHz, DMSO-d₆) δ ppm; 7.00-7.03 (1H, m), 7.05-7.10 (1H, m), 7.12-7.18 (1H, m), 7.24-7.31 (1H, m), 7.25 (2H, dd, J=1.6, 4.4 Hz), 8.51 (2H, dd, J=1.6, 4.4 Hz); MS m/e (ESI) 301 (MH⁻).

Example 2

4-Chloro-6-(2-furyl)-5-(4-pyridyl)-2-pyrimidinylamine

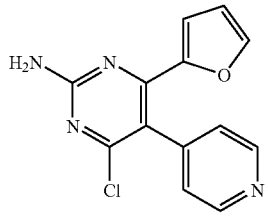

The title compound was synthesized in a similar manner to Example 1 using 2-amino-6-(2-furyl)-5-(4-pyridyl)-3,4-dihydro-4-pyrimidinon e.

¹H NMR (400 MHz, DMSO-d₆) δ ppm; 6.27 (1H, d, J=3.6 Hz), 6.48 (1H, dd, J=2.0, 3.6 Hz), 7.34 (2H, dd, J=1.6, 4.4 Hz), 7.35 (2H, br s), 7.67 (1H, dd, J=0.8, 2.0 Hz), 8.66 (2H, dd, J=1.6, 4.4 Hz); MS m/e (ESI) 273 (MH⁺).

Example 3

4-(3-Fluorophenyl)-6-methoxy-5-(4-pyridyl)-2-pyrimidinylamine

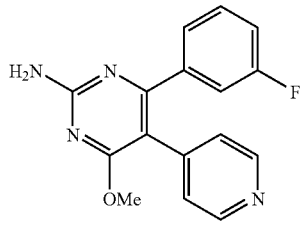

After sodium (20 mg, 0.870 mmol) was dissolved in methanol (3 ml), 4-chloro-6-(3-fluorophenyl)-5-(4-pyridyl)-

2-pyrimidinylamine (50 mg, 0.166 mmol) was added thereto and the mixture was stirred under an atmosphere of nitrogen gas at 60 to 65° C. for 30 minutes. After cooling as it was, the reaction mixture was diluted with ethyl acetate. Then, the mixture was washed with an aqueous ammonium chloride solution thrice and brine, dried over anhydrous sodium sulfate and concentrated. To the residue was added diethyl ether, and the resulting precipitates were collected by filtration and washed with diethyl ether, to give the title compound (16 mg, 32%) as a colorless solid.

$^1$H NMR (400 MHz, DMSO-$d_6$) δ ppm; 3.83 (3H, s), 6.90-7.16 (7H, m), 7.22-7.29 (1H, m), 8.40 (2H, d, J=4.8 Hz); MS m/e (ESI) 297 (MH$^+$).

Example 4

4-Ethoxy-6-(3-fluorophenyl)-5-(4-pyridyl)-2-pyrimidinylamine

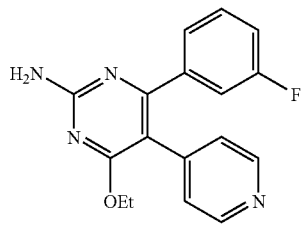

The title compound was synthesized in a similar manner to Example 3 using ethanol.

$^1$H NMR (400 MHz, DMSO-$d_6$) δ ppm; 1.23 (3H, t, J=7.2 Hz), 4.33 (2H, q, J=7.2 Hz), 6.92 (2H, br s), 6.94-7.16 (5H, m), 7.22-7.29 (1H, m), 8.39 (2H, d, J=6.0 Hz); MS m/e (ESI) 311 (MH$^+$).

Example 5

4-(3-Fluorophenyl)-6-propoxy-5-(4-pyridyl)-2-pyrimidinylamine

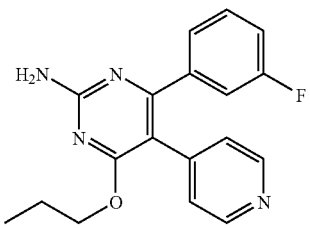

The title compound was synthesized in a similar manner to Example 3 using 1-propanol.

$^1$H NMR (400 MHz, DMSO-$d_6$) δ ppm; 0.86 (3H, t, J=7.2 Hz), 1.62 (2H, sex, J=7.2 Hz), 4.22 (2H, t, J=7.2 Hz), 6.92 (2H, br s), 6.96-7.00 (1H, m), 7.02-7.16 (2H, m), 7.08 (2H, dd, J=1.6, 4.4 Hz), 7.23-7.29 (1H, m), 8.40 (2H, dd, J=1.6, 4.4 Hz); MS m/e (ESI) 325 (MH$^+$).

Example 6

4-(3-Fluorophenyl)-6-isopropoxy-5-(4-pyridyl)-2-pyrimidinylamine

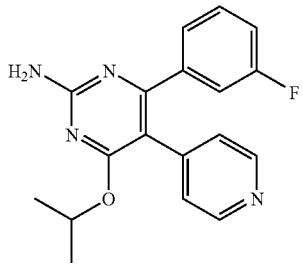

The title compound was synthesized in a similar manner to Example 3 using 2-propanol.

$^1$H NMR (400 MHz, DMSO-$d_6$) δ ppm; 1.23 (6H, d, J=6.0 Hz), 5.32 (1H, m), 6.89 (2H, br s), 6.92-7.16 (5H, m), 7.21-7.28 (1H, m), 8.38 (2H, br); MS m/e (ESI) 325 (MH$^+$).

Example 7

4-Ethoxy-6-(2-furyl)-5-(4-pyridyl)-2-pyrimidinylamine

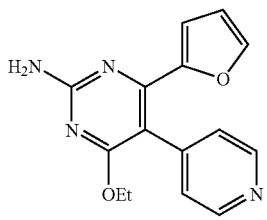

The title compound was synthesized in a similar manner to Example 3 using 4-chloro-6-(2-furyl)-5-(4-pyridyl)-2-pyrimidinylamine and ethanol.

$^1$H NMR (400 MHz, DMSO-$d_6$) δ ppm; 1.17 (3H, t, J=6.8 Hz), 4.28 (2H, q, J=6.8 Hz), 6.36 (1H, dd, J=0.8, 3.6 Hz), 6.45 (1H, dd, J=1.6, 3.6 Hz), 6.81 (2H, br s), 7.19 (2H, d, J=4.4 Hz), 7.57 (1H, dd, J=0.8, 1.6 Hz), 8.54 (2H, d, J=4.4 Hz); MS m/e (ESI) 283 (MH$^+$).

Example 8

4-(2-Furyl)-6-propoxy-5-(4-pyridyl)-2-pyrimidinylamine

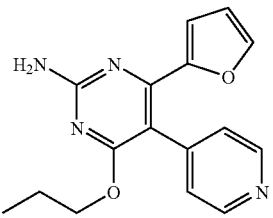

The title compound was synthesized in a similar manner to Example 3 using 4-chloro-6-(2-furyl)-5-(4-pyridyl)-2-pyrimidinylamine and 1-propanol.

$^1$H NMR (400 MHz, DMSO-$d_6$) δ ppm; 0.80 (3H, t, J=7.2 Hz), 1.56 (2H, sex, J=7.2 Hz), 4.17 (2H, t, J=7.2 Hz), 6.38 (1H, dd, J=0.8, 3.6 Hz), 6.45 (1H, dd, J=1.6, 3.6 Hz), 6.80 (2H, br s), 7.19 (2H, dd, J=1.6, 4.4 Hz), 7.57 (1H, dd, J=0.8, 1.6 Hz), 8.54 (2H, dd, J=1.6, 4.4 Hz); MS m/e (ESI) 297 (MH$^+$).

Example 9

4-(2-Furyl)-6-isopropoxy-5-(4-pyridyl)-2-pyrimidinylamine

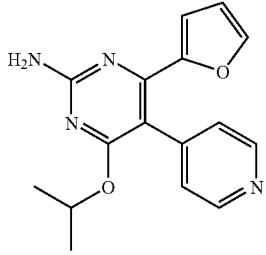

The title compound was synthesized in a similar manner to Example 3 using 4-chloro-6-(2-furyl)-5-(4-pyridyl)-2-pyrimidinylamine and 2-propanol.

$^1$H NMR (400 MHz, DMSO-$d_6$) δ ppm; 1.17 (6H, d, J=6.4 Hz), 5.28 (1H, sept, J=6.4 Hz), 6.35 (1H, dd, J=0.8, 3.6 Hz), 6.45 (1H, dd, J=1.6, 3.6 Hz), 6.78 (2H, br s), 7.17 (2H, dd, J=1.6, 4.4 Hz), 7.56 (1H, dd, J=0.8, 1.6 Hz), 8.53 (2H, dd, J=1.6, 4.4 Hz); MS m/e (ESI) 297 (MH$^+$).

Example 10

4-(Allyloxy)-6-(2-furyl)-5-(4-pyridyl)-2-pyrimidinylamine

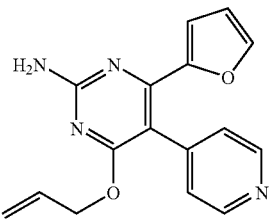

The title compound was synthesized in a similar manner to Example 3 using 4-chloro-6-(2-furyl)-5-(4-pyridyl)-2-pyrimidinylamine and allyl alcohol.

$^1$H NMR (400 MHz, DMSO-$d_6$) δ ppm; 4.77 (2H, dt, J=1.6, 5.2 Hz), 5.12 (1H, dq, J=1.6, 10.4 Hz), 5.14 (1H, dq, J=1.6, 17.2 Hz), 5.93 (1H, ddt, J=5.2, 10.4, 17.2 Hz), 6.38 (1H, dd, J=0.8, 3.4 Hz), 6.46 (1H, dd, J=1.6, 3.4 Hz), 6.84 (2H, br s), 7.21 (2H, dd, J=1.6, 4.4 Hz), 7.57 (1H, dd, J=0.8, 1.6 Hz), 8.55 (2H, dd, J=1.6, 4.4 Hz); MS m/e (FAB) 295 (MH$^+$).

Example 11

4-(2-Furyl)-6-methyl-5-(4-pyridyl)-2-pyrimidinylamine hydrochloride

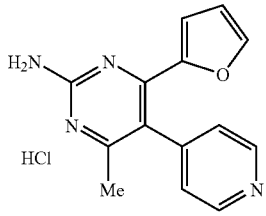

The title compound was synthesized in a similar manner to Method 2 of Reference Example 10 using (E)-4-(2-furyl)-3-(4-pyridyl)-3-buten-2-one. $^1$H NMR (400 MHz, DMSO-$d_6$) δ ppm; 2.09 (3H, s), 6.53 (1H, dd, J=1.6, 3.6 Hz), 6.66 (1H, dd, J=0.8, 3.6 Hz), 7.63 (1H, dd, J=0.8, 1.6 Hz), 7.85 (2H, dd, J=1.2, 5.2 Hz), 8.90 (2H, dd, J=1.2, 5.2 Hz).

Example 12

4,6-Di(2-furyl)-5-(4-pyridyl)-2-pyrimidinylamine

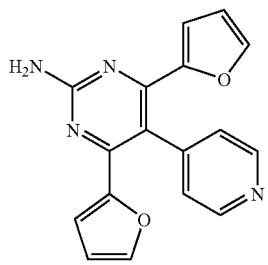

After dissolving sodium (540 mg, 23.5 mmol) in anhydrous ethanol (200 ml), 1-(2-furyl)-2-(4-pyridyl)-1-ethanone (2.00 g, 10.7 mmol) and 2-furaldehyde (0.97 ml, 11.7 mmol) were successively added thereto and the mixture was stirred at room temperature. After 1.5 hours, guanidine hydrochloride (7.0 g, 73.3 mmol) was added thereto, followed by heating under reflux for 14 hours. After cooling as it was, the reaction mixture was concentrated and the residue was suspended in tetrahydrofuran. Then, the insoluble matters were filtered off and washed with tetrahydrofuran, and the solvent of the filtrate was evaporated. To the residue were added tetrahydrofuran (80 ml) and active manganese dioxide (30.0 g), followed by heating under reflux for 2 hours. After cooling as it was, the manganese dioxide was filtered off through Celite and washed with tetrahydrofuran. The combined filtrates were concentrated, and then methanol was added to the residue. The resulting precipitates were collected by filtration and washed with methanol, to give the title compound (1.32 g, 41%) as a pale brown solid.

$^1$H NMR (400 MHz, DMSO-$d_6$) δ ppm; 6.06 (2H, dd, J=0.8, 3.4 Hz), 6.44 (2H, dd, J=1.8, 3.4 Hz), 6.96 (2H, br s), 7.33 (2H, dd, J=1.6, 4.4 Hz), 7.65 (2H, dd, J=0.8, 1.8 Hz), 8.66 (2H, dd, J=1.6, 4.4 Hz).

Example 13

4-(2-Furyl)-6-phenyl-5-(4-pyridyl)-2-pyrimidinylamine

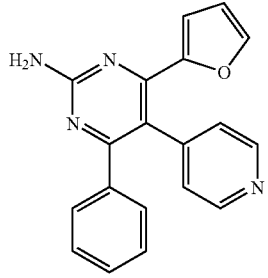

The title compound was synthesized in a similar manner to Example 12 using benzaldehyde.

$^1$H NMR (400 MHz, DMSO-$d_6$) δ ppm; 6.19 (1H, dd, J=0.8, 3.6 Hz), 6.46 (1H, dd, J=1.6, 3.6 Hz), 6.99 (2H, br s), 7.14 (2H, dd, J=1.6, 4.4 Hz), 7.17-7.27 (5H, m), 7.64 (1H, dd, J=0.8, 1.6 Hz), 8.43 (2H, dd, J=1.6, 4.4 Hz).

Example 14

5-(6-Chloro-3-pyridyl)-4-(2-furyl)-2-pyrimidinylamine

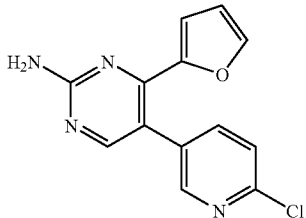

A suspension of 2-(6-chloro-3-pyridyl)-3-(dimethylamino)-1-(2-furyl)-2-propen-1-one (7.49 g, 27.1 mmol), guanidine hydrochloride (7.7 g, 81.0 mmol) and potassium carbonate (22.4 g, 162 mmol) in N,N-dimethylformamide (105 ml) was stirred at 70° C. for 21 hours. After cooling as it was, the reaction mixture was diluted with water. The resulting crystals were collected by filtration and washed with water, to give the title compound (5.48 g, 74%) as a pale yellow solid.

$^1$H NMR (400 MHz, DMSO-$d_6$) δ ppm; 6.56 (1H, dd, J=1.6, 3.6 Hz), 6.71 (1H, dd, J=0.8, 3.6 Hz), 6.96 (2H, br s), 7.55 (1H, dd, J=0.6, 8.4 Hz), 7.69 (1H, dd, J=0.8, 1.6 Hz), 7.77 (1H, dd, J=2.8, 8.4 Hz), 8.22 (1H, s), 8.31 (1H, dd, J=0.6, 2.8 Hz).

Example 15

5-[2-Amino-4-(2-furyl)-5-pyrimidinyl]-1,2-dihydro-2-pyridinone

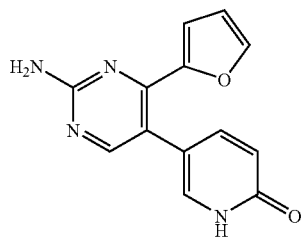

After sodium (455 mg, 19.8 mmol) was dissolved in 4-methoxybenzyl alcohol (15 ml) at 90° C. under an atmosphere of nitrogen gas, 5-(6-chloro-3-pyridyl)-4-(2-furyl)-2-pyrimidinylamine (1.80 g, 6.60 mmol) was added thereto and the mixture was stirred as it was. After 1.5 hours, the reaction mixture was cooled as it was and then diluted with an aqueous saturated ammonium chloride solution and ethyl acetate. The resulting organic layer was washed with an aqueous saturated ammonium chloride solution, dried over anhydrous sodium sulfate and concentrated. Trifluoroacetic acid (40 ml) was added to the residue, followed by stirring at 65° C. After 18 hours, the reaction mixture was cooled as it was and diluted with dichloromethane, water and 5N hydrochloride. The resulting aqueous layer was washed with ethyl acetate and adjusted to pH 6 with 5N sodium hydroxide. The resulting crystals were collected by filtration and washed with water, to give crude crystals of the title compound. The resulting crude crystals were suspended in ethyl acetate, collected by filtration and washed with ethyl acetate, to give the title compound (820 mg, 49%) as a colorless solid.

$^1$H NMR (400 MHz, DMSO-$d_6$) δ ppm; 6.33 (1H, d, J=9.2 Hz), 6.58 (1H, dd, J=1.8, 3.6 Hz), 6.69 (1H, dd, J=0.8, 3.6 Hz), 6.79 (2H, br s), 7.24 (1H, dd, J=2.8., 9.2 Hz), 7.34 (1H, d, J=2.8 Hz), 7.77 (1H, dd, J=0.8, 1.8 Hz), 8.12 (1H, s); MS m/e (ESI) 255 (MH$^+$).

Example 16

5-[2-Amino-4-(2-furyl)-5-pyrimidinyl]-1-methyl-1,2-dihydro-2-pyridinone

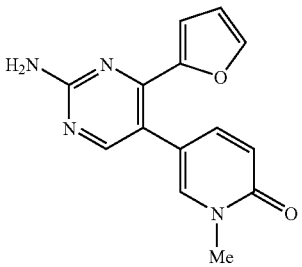

To a suspension of 5-[2-amino-4-(2-furyl)-5-pyrimidinyl]-1,2-dihydro-2-pyridinone (2.2 g, 8.65 mmol) in methanol (44 ml) was added sodium methoxide (940 mg, 17.4 mmol) at room temperature under an atmosphere of nitrogen gas, followed by stirring. After 15 minutes, iodomethane (1.6 ml, 25.7 mmol) was added thereto, followed by stirring as it was for 22 hours. After concentrating the reaction mixture, water was added to the residue. Then, the precipitates were collected by filtration and washed with water, to give the crude crystals of the title compound (1.98 g). The crude crystals were suspended in ethanol, and then the precipitates were collected by filtration and washed with ethanol, to give the title compound (1.54 g, 66%) as a pale yellow solid.

$^1$H NMR (400 MHz, DMSO-$d_6$) δ ppm; 3.46 (3H, s), 6.38 (1H, d, J=9.2 Hz), 6.58 (1H, dd, J=1.6, 3.6 Hz), 6.73 (1H, dd, J=0.8, 3.6 Hz), 6.81 (2H, br s), 7.21 (1H, dd, J=2.6, 9.2 Hz), 7.75 (1H, d, J=2.6 Hz), 7.77 (1H, dd, J=0.8, 1.6 Hz), 8.14 (1H, s); MS m/e (ESI) 269 (MH$^+$).

Example 17

5-[2-Amino-4-(2-furyl)-5-pyrimidinyl]-1-ethyl-1,2-dihydro-2-pyridinone

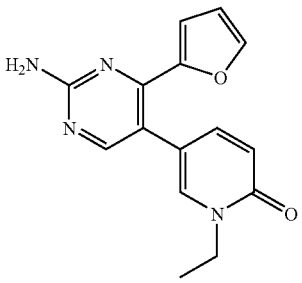

The title compound was synthesized in a similar manner to Example 16 using ethyl iodide.

$^1$H NMR (400 MHz, DMSO-$d_6$) δ ppm; 1.24 (3H, t, J=7.2 Hz), 3.93 (2H, q, J=7.2 Hz), 6.38 (1H, d, J=9.2 Hz), 6.58 (1H, dd, J=1.6, 3.2 Hz), 6.71 (1H, d, J=3.2 Hz), 6.82 (2H, br s), 7.23 (1H, dd, J=2.8, 9.2 Hz), 7.73 (1H, d, J=2.8 Hz), 7.78 (1H, d, J=1.6 Hz), 8.17 (1H, s); MS m/e (ESI) 283 (MH$^+$).

Example 18

1-Allyl-5-[2-amino-4-(2-furyl)-5-pyrimidinyl]-1,2-dihydro-2-pyridinone

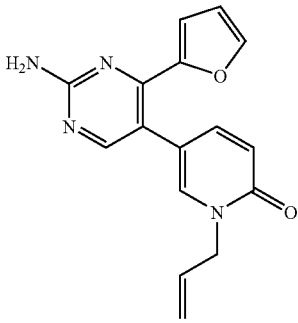

The title compound was synthesized in a similar manner to Example 16 using allyl bromide.

$^1$H NMR (400 MHz, DMSO-d$_6$) δ ppm; 4.53 (2H, d, J=5.2 Hz), 5.10 (1H, dd, J=1.6, 17.2 Hz), 5.19 (1H, dd, J=1.6, 10.4 Hz), 5.97 (1H, ddt, J=5.2, 10.4, 17.2 Hz), 6.42 (1H, d, J=9.2 Hz), 6.58 (1H, dd, J=1.8, 3.6 Hz), 6.73 (1H, dd, J=0.8, 3.6 Hz), 6.82 (2H, br s), 7.27 (1H, dd, J=2.2, 9.2 Hz), 7.64 (1H, d, J=2.2 Hz), 7.76 (1H, dd, J=0.8, 1.8 Hz), 8.14 (1H, s).

Example 19

5-[2-Amino-4-(2-thienyl)-5-pyrimidinyl]-1,2-dihydro-2-pyridinone

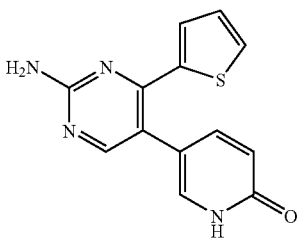

The title compound was synthesized in a similar manner to Example 15 using 5-(6-chloro-3-pyridyl)-4-(2-thienyl)-2-pyrimidinylamine.

$^1$H NMR (400 MHz, DMSO-d$_6$) δ ppm; 6.36 (1H, d, J=9.2 Hz), 6.77 (2H, br s), 7.05 (1H, dd, J=3.6, 4.8 Hz), 7.13 (1H, dd, J=1.2, 3.6 Hz), 7.26 (1H, dd, J=2.4, 9.2 Hz), 7.39 (1H, d, J=2.4 Hz), 7.68 (1H, dd, J=1.2, 4.8 Hz), 8.10 (1H, s).

Example 20

5-[2-Amino-4-(2-thienyl)-5-pyrimidinyl]-1-methyl-1,2-dihydro-2-pyridinone

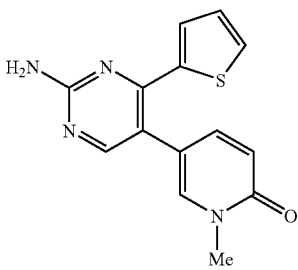

The title compound was synthesized in a similar manner to Example 16 using 5-[2-amino-4-(2-thienyl)-5-pyrimidinyl]-1,2-dihydro-2-pyridinone.

$^1$H NMR (400 MHz, DMSO-d$_6$) δ ppm; 3.46 (3H, s), 6.41 (1H, d, J=9.2 Hz), 6.80 (2H, br s), 7.05 (1H, dd, J=3.8, 5.2 Hz), 7.16 (1H, dd, J=1.0, 3.8 Hz), 7.24 (1H, dd, J=2.8, 9.2 Hz), 7.68 (1H, dd, J=1.0, 5.2 Hz), 7.80 (1H, d, J=2.8 Hz), 8.12 (1H, s).

Example 21

5-[2-Amino-4-(3-fluorophenyl)-5-pyrimidinyl]-1,2-dihydro-2-pyridinone

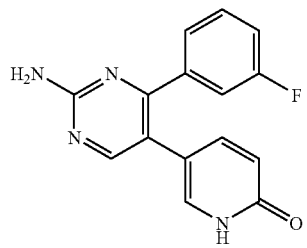

The title compound was synthesized in a similar manner to Example 15 using 5-(6-chloro-3-pyridyl)-4-(3-fluorophenyl)-2-pyrimidinylamine.

$^1$H NMR (400 MHz, DMSO-d$_6$) δ ppm; 6.19 (1H, d, J=9.6 Hz), 6.86 (2H, br s), 7.00 (1H, dd, J=2.8, 9.6 Hz), 7.15-7.30 (4H, m), 7.36-7.46 (1H, m), 8.26 (1H, s), 11.68 (1H, br s); MS m/e (ESI) 283 (MH$^+$).

Example 22

5-[2-Amino-4-(3-fluorophenyl)-5-pyrimidinyl]-1-methyl-1,2-dihydro-2-pyridinone

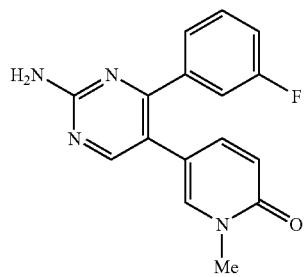

The title compound was synthesized in a similar manner to Example 16 using 5-[2-amino-4-(3-fluorophenyl)-5-pyrimidinyl]-1,2-dihydro-2-pyridinone.

$^1$H NMR (400 MHz, DMSO-d$_6$) δ ppm; 3.42 (3H, s), 6.21 (1H, d, J=9.6 Hz), 6.87 (1H, dd, J=2.8, 9.6 Hz), 6.89 (2H, br s), 7.20-7.29 (3H, m), 7.37-7.44 (1H, m), 7.75 (1H, d, J=2.8 Hz), 8.28 (1H, s).

Example 23

5-(2-Amino-4-phenyl-5-pyrimidinyl)-1,2-dihydro-2-pyridinone

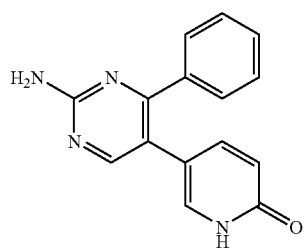

The title compound was synthesized in a similar manner to Example 15 using 5-(6-chloro-3-pyridyl)-4-phenyl-2-pyrimidinylamine.

¹H NMR (400 MHz, DMSO-d₆) δ ppm; 6.16 (1H, d, J=9.6 Hz), 6.80 (2H, br s), 6.96 (1H, dd, J=2.6, 9.6 Hz), 7.23 (1H, d, J=2.6 Hz), 7.34-7.44 (5H, m), 8.23 (1H, s).

Example 24

5-(2-Amino-4-phenyl-5-pyrimidinyl)-1-methyl-1,2-dihydro-2-pyridinone

The title compound was synthesized in a similar manner to Example 16 using 5-(2-amino-4-phenyl-5-pyrimidinyl)-1,2-dihydro-2-pyridinone.

¹H NMR (400 MHz, DMSO-d₆) δ ppm; 3.42 (3H, s), 6.18 (1H, d, J=9.2 Hz), 6.82 (1H, dd, J=2.4, 9.2 Hz), 6.83 (2H, br s), 7.32-7.47 (5H, m), 7.74 (1H, d, J=2.4 Hz), 8.25 (1H, s).

Example 25

5-(6-Chloro-3-pyridyl)-4,6-di(2-furyl)-2-pyrimidinylamine

The title compound was synthesized in a similar manner to Example 12 using 2-(6-chloro-3-pyridyl)-1-(2-furyl)-1-ethanone.

¹H NMR (400 MHz, DMSO-d₆) δ ppm; 6.21 (2H, dd, J=0.6, 3.4 Hz), 6.49 (2H, dd, J=1.8, 3.4 Hz), 6.97 (2H, br s), 7.62 (1H, d, J=8.4 Hz), 7.67 (2H, dd, J=0.6, 1.8 Hz), 7.80 (1H, dd, J=2.4, 8.4 Hz), 8.28 (1H, d, J=2.4 Hz).

Example 26

5-[2-Amino-4,6-di(2-furyl)-5-pyrimidinyl]-1,2-dihydro-2-pyridinone

The title compound was synthesized in a similar manner to Example 15 using 5-(6-chloro-3-pyridyl)-4,6-di(2-furyl)-2-pyrimidinylamine.

¹H NMR (400 MHz, DMSO-d₆) δ ppm; 6.36 (2H, dd, J=0.8, 3.6 Hz), 6.46 (1H, d, J=9.2 Hz), 6.55 (2H, dd, J=1.6, 3.6 Hz), 6.67 (2H, br s), 7.24 (1H, d, J=2.2 Hz), 7.31 (1H, dd, J=2.2, 9.2 Hz), 7.78 (2H, dd, J=0.8, 1.6 Hz), 11.76 (1H, s); MS m/e (ESI) 321 (MH⁺).

Example 27

5-[2-Amino-4,6-di(2-furyl)-5-pyrimidinyl]-1-methyl-1,2-dihydro-2-pyridinone

The title compound was synthesized in a similar manner to Example 16 using 5-[2-amino-4,6-di(2-furyl)-5-pyrimidinyl]-1,2-dihydro-2-pyridinone.

¹H NMR (400 MHz, DMSO-d₆) δ ppm; 3.43 (3H, s), 6.39 (2H, dd, J=0.8, 3.6 Hz), 6.52 (1H, d, J=9.2 Hz), 6.54 (2H, dd, J=1.8, 3.6 Hz), 6.88 (2H, br s), 7.32 (1H, dd, J=2.6, 9.2 Hz), 7.64 (1H, d, J=2.6 Hz), 7.77 (2H, dd, J=0.8, 1.8 Hz); MS m/e (ESI) 335 (MH⁺).

Example 28

6-(3-Fluorophenyl)-5-(6-methoxy-3-pyridyl)-2,4-pyrimidinediamine

The title compound was synthesized in a similar manner to Method 2 of Reference Example 12 using (E)-3-(3-fluorophenyl)-2-(6-methoxy-3-pyridyl)-2-propenenitrile.

¹H NMR (400 MHz, DMSO-d₆) δ ppm; 3.81 (3H, s), 5.96 (2H, br s), 6.12 (2H, br s), 6.74 (1H, d, J=8.6 Hz), 6.92-7.06 (3H, m), 7.18-7.24 (1H, m), 7.41 (1H, dd, J=2.4, 8.6 Hz), 7.80 (1H, d, J=2.4 Hz).

Example 29

5-[2,4-Diamino-6-(3-fluorophenyl)-5-pyrimidinyl]-1,2-dihydro-2-pyridinone

A solution of 6-(3-fluorophenyl)-5-(6-methoxy-3-pyridyl)-2,4-pyrimidinediamine (5.00 g, 16.1 mmol) in acetic acid (30 ml)/concentrated hydrobromic acid (50 ml) was stirred at 100° C. for 1.5 hours. After cooling as it was, the reaction mixture was adjusted to pH 12 to 13 with 5N sodium hydroxide and washed with ethylacetate. The aqueous layer was neutralized with 5N hydrochloric acid. The resulting solid was collected by filtration, to give the title compound (3.36 g, 70%) as a colorless solid.

$^1$H NMR (400 MHz, DMSO-$d_6$) δ ppm; 6.06 (2H, br s), 6.07 (2H, br s), 6.21 (1H, d, J=9.2 Hz), 6.97 (1H, d, J=2.4 Hz), 7.01-7.09 (4H, m), 7.23-7.30 (1H, m); MS m/e (ESI) 298 (MH$^+$).

Example 30

5-[2,4-Diamino-6-(3-fluorophenyl)-5-pyrimidinyl]-1-methyl-1,2-dihydro-2-pyridinone

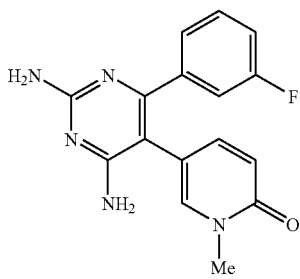

The title compound was synthesized in a similar manner to Example 16 using 5-[2,4-diamino-6-(3-fluorophenyl)-5-pyrimidinyl]-1,2-dihydro-2-pyridinone.

$^1$H NMR (400 MHz, DMSO-$d_6$) δ ppm; 3.32 (3H, s), 6.07 (2H, br s), 6.17 (2H, br s), 6.23 (1H, d, J=9.4 Hz), 6.94 (1H, dd, J=2.6, 9.4 Hz), 7.02-7.12 (3H, m), 7.23-7.30 (1H, m), 7.46 (1H, d, J=2.6 Hz); MS m/e (ESI) 312 (MH$^+$).

Example 31

5-[6-(Benzyloxy)-3-pyridyl]-4-(2-furyl)-2-pyrimidinylamine

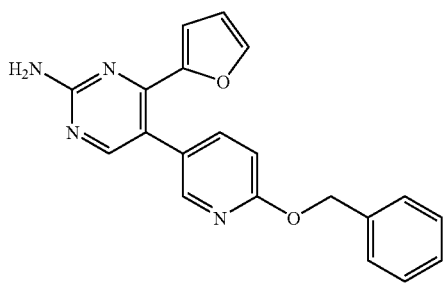

A solution of 5-bromo-4-(2-furyl)-2-pyrimidinylamine (10.5 g, 43.9 mmol), 2-(benzyloxy)-5-(1,1,1-tributylstanyl)-pyridine (41.7 g, 87.9 mmol) and dichlorobis-(triphenylphosphine)palladium (II) (1.6 g, 2.28 mmol) in N,N-dimethylformamide (100 ml) was stirred at 100° C. for 25 hours under an atmosphere of nitrogen gas. After cooling as it was, the reaction mixture was diluted with ethyl acetate and an aqueous saturated ammonium chloride solution. The insoluble matters were filtered off, and then the organic layer in the filtrate was washed with an aqueous saturated ammonium chloride solution twice, dried over anhydrous magnesium sulfate and concentrated. The residue was suspended in hexane, and then the solid was collected by filtration and washed with hexane. The obtained solid was suspended in ethyl acetate, and then collected by filtration and washed with ethyl acetate, to give the title compound (8.35 g, 55%) as a pale orange solid.

$^1$H NMR (400 MHz, DMSO-$d_6$) δ ppm; 5.36 (2H, s), 6.50 (1H, dd, J=0.8, 3.4 Hz), 6.52 (1H, dd, J=1.8, 3.4 Hz), 6.82 (2H, br s), 6.90 (1H, dd, J=0.6, 8.4 Hz), 7.30-7.35 (1H, m), 7.36-7.41 (2H, m), 7.44-7.49 (2H, m), 7.59 (1H, dd, J=2.6, 8.4 Hz), 6.68 (1H, dd, J=0.8, 1.8 Hz), 8.06 (1H, dd, J=0.6, 2.6 Hz), 8.14 (1H, s).

Example 32 (Alternative Synthetic Method of Example 15)

5-[2-Amino-4-(2-furyl)-5-pyrimidinyl]-1,2-dihydro-2-pyridinone

A suspension of 5-[6-(benzyloxy)-3-pyridyl]-4-(2-furyl)-2-pyrimidinylamine (8.35 g, 24.2 mmol) in concentrated hydrochloric acid (40 ml)-water (40 ml) was stirred at 80° C. for 1 hour. After cooling as it was, the reaction mixture was washed with ethyl acetate twice. The aqueous layer was neutralized with an aqueous 5N sodium hydroxide solution. The resulting solid was collected by filtration, washed with water and dried at 50° C. for 14 hours, to give the title compound (5.54 g, 90%) as a pale brown solid.

Example 33

5-[6-(Benzyloxy)-3-pyridyl]-4,6-di(2-furyl)-2-pyrimidinamine

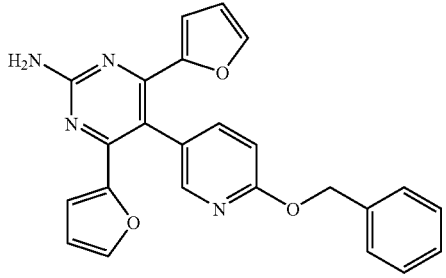

The title compound was synthesized in a similar manner to Example 31 using 5-bromo-4,6-di(2-furyl)-2-pyrimidinamine.

$^1$H NMR (400 MHz, DMSO-$d_6$) δ ppm; 5.42 (2H, s), 5.93 (2H, dd, J=0.4, 3.6 Hz), 6.44 (2H, dd, J=1.6, 3.6 Hz), 6.88 (2H, br s), 7.01 (1H, dd, J=0.4, 8.8 Hz), 7.30-7.51 (5H, m), 7.62 (1H, dd, J=2.4, 8.8 Hz), 7.67 (2H, dd, J=0.4, 1.6 Hz), 7.97 (1H, d, J=2.4 Hz).

Example 34

5-(2-Fluoro-4-pyridyl)-4,6-di(2-furyl)-2-pyrimidinamine

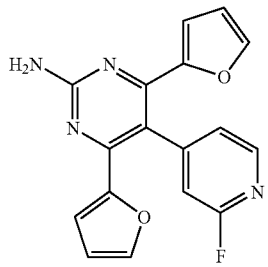

The title compound was synthesized in a similar manner to Example 12 using 2-(2-fluoro-4-pyridyl)-1-(2-furyl)-1-ethanone.

$^1$H NMR (400 MHz, DMSO-$d_6$) δ ppm; 6.33 (2H, dd, J=0.8, 3.6 Hz), 6.48 (2H, dd, J=1.6, 3.6 Hz), 6.99 (2H, br s), 7.21 (1H, br), 7.28-7.32 (1H, m), 7.65 (2H, dd, J=0.8, 1.6 Hz), 8.31 (1H, d, J=5.2 Hz).

Example 35

5-(2-Fluoro-4-pyridyl)-4-(2-furyl)-6-(3-furyl)-2-pyrimidinamine

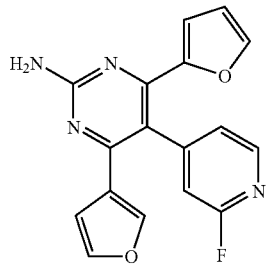

The title compound was synthesized in a similar manner to Example 12 using 2-(2-fluoro-4-pyridyl)-1-(2-furyl)-1-ethanone and 3-furaldehyde.

$^1$H NMR (400 MHz, DMSO-$d_6$) δ ppm; 6.31 (1H, dd, J=0.8, 2.0 Hz), 6.37 (1H, dd, J=0.8, 3.6 Hz), 6.47 (1H, dd, J=1.6, 3.6 Hz), 6.91 (2H, br s), 7.17-7.18 (2H, m), 7.26-7.30 (1H, m), 7.58 (1H, dd, J=1.6, 2.0 Hz), 7.62 (1H, dd, J=0.8, 1.6 Hz), 8.30 (1H, d, J=4.8 Hz).

Example 36

5-(2-Fluoro-4-pyridyl)-4-(2-furyl)-6-(2-thienyl)-2-pyrimidinamine

The title compound was synthesized in a similar manner to Example 12 using 2-(2-fluoro-4-pyridyl)-1-(2-furyl)-1-ethanone and 2-thiophenecarboxyaldehyde.

$^1$H NMR (400 MHz, DMSO-$d_6$) δ ppm; 6.35 (1H, d, J=3.6 Hz), 6.42 (1H, dd, J=0.8, 3.6 Hz), 6.48 (1H, dd, J=1.6, 3.6 Hz), 6.91 (1H, dd, J=3.6, 5.2 Hz), 6.95 (2H, br s), 7.27 (1H, br), 7.34-7.38 (1H, m), 7.61-7.66 (2H, m), 8.34 (1H, d, J=4.8 Hz).

Example 37

5-(2-Fluoro-4-pyridyl)-4-(2-furyl)-6-(3-thienyl)-2-pyrimidinamine

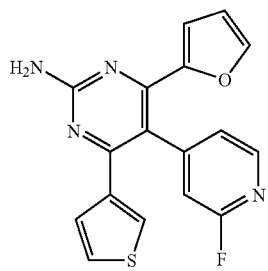

The title compound was synthesized in a similar manner to Example 12 using 2-(2-fluoro-4-pyridyl)-1-(2-furyl)-1-ethanone and 3-thiophenecarboxyaldehyde.

$^1$H NMR (400 MHz, DMSO-$d_6$) δ ppm; 6.39 (1H, dd, J=0.8, 3.6 Hz), 6.48 (1H, dd, J=1.6, 3.6 Hz), 6.94-6.97 (3H, m), 7.07 (1H, br), 7.18-7.20 (1H, m), 7.27 (1H, dd, J=1.2, 2.8 Hz), 7.40 (1H, dd, J=2.8, 5.2 Hz), 7.62 (1H, dd, J=0.8, 1.6 Hz), 8.20 (1H, d, J=5.2 Hz).

Example 38

5-(2-Fluoro-4-pyridyl)-4-(2-furyl)-6-(2-pyridyl)-2-pyrimidinamine

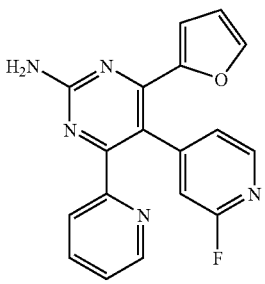

The title compound was synthesized in a similar manner to Example 12 using 2-(2-fluoro-4-pyridyl)-1-(2-furyl)-1-ethanone and 2-pyridinecarboxyaldehyde.

$^1$H NMR (400 MHz, DMSO-$d_6$) δ ppm; 6.43 (1H, dd, J=0.8, 3.6 Hz), 6.50 (1H, dd, J=2.0, 3.6 Hz), 6.89 (1H, br), 7.02-7.04 (1H, m), 7.09 (2H, br s), 7.27 (1H, ddd, J=1.2, 4.8, 7.6 Hz), 7.60 (1H, ddd, J=0.8, 1.2, 7.6 Hz), 7.65 (1H, dd, J=0.8, 2.0 Hz), 7.79 (1H, ddd, J=1.6, 7.6, 7.6 Hz), 8.03 (1H, d, J=5.2 Hz), 8.27 (1H, ddd, J=0.8, 1.6, 4.8 Hz).

Example 39

5-(2-Fluoro-4-pyridyl)-4-(2-furyl)-6-(3-pyridyl)-2-pyrimidinamine

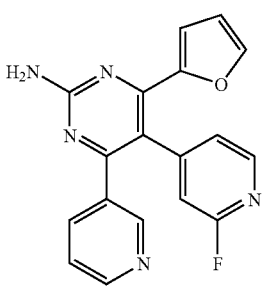

The title compound was synthesized in a similar manner to Example 12 using 2-(2-fluoro-4-pyridyl)-1-(2-furyl)-1-ethanone and 3-pyridinecarboxyaldehyde.

$^1$H NMR (400 MHz, DMSO-$d_6$) δ ppm; 6.48 (1H, d, J=3.6 Hz), 6.51 (1H, dd, J=1.6, 3.6 Hz), 7.05 (1H, br), 7.12 (2H, br s), 7.14-7.18 (1H, m), 7.28 (1H, dd, J=5.2, 8.0 Hz), 7.60 (1H, ddd, J=1.6, 2.0, 8.0 Hz), 7.65 (1H, dd, J=0.8, 1.6 Hz), 8.10 (1H, d, J=4.8 Hz), 8.39 (1H, d, J=2.0 Hz), 8.45 (1H, dd, J=1.6, 5.2 Hz).

Example 40

5-(2-Fluoro-4-pyridyl)-4-(2-furyl)-6-(4-pyridyl)-2-pyrimidinamine

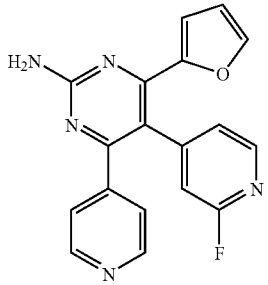

The title compound was synthesized in a similar manner to Example 12 using 2-(2-fluoro-4-pyridyl)-1-(2-furyl)-1-ethanone and 4-pyridinecarboxyaldehyde.

$^1$H NMR (400 MHz, DMSO-$d_6$) δ ppm; 6.48 (1H, d, J=3.6 Hz), 6.51 (1H, dd, J=2.0, 3.6 Hz), 7.05 (1H, s), 7.12-7.18 (1H, m), 7.15 (2H, br s), 7.19 (2H, dd, J=1.6, 4.4 Hz), 7.63-7.67 (1H, m), 8.10 (1H, d, J=5.6 Hz), 8.46 (2H, dd, J=1.6, 4.4 Hz).

Example 41

5-(2-Fluoro-4-pyridyl)-4-(2-furyl)-6-phenyl-2-pyrimidinamine

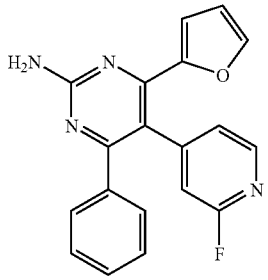

The title compound was synthesized in a similar manner to Example 12 using 2-(2-fluoro-4-pyridyl)-1-(2-furyl)-1-ethanone and benzaldehyde.

$^1$H NMR (400 MHz, DMSO-$d_6$) δ ppm; 6.44 (1H, d, J=3.2 Hz), 6.49 (1H, dd, J=1.6, 3.2 Hz), 6.97 (1H, br), 7.02 (2H, br s), 7.07-7.12 (1H, m), 7.16-7.29 (5H, m), 7.60-7.64 (1H, m), 8.07 (1H, d, J=5.2 Hz).

Example 42

5-(2-Bromo-4-pyridyl)-4,6-di(2-furyl)-2-pyrimidinamine

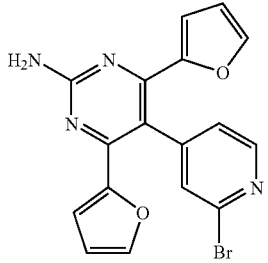

The title compound was synthesized in a similar manner to Example 12 using 2-(2-bromo-4-pyridyl)-1-(2-furyl)-1-ethanone.

$^1$H NMR (400 MHz, DMSO-$d_6$) δ ppm; 6.33 (2H, dd, J=0.8, 3.6 Hz), 6.49 (2H, dd, J=1.6, 3.6 Hz), 6.97 (2H, br s), 7.40 (1H, dd, J=1.6, 4.8 Hz), 7.63 (1H, dd, J=0.8, 1.6 Hz), 7.64 (2H, dd, J=0.8, 1.6 Hz), 8.44 (1H, dd, J=0.8, 4.8 Hz).

Example 43

5-[2-(Dimethylamino)-4-pyridyl]-4,6-di(2-furyl)-2-pyrimidinamine

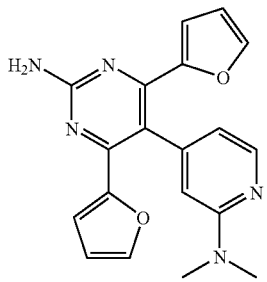

In an autoclave, 5-(2-fluoro-4-pyridyl)-4,6-di(2-furyl)-2-pyrimidinamine (200 mg, 0.621 mmol) was suspended in 1,2-dimethoxyethane (10 ml) and then a 50% dimethylamine aqueous solution (5 ml) was added thereto, followed by stirring at 70° C. After 11 hours, the reaction mixture was extracted with ethyl acetate, and the extract was washed with water and brine, dried over anhydrous sodium sulfate and then the filtrate was concentrated. The resulting solid was suspended in ethanol, collected by filtration and washed with ethanol, to give the title compound (92 mg, 43%) as a pale yellow solid.

$^1$H NMR (400 MHz, DMSO-$d_6$) δ ppm; 2.99 (6H, s), 6.02 (2H, d, J=3.2 Hz), 6.44 (2H, dd, J=1.6, 3.2 Hz), 6.49 (1H, dd, J=1.2, 4.8 Hz), 6.54 (1H, s), 6.86 (2H, br s), 7.70 (2H, d, J=1.6 Hz), 8.17 (1H, d, J=4.8 Hz).

Example 44

4,6-Di(furyl)-5-[2-(methylamino)-4-pyridyl]-2-pyridinamine

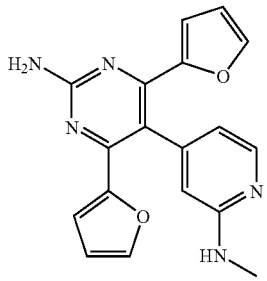

The title compound was synthesized in a similar manner to Example 43 at 70 to 80° C. using a 40% methylamine aqueous solution.

$^1$H NMR (400 MHz, DMSO-$d_6$) δ ppm; 2.78 (3H, d, J=5.2 Hz), 6.07 (2H, d, J=3.6 Hz), 6.30 (1H, s), 6.41 (1H, dd, J=1.2, 5.2 Hz), 6.46 (2H, dd, J=2.0, 3.6 Hz), 6.51 (1H, q, J=5.2 Hz), 6.86 (2H, br s), 7.71 (2H, d, J=2.0 Hz), 8.08 (1H, d, J=5.2 Hz).

Example 45

5-[2-(Ethylamino)-4-pyridyl]-4,6-di(2-furyl)-2-pyrimidinamine

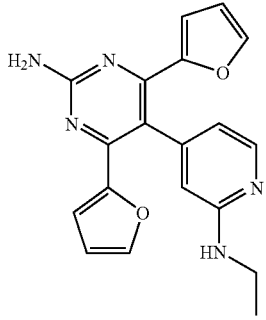

The title compound was synthesized in a similar manner to Example 43 at 80° C. from a 70% ethylamine aqueous solution.

$^1$H NMR (400 MHz, DMSO-$d_6$) δ ppm; 1.12 (3H, t, J=7.2 Hz), 3.23-3.30 (2H, m), 6.07 (2H, dd, J=0.8, 3.2 Hz), 6.30 (1H, dd, J=0.8, 1.2 Hz), 6.41 (1H, dd, J=1.2, 4.8 Hz), 6.46 (2H, dd, J=1.6, 3.2 Hz), 6.47 (1H, t, J=3.2 Hz), 6.86 (2H, br s), 7.72 (2H, dd, J=0.8, 1.6 Hz), 8.07 (1H, dd, J=0.8, 4.8 Hz).

Example 46

4,6-Di(2-furyl)-5-[2-(propylamino)-4-pyridyl]-2-pyrimidinamine

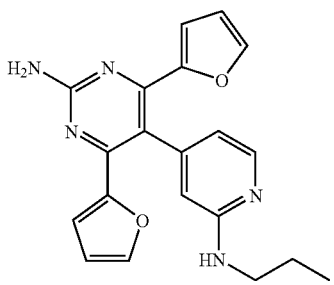

In a reaction vessel, 5-(2-fluoro-4-pyridyl)-4,6-di(2-furyl)-2-pyrimidinamine (200 mg, 0.621 mmol) and n-propylamine (5 ml) were mixed together and the mixture was stirred at 120° C. After 18 hours, the reaction mixture was extracted with ethyl acetate, and the extract was washed with water and brine, dried over anhydrous sodium sulfate and then the filtrate was concentrated. The resulting solid was suspended in ethanol, collected by filtration and washed with ethanol, to give the title compound (64%,72 mg) as a pale yellow solid.

$^1$H NMR (400 MHz, DMSO-$d_6$) δ ppm; 0.89 (3H, t, J=7.2 Hz), 1.47-1.57 (2H, m), 3.18-3.23 (2H, m), 6.07 (2H, dd, J=0.8, 3.2 Hz), 6.31-6.32 (1H, m), 6.39 (1H, dd, J=1.2, 5.2 Hz), 6.46 (2H, dd, J=1.6, 3.2 Hz), 6.51 (1H, t, J=5.6 Hz), 6.86 (2H, br s), 7.72 (2H, dd, J=0.8, 1.6 Hz), 8.06 (1H, dd, J=0.8, 5.2 Hz).

Example 47

5-[2-(Butylamino)-4-pyridyl]-4,6-di(2-furyl)-2-pyrimidinamine

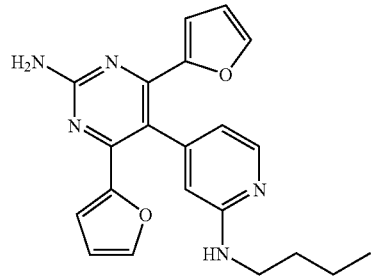

The title compound was synthesized in a similar manner to Example 46 at 80 to 120° C. using n-butylamine.

$^1$H NMR (400 MHz, DMSO-$d_6$) δ ppm; 0.89 (3H, t, J=7.2 Hz), 1.28-1.37 (2H, m), 1.45-1.53 (2H, m), 3.21-3.26 (2H, m), 6.07 (2H, dd, J=0.8, 3.6 Hz), 6.29-6.30 (1H, m), 6.39 (1H, dd, J=1.2, 5.2 Hz), 6.46 (2H, dd, J=1.6, 3.6 Hz), 6.48 (1H, t, J=5.2 Hz), 6.86 (2H, br s), 7.71 (2H, dd, J=0.8, 1.6 Hz), 8.06 (1H, dd, J=0.8, 5.2 Hz).

Example 48

4,6-Di(2-furyl)-5-[2-(isopropylamino)-4-pyridyl]-2-pyrimidinamine

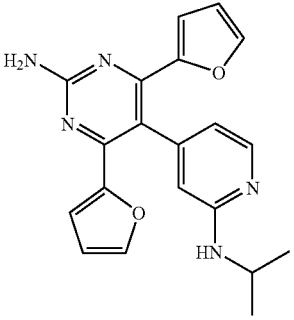

The title compound was synthesized in a similar manner to Example 46 at 120 to 200° C. using i-propylamine.

$^1$H NMR (400 MHz, DMSO-$d_6$) δ ppm; 1.13 (6H, d, J.=6.8 Hz), 3.97-4.05 (1H, m), 6.07 (2H, dd, J=0.8, 3.2 Hz), 6.28 (1H, s), 6.31 (1H, d, J=7.2 Hz), 6.39 (1H, dd, J=1.2, 5.2 Hz), 6.46 (2H, dd, J=1.6, 3.2 Hz), 6.86 (2H, br s), 7.72 (2H, dd, J=0.8, 1.6 Hz), 8.07 (1H, d, J=5.2 Hz).

Example 49

5-(2-Amino-4-pyridyl)-4,6-di(2-furyl)-2-pyrimidinamine

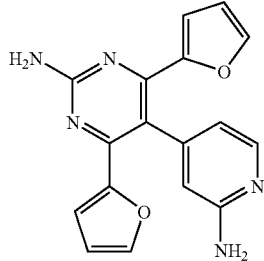

The title compound was synthesized in a similar manner to Example 43 at 80 to 120° C. using 28% aqueous ammonia.

$^1$H NMR (400 MHz, DMSO-$d_6$) δ ppm; 5.98 (2H, br s), 6.08 (2H, d, J=3.2 Hz), 6.29 (1H, br), 6.42 (1H, d, J=5.2 Hz), 6.46 (2H, dd, J=1.6, 3.2 Hz), 6.86 (2H, br s), 7.72 (2H, br), 8.01 (1H, d, J=5.2 Hz).

Example 50

2-(4-[2-Amino-4,6-di(2-furyl)-5-pyrimidinyl]-2-pyridylamino)-1-ethanol

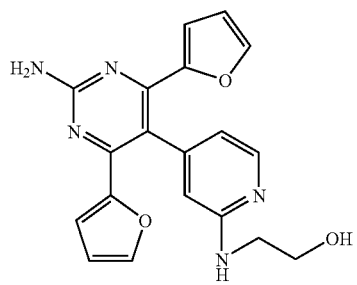

The title compound was synthesized in a similar manner to Example 46 at 120° C. using ethanolamine.

$^1$H NMR (400 MHz, CDCl$_3$) δ ppm; 3.57 (2H, td, J=4.4, 5.2 Hz), 3.84 (2H, t, J=4.4 Hz), 4.88 (1H, t, J=5.2 Hz), 5.28 (2H, br s), 6.08 (2H, dd, J=0.4, 3.6 Hz), 6.33 (2H, dd, J=1.6, 3.6 Hz), 6.38 (1H, br), 6.59 (1H, dd, J=1.2, 5.2 Hz), 7.48 (2H, d, J=1.6 Hz), 8.18 (1H, d, J=5.2 Hz).

Example 51

5-[2-(Benzylamino)-4-pyridyl]-4,6-di(2-furyl)-2-pyrimidinamine

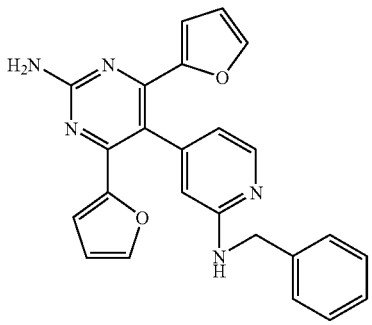

The title compound was synthesized in a similar manner to Example 46 at 120° C. using benzylamine.

$^1$H NMR (400 MHz, DMSO-d$_6$) δ ppm; 4.52 (2H, d, J=6.0 Hz), 6.05 (2H, dd, J=0.8, 3.6 Hz), 6.39 (1H, br), 6.43 (1H, dd, J=1.6, 5.2 Hz), 6.46 (2H, dd, J=1.6, 3.6 Hz), 6.86 (2H, br s), 7.07 (1H, t, J=6.0 Hz), 7.17-7.21 (1H, m), 7.26-7.31 (4H, m), 7.71 (2H, dd, J=0.8, 1.6 Hz), 8.06 (1H, dd, J=0.8, 5.2 Hz).

Example 52

1-{4-[2-Amino-4,6-di(2-furyl)-5-pyrimidinyl]-2-pyridyl}-4-piperidinol

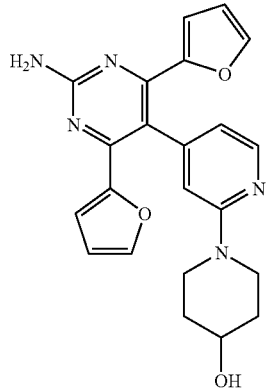

The title compound was synthesized in a similar manner to Example 46 at 120° C. using 4-hydroxypiperidine in 1-methyl-2-pyrrolidinone.

$^1$H NMR (400 MHz, DMSO-d$_6$) δ ppm; 1.25-1.33 (2H, m), 1.69-1.72 (2H, m), 3.03-3.09 (2H, m), 3.67 (1H, br), 3.96-3.99 (2H, m), 4.67 (1H, br d, J=3.2 Hz), 6.03 (2H, dd, J=0.8, 3.2 Hz), 6.44 (2H, dd, J=1.6, 3.2 Hz), 6.51 (1H, dd, J=1.2, 5.2 Hz), 6.76 (1H, br), 6.86 (2H, br s), 7.70 (2H, dd, J=0.8, 1.6 Hz), 8.18 (1H, d, J=5.2 Hz).

Example 53

Ethyl 1-{4-[2-amino-4,6-di(2-furyl)-5-pyrimidinyl]-2-pyridyl}-4-piperidinecarboxylate

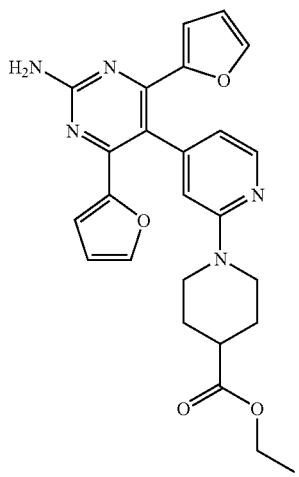

The title compound was synthesized in a similar manner to Example 46 at 120° C. using ethyl isonipecotate.

$^1$H NMR (400 MHz, DMSO-d$_6$) δ ppm; 1.17 (3H, t, J=7.2 Hz), 1.44-1.53 (2H, m), 1.78-1.80 (2H, m), 2.56-2.62 (1H, m), 2.90-2.96 (2H, m), 4.06 (2H, t, J=7.2 Hz), 4.16-4.19 (2H, m), 6.04 (2H, d, J=3.2 Hz), 6.43 (2H, dd, J=1.2, 3.2 Hz), 6.54 (1H, dd, J=0.8, 4.8 Hz), 6.78 (1H, br), 6.87 (2H, br s), 7.69 (2H, d, J=1.2 Hz), 8.19 (1H, d, J=4.8 Hz).

Example 54

N1-{4-[2-Amino-4,6-di(2-furyl)-5-pyrimidinyl]-2-pyridyl}-1,2-ethanediamine

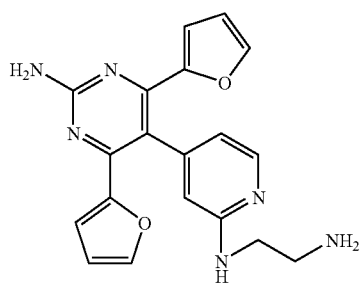

The title compound was synthesized in a similar manner to Example 46 using ethylenediamine under reflux.

$^1$H NMR (400 MHz, CDCl$_3$) δ ppm; 2.93 (2H, t, J=5.6 Hz), 3.36 (2H, td, J=5.6, 5.6 Hz), 4.96 (1H, br t, J=5.6 Hz), 5.30 (2H, br s), 6.06 (2H, dd, J=0.8, 3.6 Hz), 6.31 (2H, dd, J=2.0, 3.6 Hz), 6.34-6.35 (1H, m), 6.55 (1H, dd, J=1.6, 5.2 Hz), 7.49 (2H, dd, J=0.8, 2.0 Hz), 8.22 (1H, dd, J=0.8, 5.2 Hz).

Example 55

N1-{4-[2-Amino-4,6-di(2-furyl)-5-pyrimidinyl]-2-pyridyl}-1,3-propanediamine

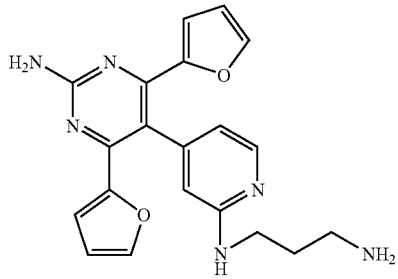

The title compound was synthesized in a similar manner to Example 46 at 120° C. using 1,3-diaminopropane.

1H NMR (400 MHz, CDCl$_3$) δ ppm; 1.74 (2H, tt, J=6.8, 6.8 Hz), 2.83 (2H, t, J=6.8 Hz), 3.37 (2H, dt, J=5.2, 6.8 Hz), 5.08 (1H, br t, J=5.2 Hz), 5.28 (2H, br s), 6.06 (2H, dd, J=0.8, 3.6 Hz), 6.30-6.32 (1H, m), 6.31 (2H, dd, J=1.6, 3.6 Hz), 6.53 (1H, dd, J=1.6, 5.2 Hz), 7.49 (2H, dd, J=0.8, 1.6 Hz), 8.21 (1H, dd, J=0.8, 5.2 Hz).

Example 56

N1-{4-[2-Amino-4,6-di(2-furyl)-5-pyrimidinyl]-2-pyridyl}-1,4-butanediamine

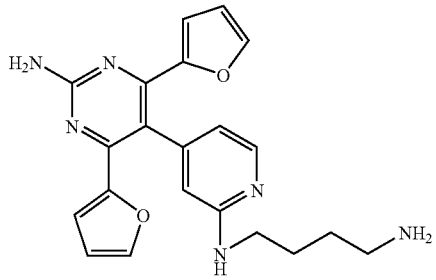

The title compound was synthesized in a similar manner to Example 46 at 120° C. using 1,4-diaminobutane.

$^1$H NMR (400 MHz, CDCl$_3$) δ ppm; 1.49-1.68 (4H, m), 2.71 (2H, t, J=6.8 Hz), 3.27 (2H, t, J=6.4 Hz), 4.77 (1H, br), 5.29 (2H, br s), 6.06 (2H, dd, J=0.8, 3.6 Hz), 6.30-6.32 (1H, m), 6.31 (2H, dd, J=1.6, 3.6 Hz), 6.54 (1H, dd, J=1.2, 5.2 Hz), 7.49 (2H, dd, J=0.8, 1.6 Hz), 8.21 (1H, dd, J=0.8, 5.2 Hz).

Example 57

5-[2-(Dimethylamino)-4-pyridyl]-4-(2-furyl)-6-(3-furyl)-2-pyrimidinamine

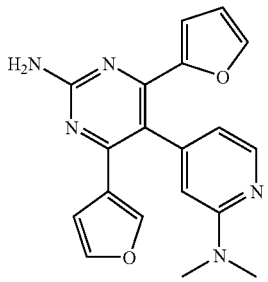

The title compound was synthesized in a similar manner to Example 43 at 80° C. using 5-(2-fluoro-4-pyridyl)-4-(2-furyl)-6-(3-furyl)-2-pyrimidinamine.

$^1$H NMR (400 MHz, DMSO-d$_6$) δ ppm; 2.99 (6H, s), 6.07 (1H, d, J=3.6 Hz), 6.44-6.46 (2H, m), 6.48 (1H, dd, J=1.2, 4.8 Hz), 6.53 (1H, s), 6.76 (2H, br s), 7.14 (1H, s), 7.58 (1H, dd, J=1.2, 1.2 Hz), 7.70 (1H, d, J=1.6 Hz), 8.17 (1H, d, J=5.2 Hz).

Example 58

5-[2-(Dimethylamino)-4-pyridyl]-4-(2-furyl)-6-(2-thienyl)-2-pyrimidinamine

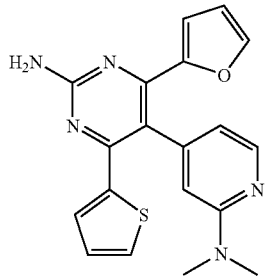

The title compound was synthesized in a similar manner to Example 43 at 80° C. using 5-(2-fluoro-4-pyridyl)-4-(2-furyl)-6-(2-thienyl)-2-pyrimidinamine.

$^1$H NMR (400 MHz, DMSO-d$_6$) δ ppm; 3.00 (6H, s), 6.02 (1H, dd, J=0.8, 3.6 Hz), 6.45 (1H, dd, J=2.0, 3.6 Hz), 6.52 (1H, dd, J=1.2, 5.2 Hz), 6.59 (1H, s), 6.62 (1H, dd, J=1.2, 4.0 Hz), 6.81 (2H, br s), 6.91 (1H, dd, J 4.0, 5.2 Hz), 7.59 (1H, dd, J=1.2, 5.2 Hz), 7.71 (1H, dd, J=0.8, 2.0 Hz), 8.20 (1H, dd, J=0.8, 5.2 Hz).

Example 59

5-[2-(Dimethylamino)-4-pyridyl]-4-(2-furyl)-6-(3-thienyl)-2-pyrimidinamine

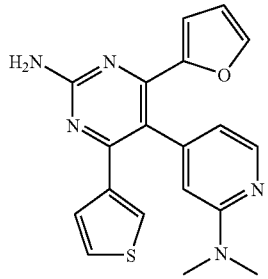

The title compound was synthesized in a similar manner to Example 43 at 80° C. using 5-(2-fluoro-4-pyridyl)-4-(2-furyl)-6-(3-thienyl)-2-pyrimidinamine.

$^1$H NMR (400 MHz, DMSO-d$_6$) δ ppm; 2.94 (6H, s), 6.06 (1H, d, J=3.2 Hz), 6.39-6.46 (3H, m), 6.78 (2H, br s), 7.05 (1H, dd, J=1.2, 4.8 Hz), 7.34-7.39 (2H, m), 7.68 (1H, d, J=1.2 Hz), 8.07 (1H, d, J=4.8 Hz).

Example 60

5-[2-(Dimethylamino)-4-pyridyl]-4-(2-furyl)-6-(2-pyridyl)-2-pyrimidinamine

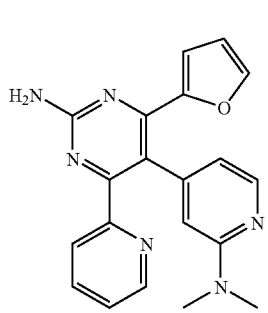

The title compound was synthesized in a similar manner to Example 43 at 80° C. using 5-(2-fluoro-4-pyridyl)-4-(2-furyl)-6-(2-pyridyl)-2-pyrimidinamine.

$^1$H NMR (400 MHz, DMSO-d$_6$) δ ppm; 2.84 (6H, s), 6.19 (1H, dd, J=0.8, 3.2 Hz), 6.26 (1H, br), 6.28 (1H, dd, J=1.2, 5.2

Hz), 6.46 (1H, dd, J=1.6, 3.2 Hz), 6.95 (2H, br s), 7.25 (1H, ddd, J=1.2, 4.8, 7.6 Hz), 7.38-7.40 (1H, m), 7.68-7.73 (2H, m), 7.87 (1H, dd, J=0.4, 5.2 Hz), 8.36-8.38 (1H, m).

Example 61

5-[2-(Dimethylamino)-4-pyridyl]-4-(2-furyl)-6-(3-pyridyl)-2-pyrimidinamine

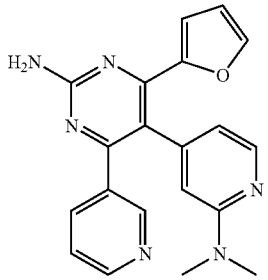

The title compound was synthesized in a similar manner to Example 43 at 80° C. using 5-(2-fluoro-4-pyridyl)-4-(2-furyl)-6-(3-pyridyl)-2-pyrimidinamine.

$^1$H NMR (400 MHz, DMSO-d$_6$) δ ppm; 2.87 (6H, s), 6.17 (1H, dd, J=0.8, 3.6 Hz), 6.36 (1H, dd, J=1.2, 5.2 Hz), 6.39 (1H, br), 6.46 (1H, dd, J=1.6, 3.6 Hz), 6.96 (2H, br s), 7.27 (1H, ddd, J=0.8, 5.2, 8.0 Hz), 7.67 (1H, dt, J=2.0, 8.0 Hz), 7.70 (1H, dd, J=0.8, 1.6 Hz), 7.94 (1H, d, J=5.2 Hz), 8.41-8.45 (2H, m).

Example 62

5-[2-(Dimethylamino)-4-pyridyl]-4-(2-furyl)-6-(4-pyridyl)-2-pyrimidinamine

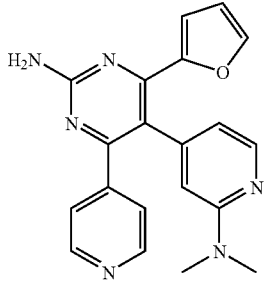

The title compound was synthesized in a similar manner to Example 43 at 80° C. using 5-(2-fluoro-4-pyridyl)-4-(2-furyl)-6-(4-pyridyl)-2-pyrimidinamine.

$^1$H NMR (400 MHz, DMSO-d$_6$) δ ppm; 2.88 (6H, s), 6.17 (1H, d, J=3.6 Hz), 6.36 (1H, d, J=5.2 Hz), 6.39 (1H, s), 6.47 (1H, dd, J=1.6, 3.6 Hz), 7.01 (2H, br s), 7.24 (2H, d, J=5.6 Hz), 7.72 (1H, s), 7.95 (1H, d, J=5.2 Hz), 8.44 (2H, d, J=5.6 Hz).

Example 63

5-[2-(Dimethylamino)-4-pyridyl]-4-(2-furyl)-6-phenyl-2-pyrimidinamine

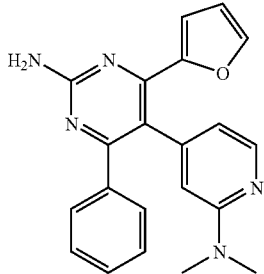

The title compound was synthesized in a similar manner to Example 43 at 80° C. using 5-(2-fluoro-4-pyridyl)-4-(2-furyl)-6-phenyl-2-pyrimidinamine.

$^1$H NMR (400 MHz, DMSO-d$_6$) δ ppm; 2.84 (6H, s), 6.12 (1H, d, J=3.2 Hz), 6.31 (1H, br), 6.32 (1H, br), 6.44 (1H, dd, J=1.6, 3.2 Hz), 6.85 (2H, br s), 7.19-7.26 (5H, m), 7.67-7.68 (1H, m), 7.91 (1H, d, J=5.6 Hz).

Example 64

5-(2-Butoxy-4-pyridyl)-4,6-di(2-furyl)-2-pyrimidinamine

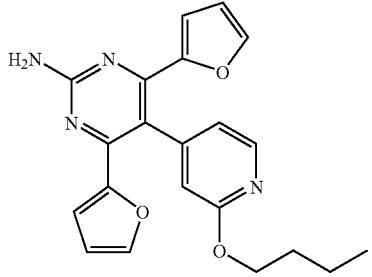

In a reaction vessel, sodium (21 mg, 0.931 mmol) was dissolved in n-butanol (4 ml) and then 5-(2-fluoro-4-pyridyl)-4,6-di(2-furyl)-2-pyrimidinamine (100 mg, 0.310 mmol) was added thereto, followed by stirring under reflux for 5 hours under an atmosphere of nitrogen gas. The reaction was terminated by adding water thereto. Then, the reaction mixture was extracted with ethyl acetate, washed with water and brine, dried over anhydrous sodium sulfate and then the filtrate was concentrated. The resulting solid was suspended in ethanol, collected by filtration and washed with ethanol, to give the title compound (63 mg, 54%) as a pale yellow solid.

$^1$H NMR (400 MHz, DMSO-d$_6$) δ ppm; 0.92 (3H, t, J=7.2 Hz), 1.36-1.45 (2H, m), 1.66-1.73 (2H, m), 4.29 (2H, t, J=6.8 Hz), 6.09 (2H, dd, J=0.8, 3.6 Hz), 6.45 (2H, dd, J=1.6, 3.6 Hz), 6.69 (1H, dd, J=0.8, 1.6 Hz), 6.90 (1H, dd, J=1.6, 5.2 Hz), 6.91 (2H, br s), 7.66 (2H, dd, J=0.8, 1.6 Hz), 8.22 (1H, dd, J=0.8, 5.2 Hz).

Example 65

2-({4-[2-Amino-4,6-di(2-furyl)-5-pyrimidinyl]-2-pyridyl}oxy)-1-ethanol

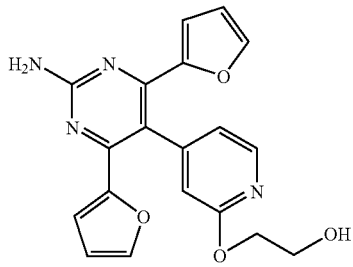

In a reaction vessel, sodium hydride (15 mg, 0.372 mmol) was suspended in N,N-dimethylformamide (4 ml) and ethylene glycol (23 mg, 0.372 mmol) was added thereto, followed by stirring at 80° C. for 30 minutes under an atmosphere of nitrogen gas. Subsequently, 5-(2-fluoro-4-pyridyl)-4,6-di(2-furyl)-2-pyrimidinamine (100 mg, 0.310 mmol) was added thereto, followed by stirring for 14 hours under the same conditions. Then, the reaction was terminated by adding water thereto. The reaction mixture was extracted with ethyl acetate, washed with water and brine, dried over anhydrous sodium sulfate and then the filtrate was concentrated. The resulting crude product was purified by silica gel column chromatography, to give the title compound (41 mg, 36%) as a pale yellow solid.

Example 66

5-[2-Amino-4-(2-furyl)-5-pyrimidinyl]-1-propyl-1,2-dihydro-2-pyridinone

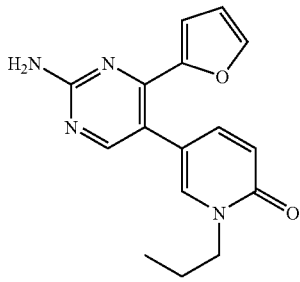

In a reaction vessel, 5-[2-amino-4-(2-furyl)-5-pyrimidinyl]-1,2-dihydro-2-pyridinone (100 mg, 0.393 mmol) and potassium carbonate (109 mg, 0.787 mmol) were suspended in methanol (2 ml). Then, propyl iodide (134 mg, 0.787 mmol) was added thereto, followed by stirring at 50° C. for 17 hours. After the reaction was terminated, the mixture was concentrated and suspended in dimethylsulfoxide. The insoluble matters were removed by filtration and the resulting filtrate was purified by HPLC, to give the title compound (48 mg, 41%) as a pale yellow solid.

$^1$H NMR (400 MHz, DMSO-$d_6$) δ ppm; 0.86 (3H, t, J=7.2 Hz), 1.67 (2H, tq, J=7.2, 7.2 Hz), 3.85 (2H, t, J=7.2 Hz), 6.37 (1H, dd, J=0.4, 9.6 Hz), 6.57 (1H, dd, J=1.6, 3.2 Hz), 6.68 (1H, dd, J=0.8, 3.2 Hz), 6.79 (2H, br s), 7.22 (1H, dd, J=2.4, 9.6 Hz), 7.68 (1H, dd, J=0.4, 2.4 Hz), 7.75 (1H, dd, J=0.8, 1.6 Hz), 8.13 (1H, s).

Example 67

5-[2-Amino-4-(2-furyl)-5-pyrimidinyl]-1-butyl-1,2-dihydro-2-pyridinone

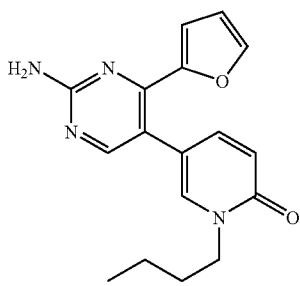

The title compound was synthesized in a similar manner to Example 66 using butyl iodide.

$^1$H NMR (400 MHz, DMSO-$d_6$) δ ppm; 0.89 (3H, t, J=7.2 Hz), 1.28 (2H, tq, J=7.2, 7.2 Hz), 1.63 (2H, dt, J=7.2, 7.2 Hz), 3.88 (2H, t, J=7.2 Hz), 6.37 (1H, d, J=9.2 Hz), 6.57 (1H, dd, J=1.6, 3.6 Hz), 6.68 (1H, d, J=3.6 Hz), 6.79 (2H, br s), 7.22 (1H, dd, J=2.4, 9.2 Hz), 7.68 (1H, d, J=2.4 Hz), 7.73-7.75 (1H, m), 8.13 (1H, s).

Example 68

5-[2-Amino-4-(2-furyl)-5-pyrimidinyl]-1-(2-fluoroethyl)-1,2-dihydro-2-pyridinone

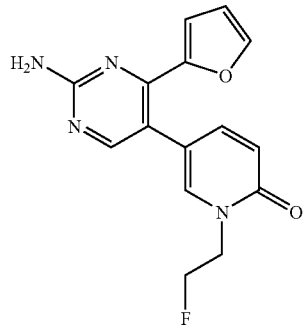

The title compound was synthesized in a similar manner to Example 66 using 1-iodo-2-fluoroethane.

$^1$H NMR (400 MHz, DMSO-$d_6$) δ ppm; 4.24 (2H, dt, J=4.8, 26.0 Hz), 4.70 (2H, dt, J=4.8, 47.2 Hz), 6.42 (1H, d, J=9.2 Hz), 6.57 (1H, dd, J=1.6, 3.6 Hz), 6.70 (1H, dd, J=0.8, 3.6 Hz), 6.81 (2H, br s), 7.27 (1H, dd, J=2.8, 9.2 Hz), 7.68 (1H, d, J=2.8 Hz), 7.74-7.76 (1H, m), 8.11 (1H, s).

Example 69

5-[2-Amino-4-(2-furyl)-5-pyrimidinyl]-1-(8-hydroxyoctyl)-1,2-dihydro-2-pyridinone

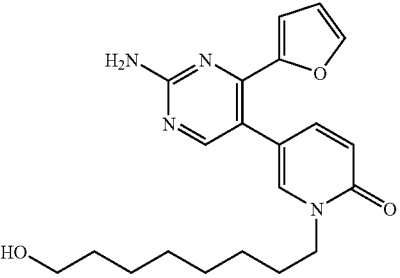

The title compound was synthesized in a similar manner to Example 66 using 8-bromo-1-octanol.

$^1$H NMR (400 MHz, MeOH-$d_4$) δ ppm; 1.20-1.31 (8H, m), 1.37-1.45 (2H, m), 1.62-1.71 (2H, m), 3.42 (2H, t, J=6.8 Hz), 3.92 (2H, t, J=7.2 Hz), 6.42 (1H, dd, J=2.0, 3.6 Hz), 6.46 (1H, d, J=9.2 Hz), 6.75 (1H, d, J=3.6 Hz), 7.27 (1H, dd, J=2.4, 9.2 Hz), 7.46-7.48 (1H, m), 7.53 (1H, d, J=2.4 Hz), 8.03 (1H, s).

Example 70

Methyl 4-{5-[2-amino-4-(2-furyl)-5-pyrimidinyl]-2-oxo-1,2-dihydro-1-pyridinyl}butanoate

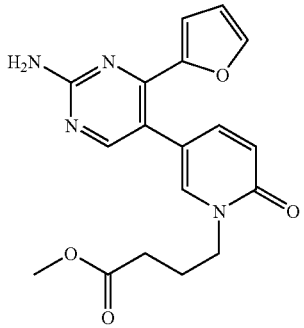

The title compound was synthesized in a similar manner to Example 66 using ethyl 4-bromobutylate.

$^1$H NMR (400 MHz, DMSO-$d_6$) δ ppm; 3.71 (2H, td, J=5.2, 5.2 Hz), 4.30 (2H, t, J=5.2 Hz), 4.84 (1H, t, J=5.2 Hz), 6.09 (2H, d, J=3.2 Hz), 6.45 (2H, dd, J=1.6, 3.2 Hz), 6.71 (1H, br), 6.91-6.92 (3H, m), 7.66 (2H, d, J=1.6 Hz), 8.22 (1H, d, J=5.2 Hz).

Note: The NMR data at the top of the page corresponds to a previous example (not Example 66–70).

¹H NMR (400 MHz, CDCl₃) δ ppm; 2.12 (2H, tt, J=7.2, 7.2 Hz), 2.41 (2H, t, J=7.2 Hz), 3.67 (3H, s), 4.04 (2H, t, J=7.2 Hz), 5.45 (2H, br s), 6.44 (1H, dd, J=1.6, 3.6 Hz), 6.60 (1H, d, J=9.2 Hz), 6.71 (1H, d, J=3.6 Hz), 7.20 (1H, dd, J=2.8, 9.2 Hz), 7.24 (1H, d, J=2.8 Hz), 7.49 (1H, dd, J=0.8, 1.6 Hz), 8.14 (1H, s).

Example 71

5-[2-Amino-4-(2-furyl)-5-pyrimidinyl]-1-(2-propynyl)-1,2-dihydro-2-pyridinone

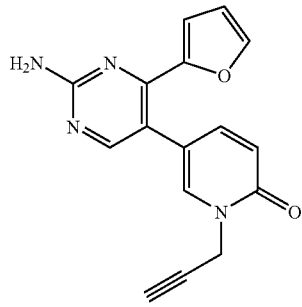

The title compound was synthesized in a similar manner to Example 66 using propargyl bromide.

¹H NMR (400 MHz, CDCl₃) δ ppm; 2.49 (1H, t, J=2.8 Hz), 4.82 (2H, d, J=2.8 Hz), 5.31 (2H, br s), 6.45 (1H, dd, J=1.6, 3.6 Hz), 6.61 (1H, dd, J=0.4, 9.2 Hz), 6.74 (1H, dd, J=0.8, 3.6 Hz), 7.23 (1H, dd, J=2.4, 9.2 Hz), 7.49 (1H, dd, J=0.8, 1.6 Hz), 7.59 (1H, dd, J=0.4, 2.4 Hz), 8.16 (1H, s).

Example 72

5-[2-Amino-4-2-furyl)-5-pyrimidinyl]-1-lisobutyl-1,2-dihydro-2-pyridinone

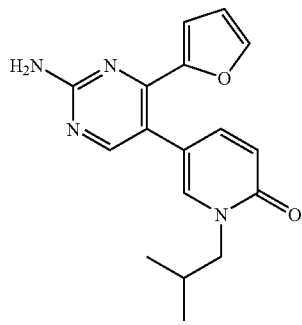

The title compound was synthesized in a similar manner to Example 66 using 1-iodo-2-methylpropane.

¹H NMR (400 MHz, CDCl₃) δ ppm; 0.96 (6H, t, J=7.2 Hz), 2.16-2.27 (1H, m), 3.78 (2H, d, J=7.6 Hz), 5.26 (2H, br s), 6.43 (1H, dd, J=1.6, 3.6 Hz), 6.61 (1H, d, J=9.6 Hz), 6.68 (1H, dd, J=0.8, 3.6 Hz), 7.14 (1H, dd, J=0.4, 2.4 Hz), 7.19 (1H, dd, J=2.4, 9.6 Hz), 7.48 (1H, dd, J=0.8, 1.6 Hz), 8.12 (1H, s).

Example 73

5-[2-Amino-4-(2-furyl)-5-pyrimidinyl]-1-(2-butynyl)-1,2-dihydro-2-pyridinone

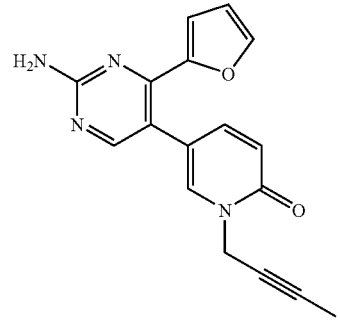

The title compound was synthesized in a similar manner to Example 66 using 1-bromo-2-butyne.

¹H NMR (400 MHz, DMSO-d₆) δ ppm; 1.80 (3H, s), 4.67 (2H, d, J=2.0 Hz), 6.41 (1H, d, J=9.2 Hz), 6.56-6.59 (1H, m), 6.74 (1H, d, J=3.2 Hz), 6.80 (2H, br s), 7.26 (1H, dd, J=2.0, 9.2 Hz), 7.72 (1H, d, J=2.0 Hz), 7.74 (1H, br), 8.13 (1H, s).

Example 74

5-[2-Amino-4-(2-furyl)-5-pyrimidinyl]-1-benzyl-1,2-dihydro-2-pyridinone

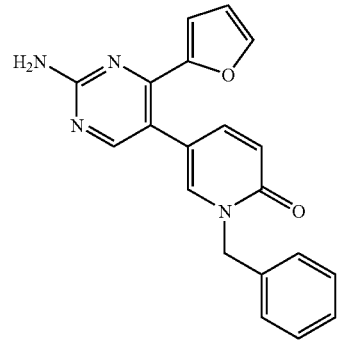

The title compound was synthesized in a similar manner to Example 66 using benzyl chloride.

¹H NMR (400 MHz, CDCl₃) δ ppm; 5.14 (2H, br), 5.18 (2H, s), 6.39 (1H, dd, J=1.6, 3.6 Hz), 6.64-6.68 (2H, m), 7.18-7.23 (2H, m), 7.27-7.36 (5H, m), 7.41 (1H, dd, J=0.8, 1.6 Hz), 8.07 (1H, s).

Example 75

5-[2-Amino-4-(2-furyl)-5-pyrimidinyl]-1-isopentyl-1,2-dihydro-2-pyridinone

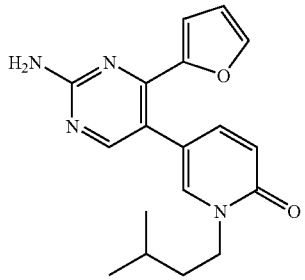

The title compound was synthesized in a similar manner to Example 66 using 1-iodo-3-methylbutane.

¹H NMR (400 MHz, MeOH-d₄) δ ppm; 0.98 (6H, d, J=6.0 Hz), 1.60-1.70 (3H, m), 4.05 (2H, t, J=7.2 Hz), 6.53 (1H, dd, J=1.6, 3.6 Hz), 6.57 (1H, d, J=9.2 Hz), 6.86 (1H, dd, J=0.4, 3.6 Hz), 7.38 (1H, dd, J=2.8, 9.2 Hz), 7.58 (1H, dd, J=0.4, 1.6 Hz), 7.65 (1H, d, J=2.8 Hz), 8.14 (1H, s).

Example 76

5-[2-Amino-4-(2-furyl)-5-pyrimidinyl]-1-(2-methylbutyl)-1,2-dihydro-2-pyridinone

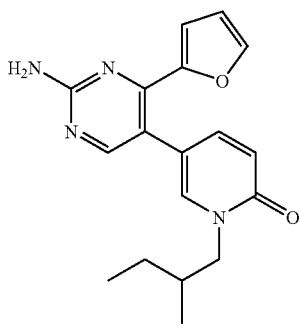

The title compound was synthesized in a similar manner to Example 66 using 1-iodo-2-methylbutane.

¹H NMR (400 MHz, MeOH-d₄) δ ppm; 0.91 (3H, d, J=6.8 Hz), 0.96 (3H, t, J=7.6 Hz), 1.17-1.28 (1H, m), 1.38-1.50(1H, m), 1.93-2.04 (1H, m), 3.79 (1H, dd, J=8.4, 12.8 Hz), 3.99 (1H, dd, J=6.8, 12.8 Hz), 6.53 (1H, dd, J=1.6, 3.6 Hz), 6.58 (1H, d, J=9.2 Hz), 6.87 (1H, d, J=3.6 Hz), 7.39 (1H, dd, J=2.4, 9.2 Hz), 7.57 (1H, br), 7.60 (1H, d, J=2.4 Hz), 8.12 (1H, s).

Example 77

5-[2-Amino-4-(2-furyl)-5-pyrimidinyl]-1-octyl-1,2-dihydro-2-pyridinone

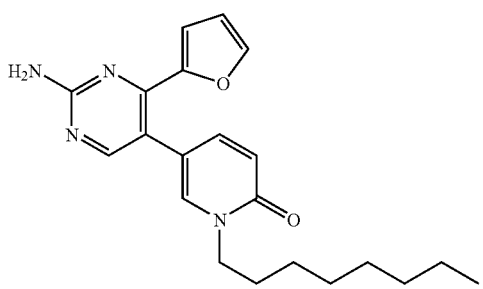

The title compound was synthesized in a similar manner to Example 66 using octyl bromide.

¹H NMR (400 MHz, CDCl₃) δ ppm; 0.87 (3H, t, J=7.2 Hz), 1.18-1.42 (10H, m), 1.72-1.81 (2H, m), 3.95 (2H, d, J=7.6 Hz), 5.17 (2H, br s), 6.43 (1H, dd, J=1.6, 3.6 Hz), 6.60 (1H, d, J=10.4 Hz), 6.66 (1H, dd, J=0.8, 3.6 Hz), 7.16-7.22 (2H, m), 7.48-7.51 (1H, m), 8.13 (1H, s).

Example 78

2-{5-[2-Amino-4-(2-furyl)-5-pyrimidinyl]-2-oxo-1,2-dihydro-1-pyridinyl}ethylcyanide

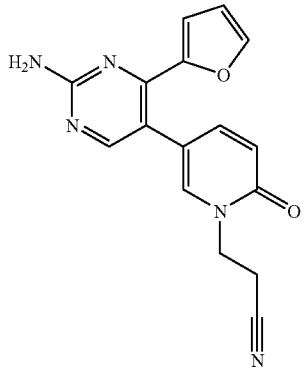

The title compound was synthesized in a similar manner to Example 66 using 3-bromopropionitrile.

¹H NMR (400 MHz, CDCl₃) δ ppm; 2.99 (2H, t, J=6.0 Hz), 4.20 (2H, t, J=6.0 Hz), 5.18 (2H, br s), 6.45 (1H, dd, J=1.6, 3.6 Hz), 6.62 (1H, d, J=9.6 Hz), 6.78 (1H, d, J=3.6 Hz), 7.22-7.33 (2H, m), 7.48-7.51 (1H, m), 8.16 (1H, s).

Example 79

5-[2-Amino-4-(2-furyl)-5-pyrimidinyl]-1-(3-fluoropropyl)-1,2-dihydro-2-pyridinone

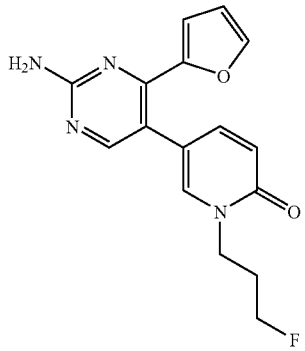

The title compound was synthesized in a similar manner to Example 66 using 1-bromo-3-fluoropropane.

¹H NMR (400 MHz, CDCl₃) δ ppm; 2.21 (2H, dtt, J=6.0, 6.8, 27.2 Hz), 4.12 (2H, t, J=6.8 Hz), 4.51 (2H, dt, J=6.0, 46.8 Hz), 5.42 (2H, br s), 6.46 (1H, dd, J=1.6, 3.6 Hz), 6.60 (1H, dd, J=0.8, 9.2 Hz), 6.75 (1H, d, J=3.6 Hz), 7.20-7.26 (2H, m), 7.48-7.52 (1H, m), 8.11 (1H, s).

Example 80

5-[2-Amino-4-(2-furyl)-5-pyrimidinyl]-1-(2-hydroxyethyl)-1,2-dihydro-2-pyridinone

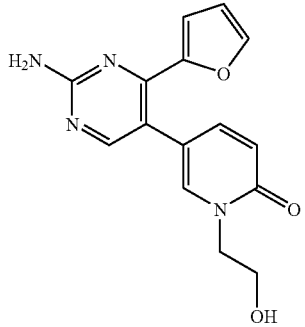

The title compound was synthesized in a similar manner to Example 66 using 2-iodoethanol.
MS m/e (ESI) 299 (MH+).

Example 81

5-[2-Amino-4-(2-furyl)-5-pyrimidinyl]-1-(3-hydroxypropyl)-1,2-dihydro-2-pyridinone

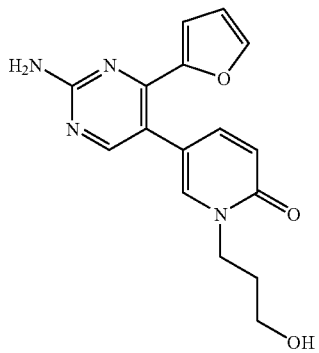

The title compound was synthesized in a similar manner to Example 66 using 3-iodopropanol.
¹H NMR (400 MHz, MeOH-d₄) δ ppm; 1.98 (2H, dt, J=6.4, 6.4 Hz), 3.60 (2H, t, J=6.4 Hz), 4.14 (2H, t, J=6.4 Hz), 6.54 (1H, dd, J=2.0, 3.6 Hz), 6.58 (1H, d, J=9.2 Hz), 6.89 (1H, d, J=3.6 Hz), 7.39 (1H, dd, J=2.4, 9.2 Hz), 7.58-7.60 (1H, m), 7.66 (1H, d, J=2.4 Hz), 8.15 (1H, s).

Example 82

5-[2-Amino-4-(2-furyl)-5-pyrimidinyl]-1-(2-methoxyethyl)-1,2-dihydro-2-pyridinone

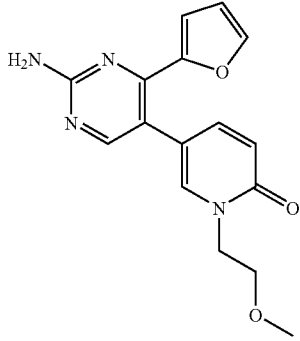

The title compound was synthesized in a similar manner to Example 66 using 2-bromoethyl methyl ether.
¹H NMR (400 MHz, CDCl₃) δ ppm; 3.30 (3H, s), 3.70 (2H, t, J=4.8 Hz), 4.16 (2H, t, J=4.8 Hz), 5.23 (2H, br s), 6.40-6.46 (1H, m), 6.60 (1H, d, J=9.2 Hz), 6.65 (1H, d, J=3.2 Hz), 7.20 (1H, dd, J=2.4, 9.2 Hz), 7.31 (1H, d, J=1.6 Hz), 7.50 (1H, br), 8.14 (1H, s).

Example 83

5-[2-Amino-4-(2-furyl)-5-pyrimidinyl]-1-[2-(1H-1-pyrrolyl)ethyl]-1,2-dihydro-2-pyridinone

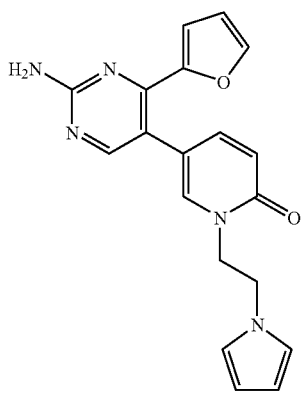

The title compound was synthesized in a similar manner to Example 66 using 1-(2-bromoethyl)pyrrole.
¹H NMR (400 MHz, CDCl₃) δ ppm; 4.21-4.26 (2H, m), 4.28-4.33 (2H, m), 5.12 (2H, br s), 6.12 (2H, dd, J=2.0, 2.0 Hz), 6.37 (1H, d, J=2.4 Hz), 6.43 (1H, dd, J=1.6, 3.6 Hz), 6.52 (2H, dd, J=2.0, 2.0 Hz), 6.57 (1H, d, J=9.6 Hz), 6.66 (1H, dd, J=0.8, 3.6 Hz), 7.15 (1H, dd, J=2.4, 9.6 Hz), 7.47 (1H, dd, J=0.8, 1.6 Hz), 7.84 (1H, s).

Example 84

2-{5-[2-Amino-4-(2-furyl)-5-pyrimidinyl]-2-oxo-1,2-dihydro-1-pyridinyl}acetamide

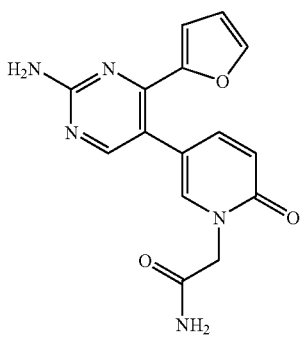

The title compound was synthesized in a similar manner to Example 66 using 2-bromoacetamide.

$^1$H NMR (400 MHz, DMSO-d$_6$) δ ppm; 4.52 (2H, s), 6.38 (1H, d, J=9.2 Hz), 6.56 (1H, dd, J=1.6, 3.6 Hz), 6.73 (1H, d, J=3.6 Hz), 6.80 (2H, br s), 7.19 (1H, br s), 7.24 (1H, dd, J=2.4, 9.2 Hz), 7.62 (1H, br s), 7.63 (1H, d, J=2.4 Hz), 7.77 (1H, br), 8.10 (1H, s).

Example 85

5-[2-Amino-4-(2-furyl)-5-pyrimidinyl]-1-(cyclopropylmethyl)-1,2-dihydro-2-pyridinone

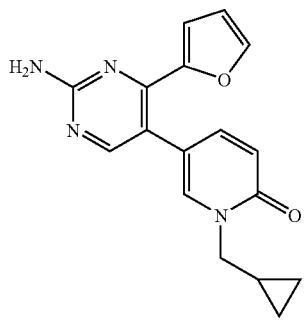

The title compound was synthesized in a similar manner to Example 66 using cyclopropylmethyl bromide.

$^1$H NMR (400 MHz, CDCl$_3$) δ ppm; 0.36-0.41 (2H, m), 0.58-0.65 (2H, m), 1.22-1.33 (1H, m), 3.84 (2H, d, J=7.2 Hz), 5.16 (2H, br s), 6.44 (1H, dd, J=1.6, 3.6 Hz), 6.62 (1H, d, J=9.2 Hz), 6.68 (1H, d, J=3.6 Hz), 7.21 (1H, dd, J=2.4, 9.2 Hz), 7.32 (1H, d, J=2.4 Hz), 7.48-7.52 (1H, m), 8.15 (1H, s).

Example 86

5-[2-Amino-4-(2-furyl)-5-pyrimidinyl]-1-[2-(2-methoxyethoxy)ethyl]-1,2-dihydro-2-pyridinone

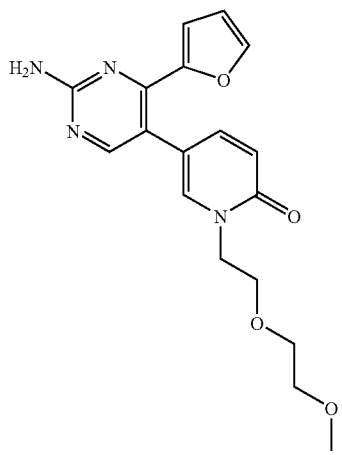

The title compound was synthesized in a similar manner to Example 66 using 1-bromo-2-(2-methoxyethoxy)ethane.

$^1$H NMR (400 MHz, CDCl$_3$) δ ppm; 3.27 (3H, s), 3.39-3.46 (2H, m), 3.53-3.61 (2H, m), 3.81 (2H, t, J=4.8 Hz), 4.19 (2H, t, J=4.8 Hz), 5.50 (2H, br s), 6.43 (1H, dd, J=1.6, 3.2 Hz), 6.59 (1H, d, J=9.2 Hz), 6.66 (1H, d, J=3.2 Hz), 7.19 (1H, dd, J=2.4, 9.2 Hz), 7.41 (1H, d, J=2.4 Hz), 7.50 (1H, d, J=1.6 Hz), 8.15 (1H, s).

Example 87

5-[2-Amino-4,6-di(2-furyl)-5-pyrimidinyl]-1-ethyl-1,2-dihydro-2-pyridinone

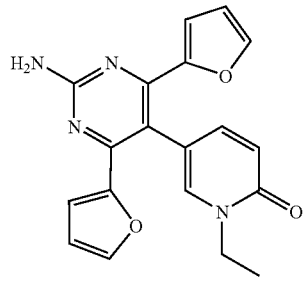

The title compound was synthesized in a similar manner to Example 66 using 5-[2-amino-4,6-di(2-furyl)-5-pyrimidinyl]-1,2-dihydro-2-pyridinone and ethyl iodide.

$^1$H NMR (400 MHz, DMSO-d$_6$) δ ppm; 1.15 (3H, t, J=7.2 Hz), 3.89 (2H, q, J=7.2 Hz), 6.37 (2H, dd, J=0.8, 3.6 Hz), 6.48 (1H, dd, J=0.4, 9.2 Hz), 6.53 (2H, dd, J=1.6, 3.6 Hz), 6.87 (2H, br s), 7.27 (1H, dd, J=2.4, 9.2 Hz), 7.61 (1H, d, J=2.4 Hz), 7.75 (2H, dd, J=0.8, 1.6 Hz).

Example 88

5-[2-Amino-4,6-di(2-furyl)-5-pyrimidinyl]-1-allyl-1,2-dihydro-2-pyridinone

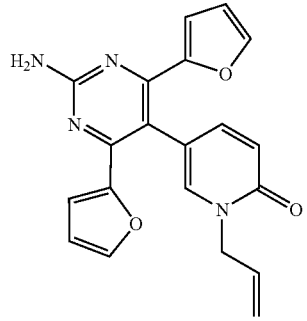

The title compound was synthesized in a similar manner to Example 66 using 5-[2-amino-4,6-di(2-furyl)-5-pyrimidinyl]-1,2-dihydro-2-pyridinone and allyl bromide.

$^1$H NMR (400 MHz, DMSO-d$_6$) δ ppm; 4.50 (2H, d, J=5.2 Hz), 4.95 (1H, dd, J=1.2, 17.2 Hz), 5.08 (1H, dd, J=1.2, 10.0 Hz), 5.88 (1H, ddt, J=5.2, 10.0, 17.2 Hz), 6.43 (2H, dd, J=0.8, 3.6 Hz), 6.52 (1H, dd, J=0.8, 9.2 Hz), 6.53 (2H, dd, J=1.6, 3.6 Hz), 6.86 (2H, br s), 7.32 (1H, dd, J=2.4, 9.2 Hz), 7.50 (1H, dd, J=0.8, 2.4 Hz), 7.74 (2H, dd, J=0.8, 1.6 Hz).

Example 89

5-[2-Amino-4,6-di(2-furyl)-5-pyrimidinyl]-1-propyl-1,2-dihydro-2-pyridinone

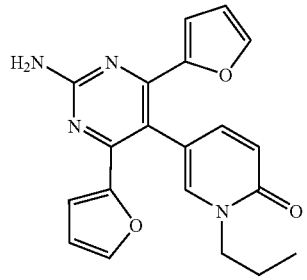

The title compound was synthesized in a similar manner to Example 66 using 5-[2-amino-4,6-di(2-furyl)-5-pyrimidinyl]-1,2-dihydro-2-pyridinone and propyl iodide.

¹H NMR (400 MHz, CDCl₃) δ ppm; 0.90 (3H, t, J=7.2 Hz), 1.76 (2H, tq, J=7.2, 7.2 Hz), 3.93 (2H, t, J=7.2 Hz), 6.12 (2H, br s), 6.44 (2H, dd, J=1.6, 3.6 Hz), 6.57 (2H, d, J=3.6 Hz), 6.78 (1H, d, J=9.2 Hz), 7.11 (1H, d, J=2.4 Hz), 7.24 (1H, dd, J=2.4, 9.2 Hz), 7.53 (2H, dd, J=0.8, 1.6 Hz).

Example 90

5-[2-Amino-4,6-di(2-furyl)-5-pyrimidinyl]-1-butyl-1,2-dihydro-2-pyridinone

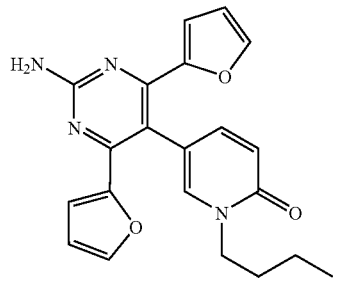

The title compound was synthesized in a similar manner to Example 66 using 5-[2-amino-4,6-di(2-furyl)-5-pyrimidinyl]-1,2-dihydro-2-pyridinone and butyl iodide.

¹H NMR (400 MHz, CDCl₃) δ ppm; 0.90 (3H, t, J=7.2 Hz), 1.23-1.34 (2H, m), 1.65-1.74 (2H, m), 3.98 (2H, t, J=-7.2 Hz), 6.50 (2H, dd, J=1.6, 3.6 Hz), 6.75 (2H, d, J=3.6 Hz), 6.81 (1H, d, J=9.2 Hz), 7.04 (2H, br s), 7.14 (1H, d, J=2.4 Hz), 7.22-7.30 (1H, m), 7.56 (2H, d, J=1.6 HZ).

Example 91

5-[2-Amino-4,6-di(2-furyl)-5-pyrimidinyl]-1-(2-butynyl)-1,2-dihydro-2-pyridinone

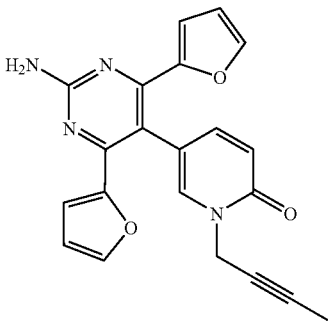

The title compound was synthesized in a similar manner to Example 66 using 5-[2-amino-4,6-di(2-furyl)-5-pyrimidinyl]-1,2-dihydro-2-pyridinone and 1-bromo-2-butyne.

¹H NMR (400 MHz, DMSO-d₆) δ ppm; 1.74 (3H, t, J=2.4 Hz), 4.65 (2H, q, J=2.4 Hz), 6.41 (2H, dd, J=0.8, 3.6 Hz), 6.52 (1H, dd, J=0.4, 9.2 Hz), 6.54 (2H, dd, J=2.0, 3.6 Hz), 6.88 (2H, br s), 7.30 (1H, dd, J=2.4, 9.2 Hz), 7.62 (1H, dd, J=0.4, 2.4 Hz), 7.75 (2H, dd, J=0.8, 2.0 Hz).

Example 92

5-[2-Amino-4,6-di(2-furyl)-5-pyrimidinyl]-1-(2-fluoroethyl)-1,2-dihydro-2-pyridinone

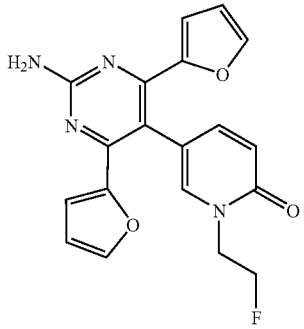

The title compound was synthesized in a similar manner to Example 66 using 5-[2-amino-4,6-di(2-furyl)-5-pyrimidinyl]-1,2-dihydro-2-pyridinone and 1-iodo-2-fluoroethane.

¹H NMR (400 MHz, DMSO-d₆) δ ppm; 4.22 (2H, dt, J=4.8, 26.0 Hz), 4.64 (2H, dt, J=4.8, 47.6 Hz), 6.38 (2H, dd, J=0.8, 3.6 Hz), 6.52 (2H, dd, J=1.6, 3.6 Hz), 6.52 (1H, d, J=9.2 Hz), 6.87 (2H, br s), 7.30 (1H, dd, J=2.8, 9.2 Hz), 7.59 (1H, d, J=2.8 Hz), 7.74 (2H, dd, J=0.8, 1.6 Hz).

Example 93

5-[2-Amino-4-(2-furyl)-5-pyrimidinyl]-1-(3-thienyl)-1,2-dihydro-2-pyridinone

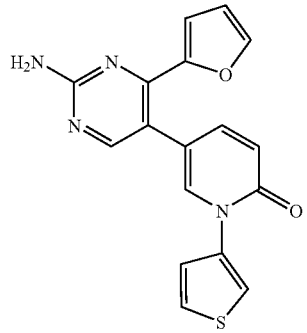

In a reaction vessel, 5-[2-amino-4-(2-furyl)-5-pyrimidinyl]-1,2-dihydro-2-pyridinone (50 mg, 0.197 mmol), thiophene-3-boronic acid (50 mg, 0.393 mmol), and copper acetate (4 mg, 0.0197 mmol) were suspended in N,N-dimethylformamide (3 ml). Pyridine (31 mg, 0.393 mmol) was added thereto, followed by stirring at room temperature for 14.5 hours in the air. After the reaction was terminated, the mixture was concentrated and suspended in dimethylsulfoxide. Subsequently, the insoluble matters were removed by filtration and the resulting filtrate was purified by HPLC, to give the title compound (34 mg, 51%) as a pale yellow solid.

¹H NMR (400 MHz, DMSO-d₆) δ ppm; 6.47 (1H, dd, J=0.8, 9.6 Hz), 6.59 (1H, dd, J=1.6, 3.2 Hz), 6.78 (2H, br s), 6.82 (1H, dd, J=0.8, 3.2 Hz), 7.28 (1H, dd, J=2.4, 9.6 Hz), 7.35 (1H, dd, J=1.6, 5.2 Hz), 7.61 (1H, dd, J=3.2, 5.2 Hz), 7.71 (1H, dd, J=0.8, 2.4 Hz), 7.78-7.81 (2H, m), 8.23 (1H, s).

Example 94

5-[2-Amino-4-(2-furyl)-5-pyrimidinyl]-1-phenyl-1,2-dihydro-2-pyridinone

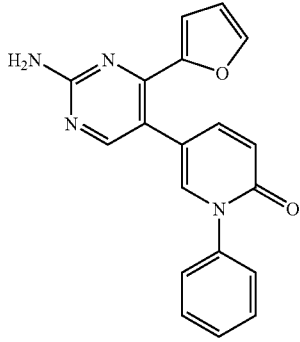

The title compound was synthesized in a similar manner to Example 93 using phenylboronic acid.

$^1$H NMR (400 MHz, DMSO-d$_6$) δ ppm; 6.47 (1H, dd, J=0.8, 9.2 Hz), 6.60 (1H, dd, J=1.6, 3.6 Hz), 6.77 (2H, br s), 6.82 (1H, dd, J=0.8, 3.6 Hz), 7.32 (1H, dd, J=2.4, 9.2 Hz), 7.40-7.52 (5H, m), 7.62 (1H, d, J=2.4 Hz), 7.81 (1H, dd, J=0.8, 1.6 Hz), 8.21 (1H, s).

Example 95

5-[2-Amino-4-(2-furyl)-5-pyrimidinyl]-1-[(E)-2-phenyl-1-ethenyl]-1,2-dihydro-2-pyridinone

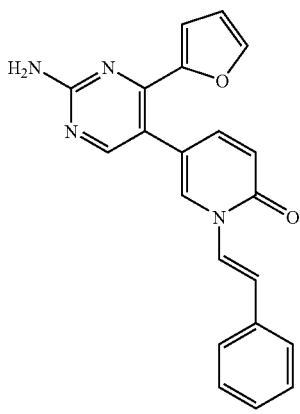

The title compound was synthesized in a similar manner to Example 93 using E-phenylethenylboronic acid.

$^1$H NMR (400 MHz, DMSO-d$_6$) δ ppm; 6.48 (1H, d, J=9.2 Hz), 6.59 (1H, dd, J=1.6, 3.2 Hz)., 6.79-6.84 (3H, m), 7.15 (1H, d, J=15.2 Hz), 7.27 (1H, dd, J=2.4, 9.6 Hz), 7.29 (1H, d, J=7.6 Hz), 7.37 (2H, t, J=7.6 Hz), 7.51 (2H, d, J=7.6 Hz), 7.78 (1H, dd, J=0.8, 1.6 Hz), 7.93 (1H, d, J=15.2 Hz), 8.06 (1H, d, J=2.4 Hz), 8.25 (1H, s).

Example 96

1-{4-[2-Amino-4,6-di(2-furyl)-5-pyrimidinyl]-2-pyridyl}-4-piperidinecarboxylic acid

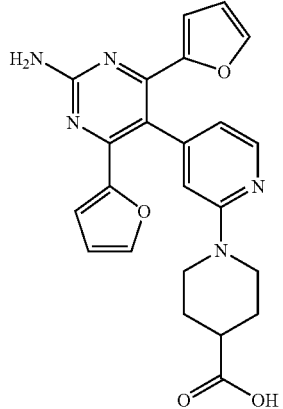

In a reaction vessel, ethyl1-{4-[2-amino-4,6-di(2-furyl)-5-pyrimidinyl]-2-pyridyl}-4-piperidinecarboxylate (59 mg, 0.128 mmol) was suspended in methanol (0.8 ml). A 5N aqueous sodium hydroxide solution (0.2 ml) was added therto, followed by stirring at room temperature for 15 hours. After the reaction was terminated, the reaction mixture was extracted with ethyl acetate, washed with water and brine, dried over anhydrous sodium sulfate and then the filtrate was concentrated, to give the title compound (20 mg, 36%) as a white solid.

$^1$H NMR (400 MHz, MeOH-d$_4$) δ ppm; 1.60-1.73 (2H, m), 1.88-1.96 (2H, m), 2.50-2.60 (1H, m), 2.96-3.05 (2H, m), 4.17-4.25 (2H, m), 6.25 (2H, dd, J=0.8, 3.6 Hz), 6.40 (2H, dd, J=2.0, 3.6 Hz), 6.58 (1H, dd, J=1.2, 5.2 Hz), 6.78 (1H, br), 7.55 (2H, dd, J=0.8, 2.0 Hz), 8.20 (1H, dd, J=0.8, 5.2 Hz).

Example 97

4-{5-[2-Amino-4-(2-furyl)-5-pyrimidinyl]-2-oxo-1,2-dihydro-1-pyridinyl}butyric acid

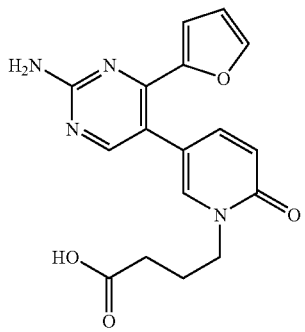

The title compound was synthesized in a similar manner to Example 96 using methyl 4-{5-[2-amino-4-(2-furyl)-5-pyrimidinyl]-2-oxo-1,2-dihydro-1-pyridinyl}butanoate.

$^1$H NMR (400 MHz, DMSO-d$_6$) δ ppm; 1.89 (2H, tt, J=7.2, 7.2 Hz), 2.21 (2H, t, J=7.2 Hz), 3.91 (2H, t, J=7.2 Hz), 6.37 (1H, d, J=9.2 Hz), 6.56 (1H, dd, J=1.6, 3.6 Hz), 6.70 (1H, d, J=3.6 Hz), 6.79 (2H, br s), 7.22 (1H, dd, J=2.4, 9.2 Hz), 7.65 (1H, d, J=2.4 Hz), 7.74-7.76 (1H, m), 8.15 (1H, s).

Example 98

5-(2-Fluoro-4-pyridyl)-4-(2-furyl)-2-pyrimidinylamine

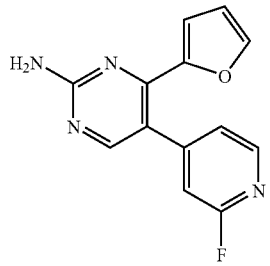

The title compound was synthesized in a similar manner to Reference Example 6 and Example 14 using 2-(fluoro-4-pyridyl)-1-(2-furyl)-1-ethanone.

$^1$H NMR (400 MHz, DMSO-d$_6$) δ ppm; 6.59 (1H, dd, J=1.8, 3.6 Hz), 6.81 (1H, dd, J=0.8, 3.6 Hz), 7.06 (2H, br s, 2H), 7.13 (1H, s), 7.18-7.22 (1H, m), 7.70 (1H, dd, J=0.8, 1.8 Hz), 8.21 (1H, d, J=5.2 Hz), 8.27 (1H, s).

Example 99

4-[2-Amino-4-(2-furyl)-5-pyrimidinyl]-1,2-dihydro-2-pyridinone

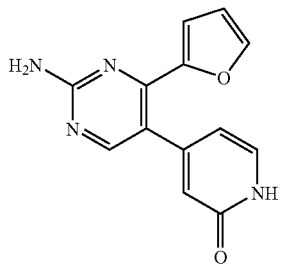

A suspension of 5-(2-fluoro-4-pyridyl)-4-(2-furyl)-2-pyrimidinylamine (3.00 g, 11.70 mmol) in concentrated hydrochloric acid (15 ml)-water (15 ml) was stirred at 100° C. for 2 hours. After cooling as it was, the reaction mixture was neutralized with a 5N aqueous sodium hydroxide solution. The resulting solid was collected by filtration, washed with water and dried at 60° C. for 22 hours, to give the title compound (2.19 g, 70%) as a pale brown solid.

$^1$H NMR (400 MHz, DMSO-d$_6$) δ ppm; 5.93 (1H, dd, J=1.8, 6.8 Hz), 6.26 (1H, d, J=1.8 Hz), 6.59 (1H, dd, J=1.8, 3.4 Hz), 6.82 (1H, dd, J=0.8, 3.4 Hz), 6.96 (2H, br s), 7.31 (1H, d, J=6.8 Hz), 7.78 (1H, dd, J=0.8, 1.8 Hz), 8.19 (1H, s).

The compounds of Examples 100 to 142 below were synthesized in a similar manner to Examples 16, 66, and/or 96 using 4-[2-amino-4-(2-furyl)-5-pyrimidinyl]-1,2-dihydro-2-pyridinone.

Example 100

4-[2-Amino-4-(2-furyl)-5-pyrimidinyl]-1-benzyl-1,2-dihydro-2-pyridinone

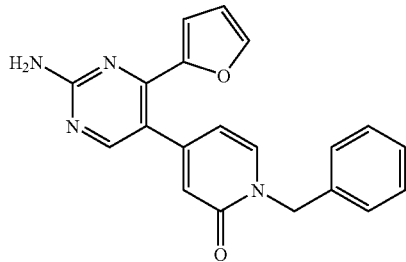

MS m/e (ESI) 345 (MH$^+$).

Example 101

4-[2-Amino-4-(2-furyl)-5-pyrimidinyl]-1-phenethyl-1,2-dihydro-2-pyridinone

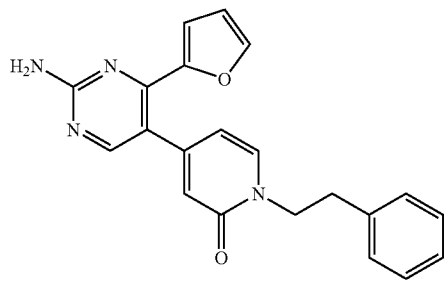

MS m/e (ESI) 359 (MH$^+$).

Example 102

4-[2-Amino-4-(2-furyl)-5-pyrimidinyl]-1-(3-phenylpropyl)-1,2-dihydro-2-pyridinone

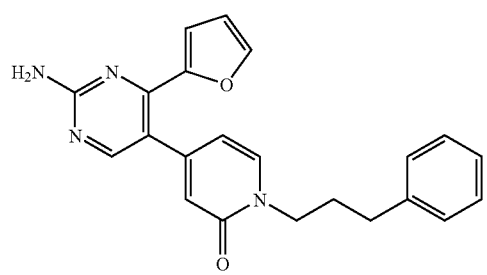

MS m/e (ESI) 373 (MH$^+$).

Example 103

4-[2-Amino-4-(2-furyl)-5-pyrimidinyl]-1-(2-fluorobenzyl)-1,2-dihydro-2-pyridinone

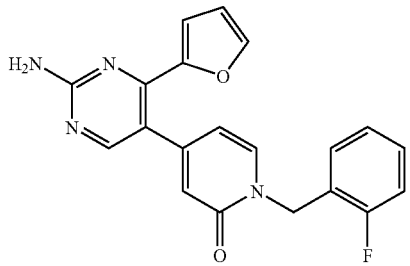

MS m/e (ESI) 363 (MH$^+$).

Example 104

4-[2-Amino-4-(2-furyl)-5-pyrimidinyl]-1-(3-fluorobenzyl)-1,2-dihydro-2-pyridinone

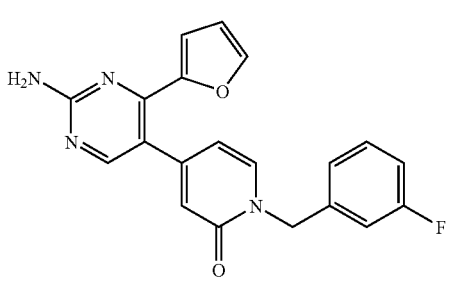

MS m/e (ESI) 363 (MH$^+$).

Example 105

4-[2-Amino-4-(2-furyl)-5-pyrimidinyl]-1-(4-fluorobenzyl)-1,2-dihydro-2-pyridinone

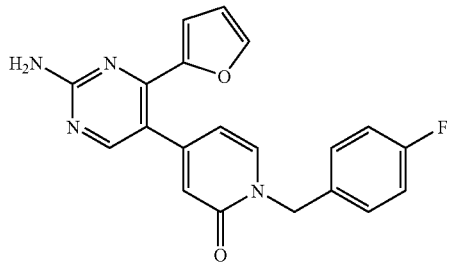

MS m/e (ESI) 363 (MH+).

Example 106

4-[2-Amino-4-(2-furyl)-5-pyrimidinyl]-1-(2,4-difluorobenzyl)-1,2-dihydro-2-pyridinone

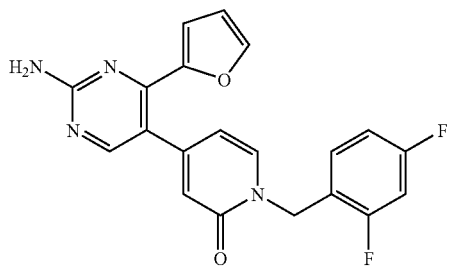

MS m/e (ESI) 381 (MH+).

Example 107

4-[2-Amino-4-(2-furyl)-5-pyrimidinyl]-1-(2,5-difluorobenzyl)-1,2-dihydro-2-pyridinone

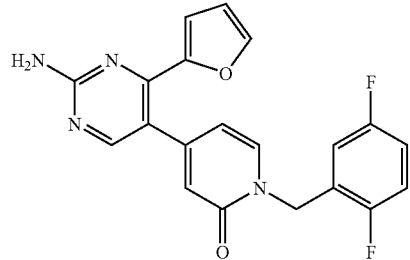

MS m/e (ESI) 381 (MH+).

Example 108

4-[2-Amino-4-(2-furyl)-5-pyrimidinyl]-1-(3-trifluoromethylbenzyl)-1,2-dihydro-2-pyridinone

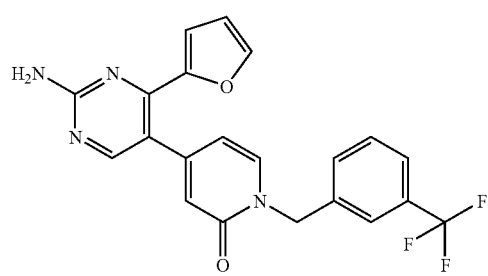

MS m/e (ESI) 413 (MH+).

Example 109

4-[2-Amino-4-(2-furyl)-5-pyrimidinyl]-1-(4-trifluoromethylbenzyl)-1,2-dihydro-2-pyridinone

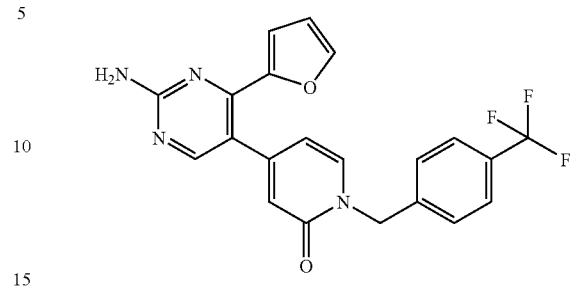

MS m/e (ESI) 413 (MH+).

Example 110

4-[2-Amino-4-(2-furyl)-5-pyrimidinyl]-1-methyl-1,2-dihydro-2-pyridinone

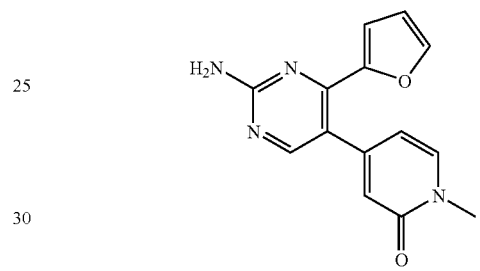

MS m/e (ESI) 269 (MH+).

Example 111

4-[2-Amino-4-(2-furyl)-5-pyrimidinyl]-1-ethyl-1,2-dihydro-2-pyridinone

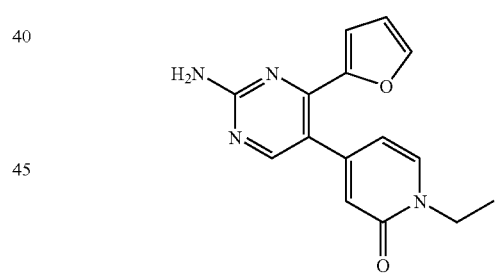

MS m/e (ESI) 283 (MH+).

Example 112

4-[2-Amino-4-(2-furyl)-5-pyrimidinyl]-1-propyl-1,2-dihydro-2-pyridinone

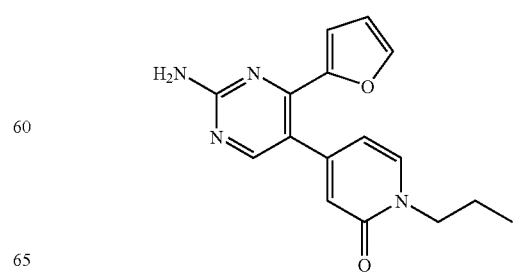

MS m/e (ESI) 297 (MH+).

Example 113

1-Allyl-4-[2-amino-4-(2-furyl)-5-pyrimidinyl]-1,2-dihydro-2-pyridinone

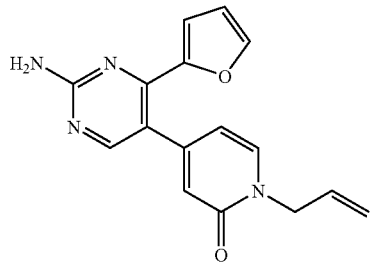

MS m/e (ESI) 295 (MH⁺).

Example 114

4-[2-Amino-4-(2-furyl)-5-pyrimidinyl]-1-(3-butenyl)-1,2-dihydro-2-pyridinone

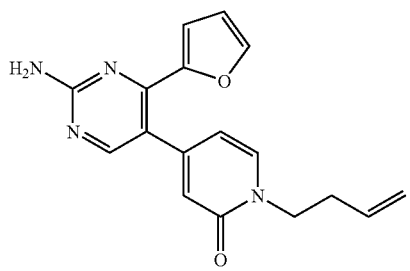

MS m/e (ESI) 309 (MH⁺).

Example 115

7-{4-[2-Amino-4-(2-furyl)-5-pyrimidinyl]-2-oxo-1,2-dihydro-1-pyridinyl}heptanenitrile

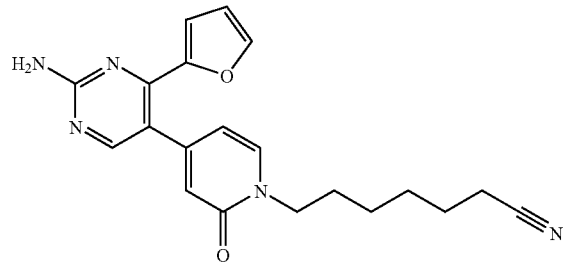

MS m/e (ESI) 364 (MH⁺).

Example 116

4-[2-Amino-4-(2-furyl)-5-pyrimidinyl]-1-cyclobutylmethyl-1,2-dihydro-2-pyridinone

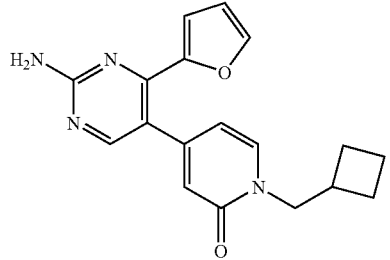

MS m/e (ESI) 323 (MH⁺).

Example 117

4-[2-Amino-4-(2-furyl)-5-pyrimidinyl]-1-(3-fluoropropyl)-1,2-dihydro-2-pyridinone

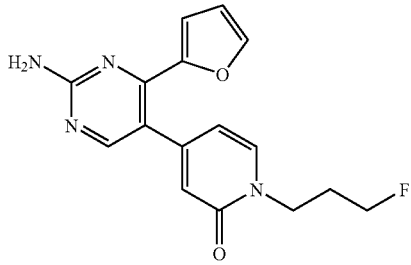

MS m/e (ESI) 315 (MH⁺).

Example 118

4-{4-[2-Amino-4-(2-furyl)-5-pyrimidinyl]-2-oxo-1,2-dihydro-1-pyridinyl}butyronitrile

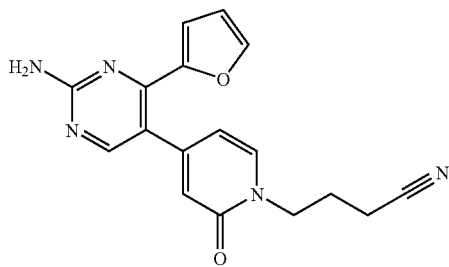

MS m/e (ESI) 322 (MH⁺).

Example 119

4-[2-Amino-4-(2-furyl)-5-pyrimidinyl]-1-(6-chloro-3-pyridylmethyl)-1,2-dihydro-2-pyridinone

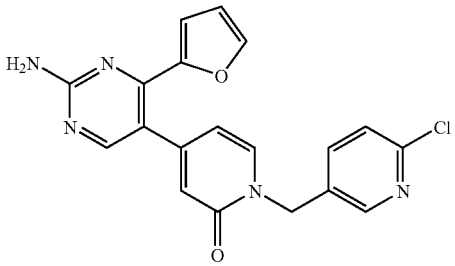

MS m/e (ESI) 380 (MH⁺).

Example 120

4-[2-Amino-4-(2-furyl)-5-pyrimidinyl]-1-(2-pyridylmethyl)-1,2-dihydro-2-pyridinone

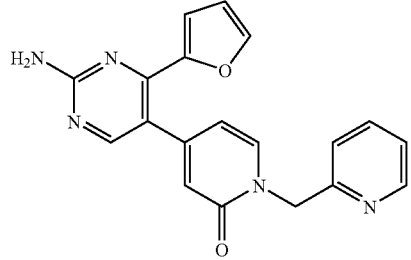

MS m/e (ESI) 346 (MH⁺).

Example 121

4-[2-Amino-4-(2-furyl)-5-pyrimidinyl]-1-(3-pyridyl-methyl)-1,2-dihydro-2-pyridinone

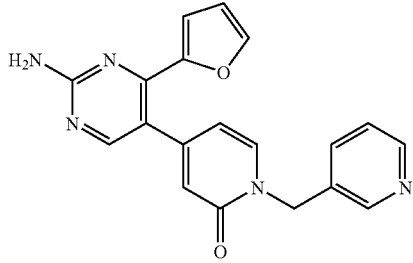

MS m/e (ESI) 346 (MH$^+$).

Example 122

4-[2-Amino-4-(2-furyl)-5-pyrimidinyl]-1-(4-pyridyl-methyl)-1,2-dihydro-2-pyridinone

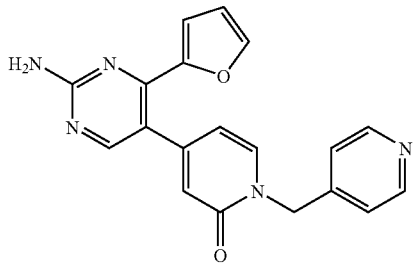

MS m/e (ESI) 346 (MH$^+$).

Example 123

4-[2-Amino-4-(2-furyl)-5-pyrimidinyl]-1-(2-buty-nyl)-1,2-dihydro-2-pyridinone

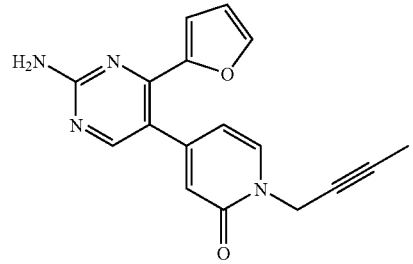

MS m/e (ESI) 307 (MH$^+$).

Example 124

4-[2-Amino-4-(2-furyl)-5-pyrimidinyl]-1-(4,4,4-trifluorobutyl)-1,2-dihydro-2-pyridinone

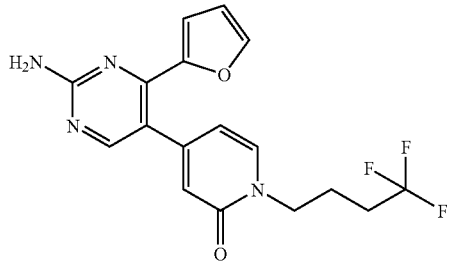

MS m/e (ESI) 365 (MH$^+$).

Example 125

4-[2-Amino-4-(2-furyl)-5-pyrimidinyl]-1-(2-methoxyethyl)-1,2-dihydro-2-pyridinone

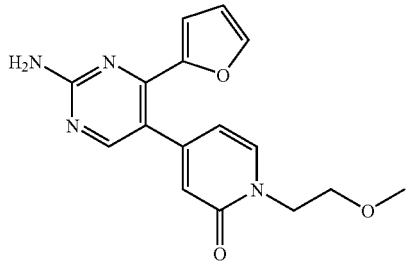

MS m/e (ESI) 313 (MH$^+$).

Example 126

4-[2-Amino-4-(2-furyl)-5-pyrimidinyl]-1-(2-penty-nyl-1,2-dihydro-2-pyridinone

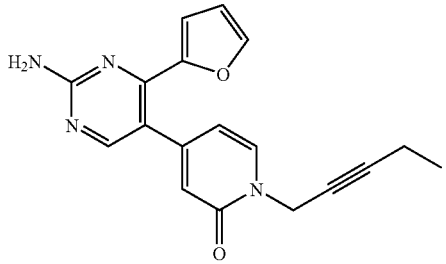

MS m/e (ESI) 321 (MH$^+$).

Example 127

4-[2-Amino-4-(2-furyl)-5-pyrimidinyl]-1-(2-methylallyl)-1,2-dihydro-2-pyridinone

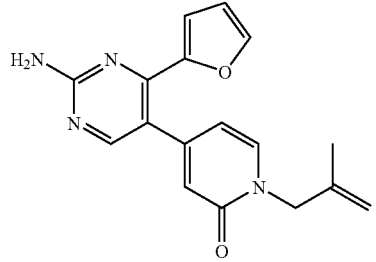

MS m/e (ESI) 309 (MH$^+$).

Example 128

4-[2-Amino-4-(2-furyl)-5-pyrimidinyl]-1-isobutyl-1,2-dihydro-2-pyridinone

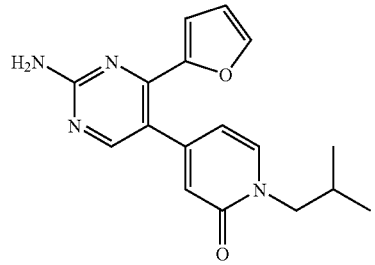

MS m/e (ESI) 311 (MH$^+$).

Example 129

4-[2-Amino-4-(2-furyl)-5-pyrimidinyl]-1-(2-pentenyl)-1,2-dihydro-2-pyridinone

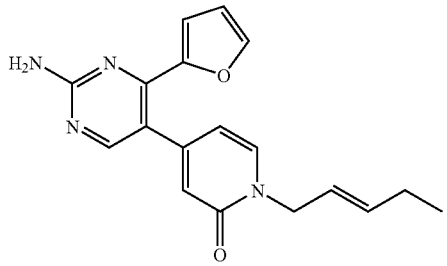

MS m/e (ESI) 323 (MH⁺).

Example 130

4-[2-Amino-4-(2-furyl)-5-pyrimidinyl]-1-(3-methyl-2-butenyl)-1,2-dihydro-2-pyridinone

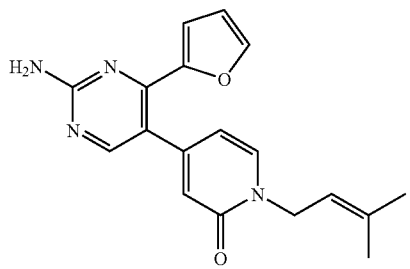

MS m/e (ESI) 323 (MH⁺).

Example 131

4-[2-Amino-4-(2-furyl)-5-pyrimidinyl]-1-(3-methylbutyl)-1,2-dihydro-2-pyridinone

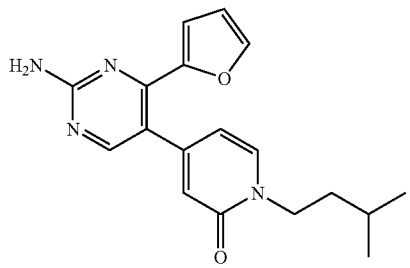

MS m/e (ESI) 325 (MH⁺).

Example 132

4-[2-Amino-4-(2-furyl)-5-pyrimidinyl]-1-(4-methyl-3-pentenyl)-1,2-dihydro-2-pyridinone

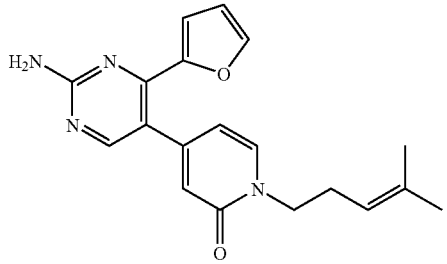

MS m/e (ESI) 337 (MH⁺).

Example 133

4-[2-Amino-4-(2-furyl)-5-pyrimidinyl]-1-(2-propynyl)-1,2-dihydro-2-pyridinone

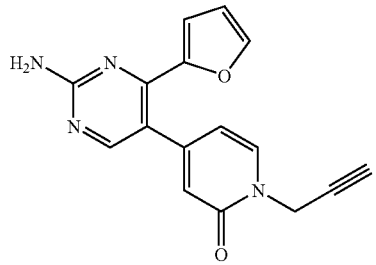

MS m/e (ESI) 293 (MH⁺).

Example 134

4-[2-Amino-4-(2-furyl)-5-pyrimidinyl]-1-(2-diethylaminoethyl)-1,2-dihydro-2-pyridinone

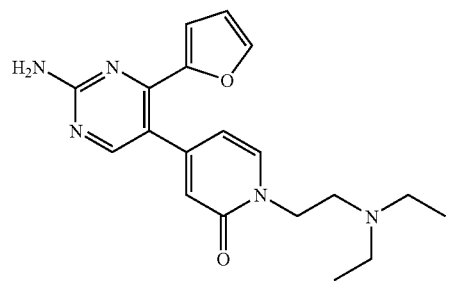

MS m/e (ESI) 354 (MH⁺).

Example 135

4-[2-Amino-4-(2-furyl)-5-pyrimidinyl]-1-(2,2,2-trifluoroethyl)-1,2-dihydro-2-pyridinone

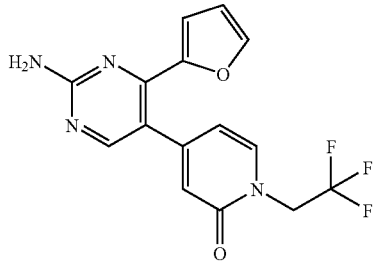

MS m/e (ESI) 337 (MH⁺).

Example 136

4-[2-Amino-4-(2-furyl)-5-pyrimidinyl]-1-(2-fluoroethyl)-1,2-dihydro-2-pyridinone

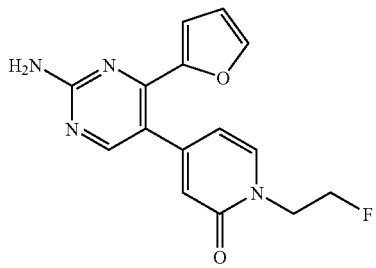

MS m/e (ESI) 301 (MH⁺).

Example 137

4-[2-Amino-4-(2-furyl)-5-pyrimidinyl]-1-(1,2,2,2-tetrafluoroethyl)-1,2-dihydro-2-pyridinone

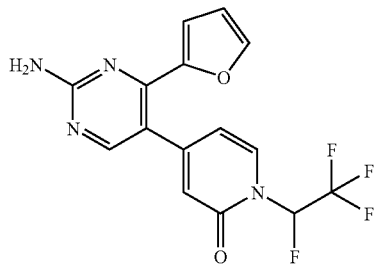

MS m/e (ESI) 355 (MH$^+$).

Example 138

4-[2-Amino-4-(2-furyl)-5-pyrimidinyl]-1-(2,2-difluoroethyl)-1,2-dihydro-2-pyridinone

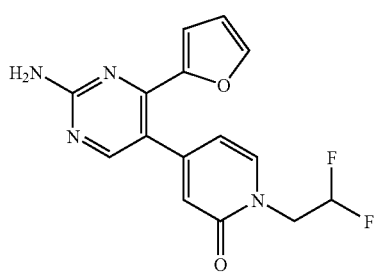

MS m/e (ESI) 319 (MH$^+$).

Example 139

4-[2-Amino-4-(2-furyl)-5-pyrimidinyl]-1-(2-ethoxyethyl)-1,2-dihydro-2-pyridinone

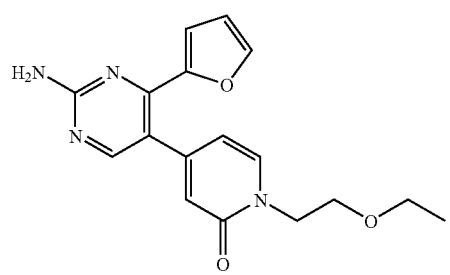

MS m/e (ESI) 327 (MH$^+$).

Example 140

Methyl {4-[2-amino-4-(2-furyl)-5-pyrimidinyl]-2-oxo-1,2-dihydro-1-pyridinyl}acetate

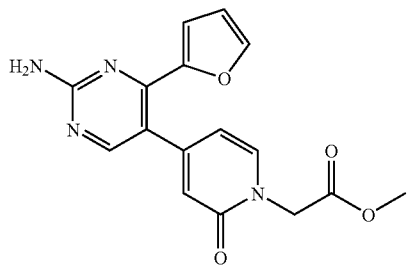

MS m/e (ESI) 327 (MH$^+$).

Example 141

{4-[2-Amino-4-(2-furyl)-5-pyrimidinyl]-2-oxo-1,2-dihydro-1-pyridinyl}acetic acid

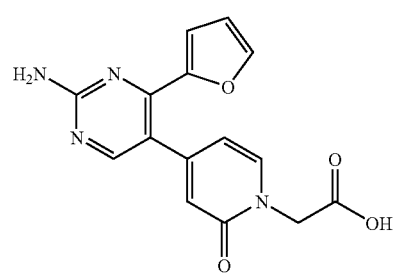

MS m/e (ESI) 313 (MH$^+$).

Example 142

4-{4-[2-Amino-4-(2-furyl)-5-pyrimidinyl]-2-oxo-1,2-dihydro-1-pyridinyl}butyric acid

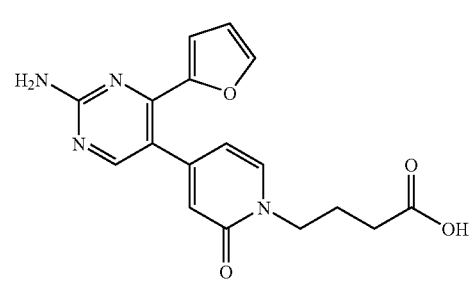

MS m/e (ESI) 341 (MH$^+$).

Example 143

N1,N1-Diethyl-2-{4-[2-amino-4-(2-furyl)-5-pyrimidinyl]-2-oxo-1,2-dihydro-1-pyridinyl}acetamide

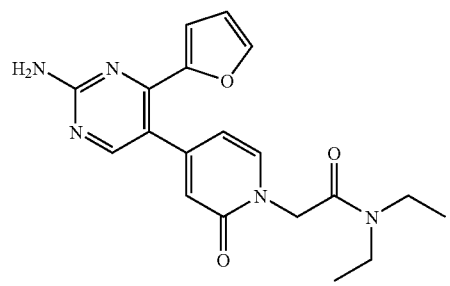

A suspension of {4-[2-amino-4-(2-furyl)-5-pyrimidinyl]-2-oxo-1,2-dihydro-1-pyridinyl}acetic acid (10 mg, 32 µmol), 1-hydroxybenzotriazole (15 mg, 98 µmol), 3-(3'-dimethylaminopropyl)-1-ethylcarbodiimide (15 mg, 96 µmol), diethylamine hydrochloride (18 mg, 164 µmol) and triethylamine (22 µl, 160 µmol) in N,N-dimethylformamide (1.0 ml) was stirred at room temperature for 17 hours. The reaction mixture was diluted with water and then extracted with ethyl acetate. The organic layer was concentrated and then purified by HPLC, to give the title compound (0.73 mg, 6%).

MS m/e (ESI) 368 (MH$^+$).

Example 144

N1-Phenyl-2-{4-[2-amino-4-(2-furyl)-5-pyrimidinyl]-2-oxo-1,2-dihydro-1-pyridinyl}acetamide

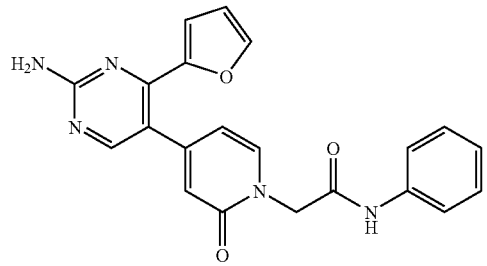

The title compound was synthesized in a similar manner to Example 143 using aniline.

MS m/e (ESI) 388 (MH+).

Example 145

4-[2-Amino-4,6-di(2-furyl)-5-pyrimidinyl]-1,2-dihydro-2-pyridinone

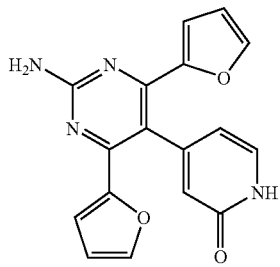

The title compound was synthesized in a similar manner to Example 99 using 5-(2-fluoro-4-pyridyl)-4,6-di(2-furyl)-2-pyrimidinylamine.

$^1$H NMR (400 MHz, DMSO-$d_6$) δ ppm; 6.13 (1H, dd, J=1.6, 6.8 Hz), 6.19 (1H, d, J=1.6 Hz), 6.51-6.56 (4H, m), 6.91 (2H, br s), 7.48 (1H, d, J=6.8 Hz), 7.74-7.78 (2H, m).

The compounds of Examples 146 to 148 below were synthesized in a similar manner to Examples 16 or 66 using 4-[2-amino-4,6-di(2-furyl)-5-pyrimidinyl]-1,2-dihydro-2-pyridinone.

Example 146

4-[2-Amino-4,6-di(2-furyl)-5-pyrimidinyl]-1-methyl-1,2-dihydro-2-pyridinone

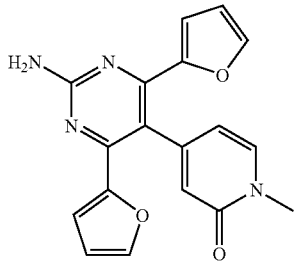

MS m/e (ESI) 335 (MH+).

Example 147

4-[2-Amino-4,6-di(2-furyl)-5-pyrimidinyl]-1-ethyl-1,2-dihydro-2-pyridinone

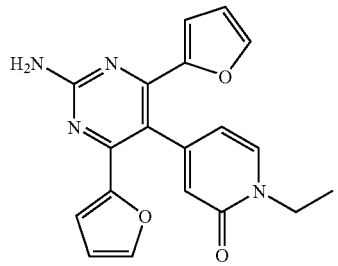

MS m/e (ESI) 349 (MH+).

Example 148

4-[2-Amino-4,6-di(2-furyl)-5-pyrimidinyl]-1-propyl-1,2-dihydro-2-pyridinone

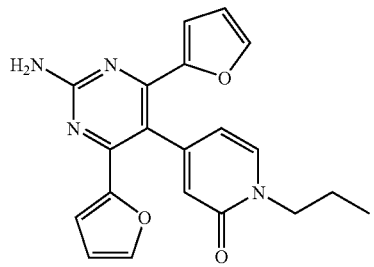

MS m/e (ESI) 363 (MH+).

Example 149

5-[2-Amino-4,6-di(2-furyl)-5-pyrimidinyl]-1-(3-hydroxypropyl)-1,2-dihydro-2-pyridinone

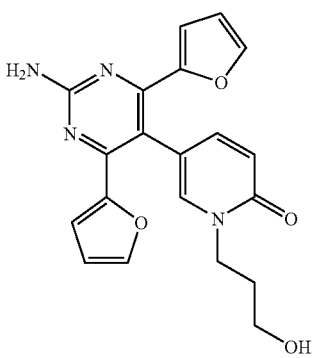

The title compound was synthesized in a similar manner to Example 66 using 5-[2-amino-4,6-di(2-furyl)-5-pyrimidinyl]-1,2-dihydro-2-pyridinone and 3-iodopropanol.

MS m/e (ESI) 379 (MH+).

Example 150

4-[2-Amino-4-(2-furyl)-5-pyrimidinyl]-2-pyridinecarboxyamide

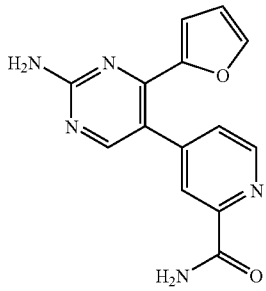

A suspension of 5-(2-fluoro-4-pyridyl)-4-(2-furyl)-2-pyrimidinylamine (300 mg, 1.17 mmol) and sodium cyanide in dimethylsulfoxide (3 ml) was stirred at 150° C. for 46 hours. After cooling as it was, the reaction mixture was diluted with ethyl acetate and washed with an aqueous solution of saturated ammonium chloride twice. The resulting organic layer was dried over anhydrous sodium sulfate and concentrated. The residue was subjected to silica gel plate (developing solvent; dichloromethane:methanol=10:1) and then washed with diethyl ether, to give the title compound (10 mg, 3%) as a colorless solid.

$^1$H NMR (400 MHz, DMSO-$d_6$) δ ppm; 6.40 (1H, dd, J=1.2, 5.2 Hz), 6.51 (1H, d, J=1.2 Hz), 6.54 (1H, dd, J=1.6, 3.4 Hz), 6.60 (1H, dd, J=0.8, 3.4 Hz), 6.89 (2H, br s), 7.72 (1H, dd, J=0.8, 1.6 Hz), 8.04 (1H, d, J=5.2 Hz), 8.18 (1H, s).

Example 151

5-(2-Methoxy-4-pyridyl)-4,6-di(2-furyl)-2-pyrimidinamine

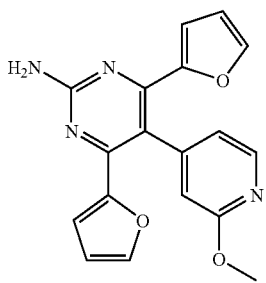

The title compound was synthesized in a similar manner to Example 64 using methanol.

$^1$H NMR (400 MHz, DMSO-$d_6$) δ ppm; 3.88 (3H, s), 6.08 (2H, d, J=3.6 Hz), 6.44 (2H, dd, J=1.6, 3.6 Hz), 6.73 (1H, br), 6.87-6.94 (3H, m), 7.65 (2H, d, J=1.6 Hz), 8.23 (1H, d, J=5.2 Hz).

Example 152

5-(2-Ethoxy-4-pyridyl)-4,6-di(2-furyl)-2-pyrimidinamine

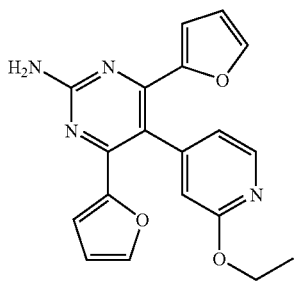

The title compound was synthesized in a similar manner to Example 64 using ethanol.

$^1$H NMR (400 MHz, DMSO-$d_6$) δ ppm; 1.32 (3H, t, J=7.2 Hz), 4.34 (2H, q, J=7.2 Hz), 6.09 (2H, dd, J=0.8, 3.6 Hz), 6.45 (2H, dd, J=1.6, 3.6 Hz), 6.70 (1H, dd, J=0.8, 1.2 Hz), 6.88-6.94 (3H, m), 7.67 (2H, dd, J=0.8, 1.6 Hz), 8.22 (1H, dd, J=0.8, 5.2 Hz).

Example 153

5-(2-Propoxy-4-pyridyl)-4,6-di(2-furyl)-2-pyrimidinamine

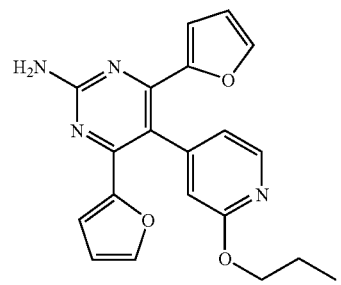

The title compound was synthesized in a similar manner to Example 64 using n-propanol.

$^1$H NMR (400 MHz, DMSO-$d_6$) δ ppm; 0.95 (3H, t, J=7.2 Hz), 1.72 (2H, tq, J=7.2, 7.2 Hz), 4.25 (2H, t, J=7.2 Hz), 6.09 (2H, dd, J=0.8, 3.6 Hz), 6.45 (2H, dd, J=1.6, 3.6 Hz), 6.70 (1H, dd, J=0.8, 1.2 Hz), 6.89-6.94 (3H, m), 7.67 (2H, dd, J=0.8, 1.6 Hz), 8.22 (1H, dd, J=0.8, 5.2 Hz).

Example 154

5-(6-Chloro-3-pyridyl)-4-(2-thienyl)-2-pyrimidinylamine

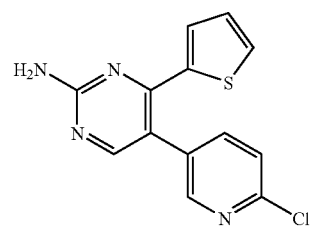

The title compound was obtained in a similar manner to Example 14 using 2-(6-chloro-3-pyridyl)-3-(dimethylamino)-1-(2-thienyl)-2-propen-1-one.

$^1$H NMR (400 MHz, DMSO-$d_6$) δ ppm; 6.73 (1H, dd, J=1.2, 4.0 Hz), 6.94 (2H, br s), 6.98 (1H, dd, J=4.0, 5.0 Hz), 7.59 (1H, dd, J=0.8, 8.2 Hz), 7.67 (1H, dd, J=1.2, 5.0 Hz), 7.83 (1H, dd, J=2.4, 8.2 Hz), 8.17 (1H, s), 8.36 (1H, dd, J=0.8, 2.4).

Example 155

5-(6-Chloro-3-pyridyl)-4-phenyl-2-pyrimidinylamine

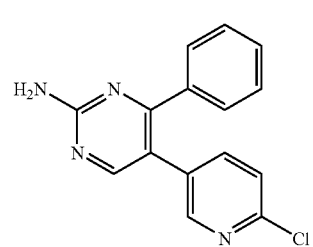

The title compound was obtained in a similar manner to Example 14 using 2-(6-chloro-3-pyridyl)-3-(dimethylamino)-1-phenyl-2-propen-1-one.

$^1$H NMR (400 MHz, DMSO-d$_6$) δ ppm; 7.01 (2H, br s), 7.27-7.40 (5H, m), 7.42 (1H, dd, J=0.8, 8.2 Hz), 7.55 (1H, dd, J=2.8, 8.2 Hz), 8.14 (1H, dd, J=0.8, 2.8 Hz), 8.35 (1H, s).

Example 156

5-(6-Chloro-3-pyridyl)-4-(3-fluorophenyl)-2-pyrimidinylamine

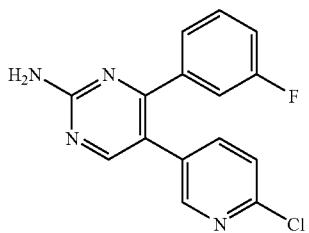

The title compound was obtained in a similar manner to Example 14 using 2-(6-chloro-3-pyridyl)-3-(dimethylamino)-1-(3-fluorophenyl)-2-propen-1-one.

$^1$H NMR (400 MHz, DMSO-d$_6$) δ ppm; 7.00-7.06 (1H, m), 7.07 (2H, br s), 7.15-7.25 (2H, m), 7.33-7.39 (1H, m), 7.44 (1H, dd, J=0.6, 8.2 Hz), 7.58 (1H, dd, J=2.6, 8.2 Hz), 8.18 (1H, dd, J=0.6, 2.6 Hz), 8.38 (1H, s).

The compounds represented by the above formula (I) according to the present invention are useful as an adenosine receptor (A$_1$, A$_{2A}$, A$_{2B}$ or A$_3$ receptor) antagonist and are specifically useful as an A$_{2B}$ receptor antagonist. Test examples demonstrating the efficacy of the compounds of the present invention as a medicament will be described below.

Test Example 1

Measurement of the binding affinity to adenosine A$_1$ receptor

A human adenosine A$_1$ receptor cDNA was expressed in excess in CHOK1 cells, and this membrane sample was suspended at a protein concentration of 66.7 μg/ml in 20 mM HEPES buffer, pH 7.4 (10 mM MgCl$_2$, 100 mM NaCl). To 0.45 ml of this membrane sample suspension were added 0.025 ml of 60 nM tritium-labeled chlorocyclopentyl adenosine ($^3$H-CCPA, from NEN Ltd.) and 0.025 ml of test compound. This mixture was left at 30° C. for 120 minutes, filtered rapidly under suction through a glass fiber filter (GF/B, from Whatman), and immediately washed twice with 5 ml of 50 mM water-cooled Tris-HCl buffer. Thereafter, the glass fiber filter was transferred to a vial, scintillator was added thereto, and the radioactivity on the filter was measured by a liquid scintillation counter. The inhibition of binding of $^3$H-CCPA to A$_1$ receptor by the test compound was determined using the following formula, and from this value, 50% inhibition concentration (IC$_{50}$) was calculated. Inhibition (%)=[1-{(binding in the presence of the test compound-nonspecific binding)/(total binding-nonspecific binding)}]×100

In the above formula, the total binding means $^3$H-CCPA-bound radioactivity in the absence of the test compound; the nonspecific binding means $^3$H-CCPA-bound radioactivity in the presence of 100 μM CPA ([R]-[1-methyl-2-phenylethyl] adenosine); and the binding in the presence of the test compound means $^3$H-CCPA-bound radioactivity in the presence of the test compound at predetermined concentrations. The inhibition constant (Ki value) in the table was determined from the formula of Cheng-Prusoff.

Test Example 2

Measurement of the Binding Ability to Adenosine A$_{2A}$ Receptor

An experiment of inhibition of binding to adenosine A$_{2A}$ receptor was conducted using a membrane sample (Receptor Biology Inc.) where an adenosine A$_{2A}$ receptor cDNA was expressed in excess. This membrane sample was suspended at a protein concentration of 22.2 μg/ml in 20 mM HEPES buffer, pH 7.4 (10 mM MgCl$_2$ and 100 mM NaCl). To 0.45 ml of this membrane sample suspension were added 0.025 ml of 500 nM tritium-labeled 2-p-[2-carboxyethyl]phenetylamino-5'-N-ethylarboxyamide adenosine ($^3$H-CGS21680, from NEN) and 0.025 ml of test compound. This mixture was left at 25° C. for 90 minutes, filtered rapidly under suction through a glass fiber filter (GF/B, from Whatman), and immediately washed twice with 5 ml of 50 mM ice-cooled Tris-HCl buffer. Thereafter, the glass fiber filter was transferred to a vial, scintillator was added thereto, and the radioactivity on the filter was measured by a liquid scintillation counter. The inhibition of binding of $^3$H-CGS21680 to A$_{2A}$ receptor by the test compound was determined using the following formula, and from this inhibition, 50% inhibition concentration (IC$_{50}$) was calculated.

Inhibition (%)=[1-{[(binding in the presence of the test compound)-(nonspecific binding)]/[(total binding)-(nonspecific binding)]}]×100

Here, the total binding means $^3$H-CGS21680-bound radioactivity in the absence of the test compound; the nonspecific binding means $^3$H-CGS21680-bound radioactivity in the presence of 100 μM RPIA; and the binding in the presence of the test compound means $^3$H-CGS21680-bound radioactivity in the presence of the test compound at predetermined concentrations. The inhibition constant (Ki value) in the table was determined from the formula of Cheng-Prusoff.

Test Example 3

Experiment of Inhibition of NECA-stimulated Production of cAMP in Adenosine A$_{2B}$ Receptor-expressing Cells CHOK1 cells where human adenosine A$_{2B}$ receptor had been expressed in excess were plated onto a 24-well plate at a density of 1.5×10$^5$ cells/well, cultured overnight, and used in the experiment. The degree of inhibitory effect of the test compound on the amount of cAMP produced by stimulation with 30 nM 5'-N-ethylcarboxyamide adenosine (NECA from Sigma) was evaluated in terms of affinity for A$_{2B}$ receptor. That is, the adhering cells were washed twice with 2 ml/well Krebs-Ringer buffer solution (containing 0.1% BSA; pH 7.4) and pre-incubated for 30 minutes in a volume of 0.5 ml/well. Then, a mixed solution containing NECA and the test compound was added in a volume of 0.1 ml/well in the presence of a phosphodiesterase inhibitor Ro-20-1724 (a product of RBI). After pre-incubation for 15 minutes, the reaction was terminated with 0.1 N HCl in a volume of 300 μl/well. Measurement of intracellular cAMP was carried out using a cAMP enzyme immunoassay kit produced by Amersham. The inhibition of NECA-stimulated production of cAMP by the test compound was determined using the following equation:

Inhibition (%)=[1−{(amount of cAMP in the coexistence of NECA and the test compound−amount of cAMP in only the Krebs-Ringer buffer solution)/(amount of cAMP upon stimulation with NECA only−amount of cAMP in only the Krebs-Ringer buffer solution)}]×100

The ability of the compound according to the present invention to bind to or the ability to antagonize adenosine receptor are as follows.

TABLE 1

| Test Compound | Ki (nM) $A_1$ | Ki (nM) $A_{2A}$ | IC$_{50}$ (nM) $A_{2B}$ |
|---|---|---|---|
| ~~Ex 16~~ | ~~175~~ | ~~6~~ | ~~29~~ |
| Ex 17 | 289 | 3 | 25 |
| Ex 18 | 114 | 2 | 26 |

The compounds according to the present invention, salts thereof or solvates of them have an excellent inhibitory action against the adenosine receptors.

Test Example 4

Evaluation of Defecation-Promoting Action

The defecation-promoting action of the adenosine $A_{2B}$ receptor-inhibiting compound which was identified by measuring the binding affinity or antagonistic activity thereof to the adenosine receptor in Test Examples 1 to 3, a salt thereof, a solvate of them, or a pharmaceutical composition containing it can be evaluated on the basis of the following method. That is, SD IGS rats (6 weeks-old, from Charles River) were placed in cages (3 animals/cage) and preliminarily allowed food and water ad libitum and raised for 1 week. Then, a tared water-absorbing sheet was placed below each cage, and the animals were fasted but allowed water ad libitum throughout the experiment. After 1.5 hours, the fecal pellets were collected from each cage and observed for abnormality before the experiment. The compound suspended or dissolved in 0.5% (w/v) methyl cellulose (MC) was orally administered in a volume of 5 ml/kg. On one hand, 0.5% (w/v) MC only was orally given to the control group. After administration of the compound, the rats were returned to the cage provided with a new water-absorbing sheet, and 90 minutes after the administration, the fecal pellets on the water-absorbing sheet were collected from each cage, and the external appearance was observed, and then counted and weighed. The number of fecal pellets is expressed per each cage.

TABLE 2

| Test Compound | Dose | Number of fecal pellets Mean ± S.E. |
|---|---|---|
| Control | — | 1.25 ± 0.63 |
| ~~Ex 16~~ | ~~3 mg/kg~~ | ~~12.50 ± 0.96~~ |
| Ex 17 | 3 mg/kg | 15.50 ± 3.18 |
| Ex 18 | 3 mg/kg | 14.50 ± 1.26 |

The compounds according to the present invention, a salt thereof or solvates of them have an excellent defecation-promoting action.

Test Example 5

Evaluation of Effects on Haloperidol-induced Catalepsy

Parkinson's disease is a disease caused by the degeneration or cell death of nigrostriatal dopaminergic neurons. The administration of haloperidol (dopamine $D_1/D_2$ receptor antagonist) blocks postsynaptic $D_2$ receptors to induce catalepsy. The haloperidol-induced catalepsy has been known as a classic model that mimics Parkinson's disease by drug administration (Eur. J. Pharmacol., 182, 327-334(1990)).

The adenosine $A_{2A}$ receptor antagonist compounds identified by measuring on their binding abilities to the receptors in Test Examples 1 to 3, the salts thereof, solvates of them, or pharmaceutical compositions containing those were evaluated for effect on haloperidol-induced catalepsy by the method described below. That is, the experiment was conducted by eight 5-week-old male ICR mice (available from Charles River) per group. Haloperidol (manufactured by Sigma Co., Ltd.) was dissolved in a 6.1% tartaric acid solution and the resulting solution in a dose of 1 mg/kg was then intraperitoneally administered to the mice. The test compound was used as a 0.5% MC suspension. 1.5 hours after the intraperitoneal administration of haloperidol, each of the suspension with the test compound and the suspension without the test compound (control) was orally administered to the mice (0.1 ml per 10 g of mouse body weight). 1 hour after the administration of the test compound, the degree of catalepsy was measured with respect to each of the mice such that a pair of only forelimbs and a pair of only hindlimbs of each mouse were placed by turns on a stand 4.5 cm in height and 10 cm in width. 0.1 mg/kg and 0.3 mg/kg of each of the test compounds were orally administered. Catalepsy scores and criterions are as follows.

Score Duration of catalepsy

0: When the pair of only forelimbs and the pair of only hindlimbs are independently placed on the stand, the duration of such a posture of each pair for less than 5 seconds.

1: The duration of the posture in which the forelimbs were being placed on the stand was 5 or more seconds but less than 10 seconds, and the duration of such a posture of the hindlimbs was less than 5 seconds.

2: The duration of the posture in which the forelimbs were being placed on the stand was 10 or more seconds, and the duration of such a posture of the pair hindlimbs was less than 5 seconds.

3: The duration of the posture in which both the forelimbs and hindlimbs were being placed on the stand was 5 or more seconds but less than 10 seconds; or the duration of the posture in which the forelimbs were being placed on the stand was less than 5 seconds and the duration of such a posture of the hindlimbs was 5 or more seconds.

4: The duration of the posture in which the forelimbs were being placed on the stand was 10 or more seconds and the duration of such a posture of the hindlimbs was 5 or more seconds but less than 10 seconds; or the duration of the posture in which the forelimbs were being placed on the stand was 5 or more seconds but less than 10 seconds and the duration of such a posture of the hindlimbs was 10 or more seconds.

5: The duration of the posture in which both the forelimbs and hindlimbs were being placed on the stand was 10 or more seconds.

The effects of the compound were determined by making a comparison between the score of the control group and the score of the test group in which the test compound was administered. A significant difference was analyzed by Dunnett's-test. The results are shown in Table 3.

TABLE 3

| Name of group | Administered content | Dose of Test Compound | Catalepsy score (Mean ± S.E.) |
|---|---|---|---|
| Control | Haloperidol | | 5.00 ± 0.00 |
| Example 16 | Haloperidol + Test compound | 0.1 mg/kg | 4.63 ± 0.38 |
| Example 16 | Haloperidol + Test compound | 1.0 mg/kg | 0.88 ± 0.64** |
| Example 17 | Haloperidol + Test compound | 0.1 mg/kg | 3.38 ± 0.53** |
| Example 17 | Haloperidol + Test compound | 1.0 mg/kg | 1.13 ± 0.67** |

**Example (comparison with Control group)

The invention claimed is:

1. A compound represented by the following formula (I), a salt thereof or a solvate thereof:

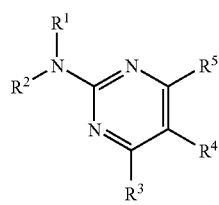

in the formula, $R^1$ and $R^2$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, an aromatic hydrocarbon cyclic group having six to fourteen carbon atoms which may be substituted, an acyl group having one to six carbon atoms which may be substituted or an alkylsulfonyl group having one to six carbon atoms which may be substituted; $R^3$ represents a hydrogen atom, a halogen atom, a cyano group, an alkyl group having one to six carbon atoms which may be substituted, an alkenyl group having two to six carbon atoms which may be substituted, an alkynyl group having two to six carbon atoms which may be substituted, an aromatic hydrocarbon cyclic group having six to fourteen carbon atoms which may be substituted, a nitrogen atom which may be substituted, an oxygen atom which may be substituted or a sulfur atom which may be substituted; $R^4$ is a group represented by the formula (V):

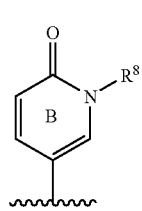

wherein $R^8$ represents a group selected from the following substituent group a; and the ring B may be substituted with one to four groups selected from the following substituent group a:

Substituent group a the group consisting of a hydrogen atom, a halogen atom, a hydroxyl group, a nitro group, a cyano group, an alkyl group having one to six carbon atoms which may be substituted, an alkenyl group having two to six carbon atoms which may be substituted, an alkynyl group having two to six carbon atoms which may be substituted, an alkoxy group having one to six carbon atoms which may be substituted, an alkenyloxy group having two to six carbon atoms which may be substituted, an alkynyloxy group having two to six carbon atoms which may be substituted, an alkylthio group having one to six carbon atoms which may be substituted, an alkenylthio group having two to six carbon atoms which may be substituted, an alkynylthio group having two to six carbon atoms which may be substituted, an aliphatic acyl group having two to seven carbon atoms, a carbamoyl group which may be substituted, an arylacyl group, an amino group which may be substituted, an alkylsulfonyl group having one to six carbon atoms which may be substituted, an alkenylsulfonyl group having two to six carbon atoms which may be substituted, an alkynylsulfonyl group having two to six carbon atoms which may be substituted, an alkylsulfinyl group having one to six carbon atoms which may be substituted, an alkenylsulfinyl group having two to six carbon atoms which may be substituted, an alkynylsulfinyl group having two to six carbon atoms which may be substituted, a formyl group, a cycloalkyl group having three to eight carbon atoms which may be substituted, a cycloalkenyl group having three to eight carbon atoms which may be substituted, and an aromatic hydrocarbon cyclic group having six to fourteen carbon atoms which may be substituted; and $R^5$ represents an aromatic hydrocarbon cyclic group having six to fourteen carbon atoms which may be substituted or furyl which may be substituted.

2. A pharmaceutical composition comprising the compound according to claim 1, a salt thereof or a solvate thereof.

3. A method for promoting defecation, which comprises administering a pharmacologically effective amount of the compound according to claim 1, a salt thereof or a solvate thereof to a patient in need thereof.

4. A compound selected from the group consisting of:
  (1) 5-(2-amino-4-(2-furyl)-5-pyrimidinyl-1-methyl-1,2-dihydro-2-pyridinone;
  (2) 5-[2-amino-4-(2-furyl)-5-pyrimidinyl]-1-ethyl-1,2-dihydro-2-pyridinone;
  (3) 1-allyl-5-[2-amino-4-(2-furyl)-5-pyrimidinyl]-1,2-dihydro-2-pyridinone;
  (4) 5-[2-amino-4-(3-fluorophenyl)-5-pyrimidinyl]-1-methyl-1,2-dihydro-2-pyridinone;
  (5) 5-(2-amino-4-phenyl-5-pyrimidinyl)-1-methyl-1,2-dihydro-2-pyridinone;
  (6) 5-[2-amino-4,6-di(2-furyl)-5-pyrimidinyl]-1-methyl-1,2-dihydro-2-pyridinone; and
  (7) 5-[2,4-diamino-6-(3-fluorophenyl)-5-pyrimidinyl]-1-methyl-1,2-dihydro-2-pyridinone, and a salt or a solvate thereof.

5. The compound according to claim 1, a salt thereof or a solvate thereof, wherein $R^1$ mid $R^2$ are hydrogen atoms.

6. The Compound according to claim 1, a salt thereof or a solvate thereof, wherein $R^3$ represents a hydrogen atom, an amino group, a cyano group, or an alkyl group having one to six carbon atoms, an alkoxyl group having one to six carbon atoms, phenyl, or naphthyl, each of which may be substituted.

7. The compound according to claim 1, a salt thereof or a solvate thereof, wherein $R^3$ is a hydrogen atom.

8. The compound according to claim 1, a salt thereof or a solvate thereof, wherein $R^5$ represents a phenyl, 2-furyl or 3-furyl, each of which may be substituted.

9. The compound according to claim 1, a salt thereof or a solvate thereof, wherein $R^5$ represents a phenyl, or 2-furyl, each of which, may be substituted.

10. The compound according to claim 1, a salt thereof or a solvate thereof, wherein the Substituent group a consists of a hydrogen atom, a halogen atom, an alkyl group having one to six carbon atoms which may be substituted, an alkenyl group having two to six carbon atoms which may be substituted, an alkynyl group having two to six carbon atoms which may be substituted, an alkoxy group having one to six carbon atoms which may be substituted, a carbamoyl group which may be substituted, and an amino group which may be substituted.

11. A method for treating Parkinson's disease or depression comprising administering a pharmacologically effective amount of a compound according to claim 1, a salt thereof or a solvate thereof, to a patient in need thereof.

12. A method for treating constipation comprising administering a pharmacologically effective amount of a compound according to claim 1, a salt thereof or a solvate thereof, to a patient in need thereof.

13. The method of claim 12, wherein the constipation is functional constipation.

14. A method for treating irritable bowel syndrome, constipation accompanying irritable bowel syndrome, organic constipation, constipation accompanying enteroparalytic ileus, constipation accompanying congenital digestive tract dysfunction or constipation accompanying ileus comprising administering a pharmacologically effective amount of a compound according to claim 1, a salt thereof or a solvate thereof, to a patient in need thereof.

15. A method for evacuating intestinal tracts at the time of examination of digestive tracts or before and alter an operation comprising administering a pharmacologically effective amount of a compound according to claim 1, a salt thereof or a solvate thereof, to a patient in need thereof.

16. A compound selected from the group consisting of:
(1) 5-[2-Amino-4-(2-furyl)-5-pyrimidinyl]-1-(2-fluoroethyl)-1,2-dihydro-2-pyridinone;
(2) 5-[2-Amino-4-(2-furyl)-5-pyrimidinyl]-1-(8-hydroxyoctyl)-1,2-dihydro-2-pyridinone;
(3) Methyl 4-{5-[2-amino-4-(2-furyl)-5-pyrimidinyl]-2-oxo-1,2-dihydro-1-pyridinyl}butanoate;
(4) 5-[2-Amino-4-(2-furyl)-5-pyrimidinyl]-1-(2-propynyl)-1,2-dihydro-2-pyridinone;
(5) 5-[2-Amino-4-(2-furyl)-5-pyrimidinyl]-1-isobutyl-1,2-dihydro-pyridinone;
(6) 5-[2-Amino-4-(2-furyl)-5-pyrimidinyl]-1-(2-butynyl)-1,2-dihydro-2-pyridinone;
(7) 5-[2-Amino-4-(2-furyl)-5-pyrimidinyl]-1-benzyl-1,2-dihydro-2-pyridinone;
(8) 5-[2-Amino-4-(2-furyl)-5-pyrimidinyl]-1-isopenty1-1,2-dihydro-2-pyridinone;
(9) 5-[2-Amino-4-(2-furyl)-5-pyrimidinyl]-1-(2-methylbutyl)-1,2-dihydro-2-pyridinone;
(10) 5-[2-Amino-4-(2-furyl)-5-pyrimidinyl]-1-octyl-1,2-dihydro-2-pyridinone;
(11) 2-{5-[2-Amino-4-(2-furyl)-5-pyrimidinyl]-2-oxo-1,2-dihydro-1-pyridinyl}ethylcyanide;
(12) 5-[2-Amino-4-(2-furyl)-5-pyrimidinyl]-1-(3-fluoropropyl)-1,2-dihydro-2-pyridinone;
(13) 5-[2-Amino-4-(2-furyl)-5-pyrimidinyl]-1-(2-hydroxyethyl)-1,2dibydro-2-pyridinone;
(14) 5-[2-Amino-4-(2-furyl)-5-pyrimidinyl]-1-(3-hydroxypropyl)-1,2-dihydro-2-pyridinone; and
(15) 5-[2-Amino-4-(2-furyl)-5-pyrimidinyl]-1-(2-methoxyethyl)-1,2-dihydro-2-pyridinone; and a salt or a solvate thereof.

17. 5-[2-Amino-4-(2-furyl)-5-pyrimidinyl]-1-(2-fluoroethyl)-1,2-dihydro-2-pyridinone, a salt thereof or a solvate thereof.

18. 5-[2-Amino-4-(2-furyl)-5-pyrimidinyl]-1-(8-hydroxyoctyl)-1,2-dihydro-2-pyridinone, a salt thereof or a solvate thereof.

19. Methyl 4-{5-[2-amino-4-(2-furyl)-5-pyrimidinyl]-2-oxo-1,2-dihydro-1-pyridinyl}butanoate, a salt thereof or a solvate thereof.

20. 5-[2-Amino-4-(2-furyl)-5-pyrimidinyl]-1-(2-propynyl)-1,2-dihydro-2-pyridinone, a salt thereof or a solvate thereof.

21. 5-[2-Amino-4-(2-furyl)-5-pyrimidinyl]-1-isobutyl-1,2-dihydro-pyridinone, a salt thereof or a solvate thereof.

22. 5-[2-Amino-4-(2-furyl)-5-pyrimidinyl]-1-(2-butynyl)-1,2-dihydro-2-pyridinone, a salt thereof or a solvate thereof.

23. 5-[2-Amino-4-(2-furyl)-5-pyrimidinyl]-1-benzyl-1,2-dihydro-2-pyridinone, a salt thereof or a solvate thereof.

24. 5-[2-Amino-4-(2-furyl)-5-pyrimidinyl]-1-isopentyl-1,2-dihydro-2-pyridinone, a salt thereof or a solvate thereof.

25. 5-[2-Amino-4-(2-furyl)-5-pyrimidinyl]-1-(2-methylbutyl)-1,2-dihydro-2-pyridinone, a salt thereof or a solvate thereof.

26. 5-[2-Amino-4-(2-furyl)-5-pyrimidinyl]-1-octyl-1,2-dihydro-2-pyridinone, a salt thereof or a solvate thereof.

27. 2-{5-[2-Amino-4-(2-furyl)-5-pyrimidinyl]-2-oxo-1,2-dihydro-1-pyridinyl}ethylcyanide, a salt thereof or a solvate thereof.

28. 5-[2-Amino-4-(2-furyl)-5-pyrimidinyl]-1-(3-fluoropropyl)-1,2-dihydro-2-pyridinone, a salt thereof or a solvate thereof.

29. 5-[2-Amino-4-(2-furyl)-5-pyrimidinyl]-1-(2-hydroxyethyl)-1,2-dihydro-2-pyridinone, a salt thereof or a solvate thereof.

30. 5-[2-Amino-4-(2-furyl)-5-pyrimidinyl]-1-(3-hydroxypropyl)-1,2-dihydro-2-pyridinone, a salt thereof or a solvate thereof.

31. 5-[2-Amino-4-(2-furyl)-5-pyrimidinyl]-1-(2-methoxyethyl)-1,2-dihydro-2-pyridinone, a salt thereof or a solvate thereof.

32. A method for antagonizing an adenosine $A_2$ receptor in vitro comprising administering a compound according to claim 1, a salt thereof or a solvate thereof, to an adenosine $A_2$ receptor in vitro.

33. A method for antagonizing an adenosine $A_{2A}$ receptor in vitro comprising administering a compound according to claim 1, a salt thereof or a solvate thereof, to an adenosine $A_{2A}$ receptor in vitro.

34. A method for antagonizing an adenosine $A_{2B}$ receptor in vitro comprising administering a compound according to claim 1, a salt thereof or a solvate thereof to an adenosine $A_{2B}$ receptor in vitro.

* * * * *